United States Patent
Xu et al.

(10) Patent No.: US 12,070,208 B2
(45) Date of Patent: Aug. 27, 2024

(54) SURGICAL EFFECTOR, SURGICAL TOOL AND SURGICAL ROBOT

(71) Applicant: BEIJING SURGERII ROBOTICS COMPANY LIMITED, Beijing (CN)

(72) Inventors: Kai Xu, Beijing (CN); Yitang Ren, Beijing (CN)

(73) Assignee: BEIJING SURGERII ROBOTICS COMPANY LIMITED, Beijing (CN)

( * ) Notice: Subject to any disclaimer, the term of this patent is extended or adjusted under 35 U.S.C. 154(b) by 170 days.

(21) Appl. No.: 17/790,117

(22) PCT Filed: Dec. 21, 2020

(86) PCT No.: PCT/CN2020/138011
§ 371 (c)(1),
(2) Date: Jun. 29, 2022

(87) PCT Pub. No.: WO2021/136004
PCT Pub. Date: Jul. 8, 2021

(65) Prior Publication Data
US 2023/0052924 A1    Feb. 16, 2023

(30) Foreign Application Priority Data

Dec. 30, 2019 (CN) .......................... 201911391778.9
Dec. 30, 2019 (CN) .......................... 201911391781.0
(Continued)

(51) Int. Cl.
A61B 17/064 (2006.01)
A61B 17/068 (2006.01)
A61B 17/072 (2006.01)

(52) U.S. Cl.
CPC .. *A61B 17/068* (2013.01); *A61B 2017/07271* (2013.01)

(58) Field of Classification Search
CPC ............... A61B 17/115; A61B 17/1155; A61B 2017/07207
See application file for complete search history.

(56) References Cited

U.S. PATENT DOCUMENTS 5,467,911 A * 11/1995 Tsuruta ............. A61B 17/0684
227/19
5,527,313 A   6/1996 Scott
(Continued)

FOREIGN PATENT DOCUMENTS

CN    201775678 U    3/2011
CN    102178559 A    9/2011
(Continued)

OTHER PUBLICATIONS

Office Action in related Canadian Application No. 3165884 dated Oct. 12, 2023 (5 pages).
(Continued)

*Primary Examiner* — Eyamindae C Jallow
(74) *Attorney, Agent, or Firm* — Bayes PLLC

(57) ABSTRACT

A surgical effector, a surgical tool, and a surgical robot are provided. The surgical effector includes a support part, a head part, a drive part, and a sealing member. The support part includes an inner cavity, the head part is at least partially movably arranged at a distal end of the support part, the drive part is slidably arranged in the inner cavity of the support part and is connected to a proximal end of the head part, the sealing member is connected to the drive part in a sealed manner at a first end thereof and is connected to the support part in a sealed manner at a second end thereof, and at least a part of the sealing member is deformable.

20 Claims, 36 Drawing Sheets

(30) Foreign Application Priority Data

Dec. 30, 2019 (CN) .......................... 201911392107.4
Dec. 30, 2019 (CN) .......................... 201911392141.1
Dec. 30, 2019 (CN) .......................... 201911393792.2

(56) References Cited

U.S. PATENT DOCUMENTS

| | | |
|---|---|---|
| 5,603,711 A | 2/1997 | Parins et al. |
| 5,637,110 A | 6/1997 | Pennybacker et al. |
| 8,231,652 B2 | 7/2012 | Freed et al. |
| 2004/0098041 A1 | 5/2004 | Wagner et al. |
| 2005/0113827 A1 | 5/2005 | Dumbauld et al. |
| 2007/0078458 A1 | 4/2007 | Dumbauld et al. |
| 2007/0084899 A1 | 4/2007 | Taylor |
| 2007/0106295 A1 | 5/2007 | Garrison et al. |
| 2008/0015566 A1 | 1/2008 | Livneh |
| 2010/0145334 A1 | 6/2010 | Olson et al. |
| 2010/0179540 A1 | 7/2010 | Marczyk et al. |
| 2012/0209289 A1 | 8/2012 | Duque et al. |
| 2014/0277106 A1 | 9/2014 | Crews et al. |
| 2017/0150965 A1* | 6/2017 | Williams ............ A61B 17/1155 |
| 2019/0125476 A1* | 5/2019 | Shelton, IV ....... A61B 17/1285 |

FOREIGN PATENT DOCUMENTS

| | | |
|---|---|---|
| CN | 102204844 A | 10/2011 |
| CN | 102281828 A | 12/2011 |
| CN | 103419179 A | 12/2013 |
| CN | 103619279 A | 3/2014 |
| CN | 107205787 A | 9/2017 |
| CN | 107582108 A | 1/2018 |
| CN | 108113756 A | 6/2018 |
| CN | 109350236 A | 2/2019 |
| CN | 109498149 A | 3/2019 |
| CN | 110037820 A | 7/2019 |
| CN | 209404944 U | 9/2019 |
| CN | 209595885 U | 11/2019 |
| CN | 209770428 U | 12/2019 |
| CN | 209770446 U | 12/2019 |
| DE | 4220644 C1 | 1/1994 |
| WO | 2005004734 A1 | 1/2005 |
| WO | 2010104755 A1 | 9/2010 |

OTHER PUBLICATIONS

Extended European Search Report in related European Application No. 20910042.9 dated Oct. 2, 2023 (8 pages).
Search Report issued in corresponding International Application No. PCT/CN/2020/138011, dated Mar. 23, 2021, 4 pages.
Search Report issued in related Chinese Application No. 2020109760640 dated Jul. 20, 2023 (3 pages).
Search Report issued in related Chinese Application No. 2020109743147 dated Jul. 21, 2023 (3 pages).
Search Report issued in related Chinese Application No. 2020109742892 dated Aug. 29, 2023 (3 pages).

* cited by examiner

SURGICAL EFFECTOR, SURGICAL TOOL AND SURGICAL ROBOT

CROSS-REFERENCE TO RELATED APPLICATIONS

This application is a national stage of International Application No. PCT/CN2020/138011, filed on Dec. 21, 2020, which claims priority to Chinese Patent Application Nos. 201911393792.2, filed on Dec. 30, 2019; 201911392107.4, filed on Dec. 30, 2019; 201911392141.1, filed on Dec. 30, 2019; 201911391781.0, filed on Dec. 30, 2019; and 201911391778.9, filed on Dec. 30, 2019. The entire contents of each of the above-identified applications are expressly incorporated herein by reference.

TECHNICAL FIELD

The present disclosure relates to the field of medical instruments, and particularly to a surgical effector, a surgical tool, and a surgical robot.

BACKGROUND

Surgical tools are often used in minimally invasive medical procedures, which include various surgical effectors, such as forceps, cutting tools, or needle holders. The surgical tools can be further classified into electrical or non-electrical surgical tools in terms to their functions. The electrical surgical tools refer to, for example, bipolar or monopolar electrical surgical tools. A surgical effector is usually installed at an end of a surgical tool, and the surgical effector is inserted into a small incision or a natural orifice of a patient directly or via a cannula to carry out corresponding surgical operations.

Existing surgical tools can be classified into disposable surgical tools and reusable surgical tools: most of the disposable surgical tools are made of a combination of macromolecular materials and stainless steel materials, but there is a risk of falling off of stainless steel, which is likely to cause surgical accidents; and main bodies of the reusable surgical tools are generally made of stainless steel materials, thus the products are not easy to be damaged and can be repeatedly disinfected and used, but their recovery procedures after surgery are complicated, and if the disinfection and sterilization is not thorough in a later stage, it is likely to cause problems such as secondary contamination and infection.

The existing reusable surgical tools are often sterilized by disassembling surgical tool parts or by cleaning channels during disinfection and sterilization. The former cleaning method has high costs, complicated process, and is likely to cause wear and loosening of the parts. The latter cleaning method, due to the long channels, has a poor flushing effect, and is likely to cause less thorough disinfection and produce residues difficult to find, resulting in secondary contamination in the later stage.

SUMMARY

In some embodiments, the present disclosure provides an exemplary surgical effector, which comprises: a support part comprising an inner cavity; a head part at least partially movably arranged at a distal end of the support part; a drive part slidably arranged in the inner cavity of the support part and connected to a proximal end of the head part; a sealing member connected to the drive part in a sealed manner at a first end thereof and connected to the support part in a sealed manner at a second end thereof, at least a part of the sealing member being deformable.

In some embodiments, the present disclosure further provides a surgical tool, comprising a drive part, a surgical tool arm, and the surgical effector of the foregoing technical solution, wherein the surgical effector is arranged at a distal end of the surgical tool arm, the drive part is arranged at a proximal end of the surgical tool arm, and the drive part is used to drive the surgical tool arm or the surgical effector to move.

In some embodiments, the present disclosure further provides a surgical robot, comprising at least one control device, at least one surgical cart, at least one robot arm, at least one surgical tool, and at least one surgical effector of the foregoing technical solution, wherein the at least one robot arms is arranged on the at least one surgical cart, the at least one surgical tool is arranged at a distal end of the at least one robot arm, the at least one surgical effector is arranged at a distal end of the at least one surgical tool, and the at least one control device is configured to control the movement of the at least one surgical tool and/or the at least one surgical effector.

BRIEF DESCRIPTION OF DRAWINGS

In order to describe the technical solutions in the embodiments of the present disclosure in greater detail, the accompanying drawings that are required for describing the embodiments of the present disclosure will be briefly introduced below. Apparently, the accompanying drawings in the following description are merely for some embodiments of the present disclosure, and for those of ordinary skill in the art, other drawings would also have been obtained according to the content of the embodiments of the present disclosure and these accompanying drawings without involving any inventive effort.

DETAILED DESCRIPTION

In order to make the technical problems solved by the present disclosure, the technical solutions adopted by the present disclosure, and the technical effects achieved by the present disclosure clearer, the technical solutions in the embodiments of the present disclosure will be described in further detail below with reference to the accompanying drawings. It is apparent that the described embodiments are some of, rather than all of, the embodiments of the present disclosure. All other embodiments obtained by those skilled in the art on the basis of the embodiments in the present disclosure without any inventive effort shall fall within the scope of protection of the present disclosure.

In the description of the present disclosure, it should be noted that the orientation or positional relationship indicated by the terms "center", "upper", "lower", "left", "right", "vertical" "horizontal", "inner", "outer", etc. are based on the orientation or positional relationship shown in the accompanying drawings and are intended to facilitate in describing the present disclosure and simplify the description only, rather than indicating or implying that the device or element referred to must have a particular orientation or be constructed and operated in a particular orientation, and shall not be interpreted as limiting the present disclosure. In addition, the terms "first" and "second" are descriptive purposes only and should not be construed as indicating or implying relative importance. Herein, the terms "first position" and "second position" are two different positions.

In the description of the present disclosure, it should be noted that unless otherwise explicitly specified and defined, the terms "mounting", "connecting" and "connection" should be understood in a broad sense, for example, they may be a fixed connection or a detachable connection; may be a mechanical connection or an electrical connection; and may be a direct connection or an indirect connection by means of an intermediate medium, or may be communication between interiors of two elements. For those of ordinary skill in the art, the specific meanings of the terms mentioned above in the present disclosure should be construed according to specific circumstances.

In the present disclosure, the end close to an operator is defined as a proximal end, a proximal part, a rear end or a rear part, and the end close to a surgical patient is defined as a distal end, a distal part, a front end or a front part.

Figure 1:
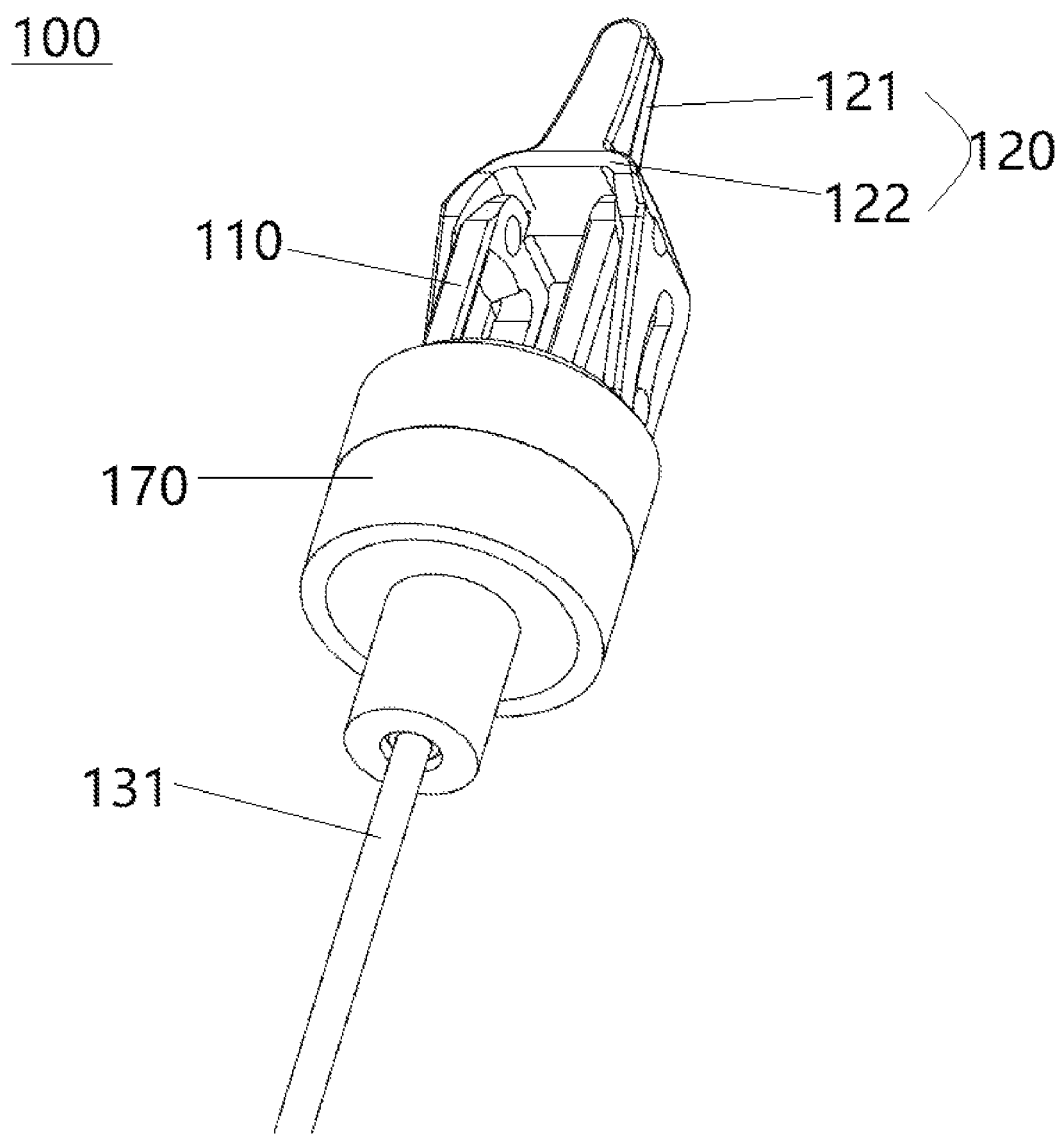
FIG. 1 shows a perspective schematic structural view of a surgical effector according to some embodiments of the present disclosure.
Figure 2:
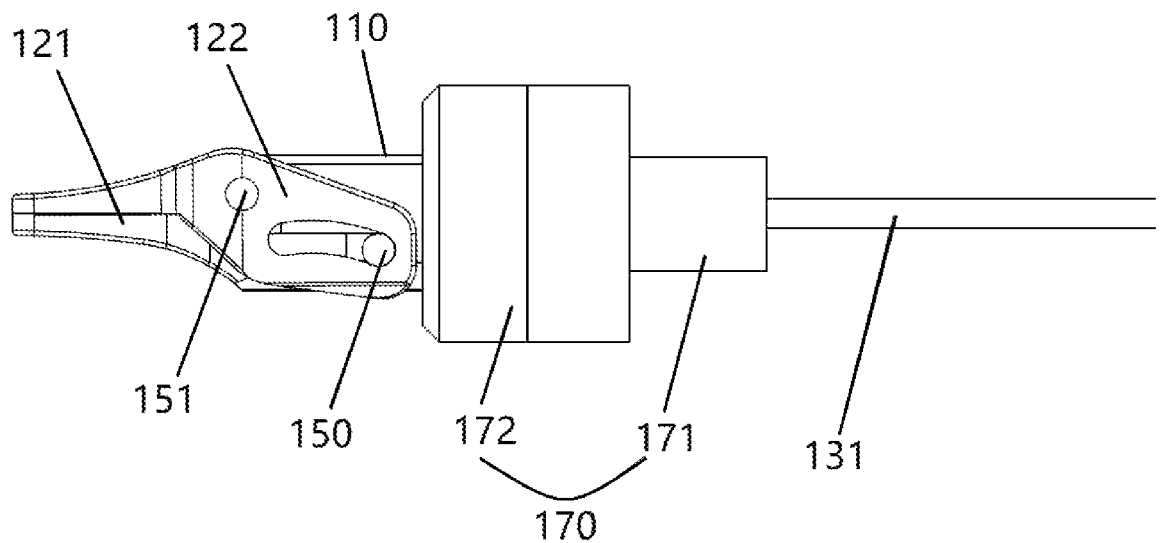
FIG. 2 shows a left side view of a surgical effector according to some embodiments of the present disclosure.
Figure 3:
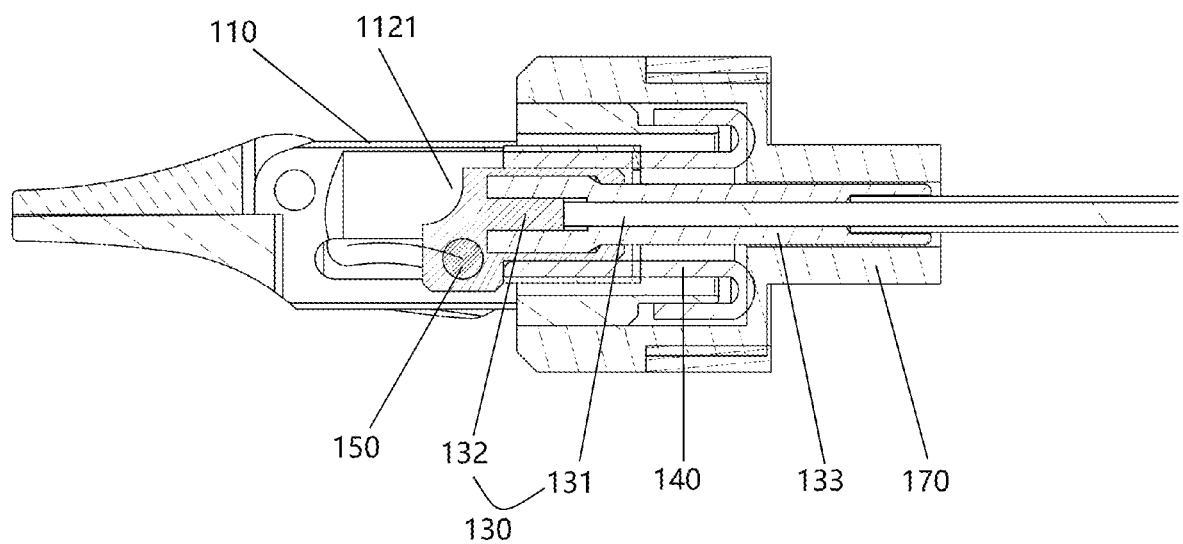
FIG. 3 shows an axial sectional view of a surgical effector according to some embodiments of the present disclosure.

FIGS. 1 to 3 respectively show a perspective schematic structural view, a left view, and an axial sectional view of a surgical effector 100 according to some embodiments of the present disclosure. The surgical effector 100 may comprise a head part 120, a support part 110, a drive part 130, and a sealing member 140.

The head part 120 is at least partially movably arranged at a distal end of the support part 110, and is supported by the support part 110. As shown in FIG. 3, the support part 110 may comprise an inner cavity 1121, the drive part 130 may be movably arranged in the inner cavity 1121 of the support part 110 and is connected to a proximal end of the head part 120, so that at least a part of the head part 120 is driven to move relative to the distal end of the support part 110 by the movement of the drive part inside the support part 110. It can be understood that the head part 120 may be any tool used in the surgical effector that can be opened and closed, such as separating forceps, grasping forceps, a needle holder, and curved scissors.

The sealing member 140 may have a first end (e.g., a proximal end, or a distal end shown in FIG. 3) connected to the drive part 130 in a sealed manner and a second end (e.g., a distal end, or a proximal end shown in FIG. 3) connected to the support part 110 in a sealed manner, and at least a part of the sealing member 140 is deformable. Therefore, when the drive part 130 is relatively moved in the support part 110, the sealing member 140 can be deformed adaptively. The sealing member 140 can form a sealed isolation between the drive part 130, the support part 110 and the head part 120, so as to prevent patient's body fluids, bacteria and viruses from entering the interior of the surgical effector 100 through pores during a surgical operation, thereby facilitating repeated cleaning and disinfection of the surgical effector 100.

At least a part of the sealing member 140 may comprise an elastically stretchable material such as rubber or thermoplastic elastomer, or a flexible material such as plastic and non-woven fabric. In some embodiments, as shown in FIG. 3, the sealing member 140 may comprise a first end portion, a second end portion, and a transition portion between the first end and the second end. The first end portion and the second end portion may be respectively connected to an outer peripheral surface of the drive part 130 and an outer peripheral surface of a proximal end of the support part 110 in a sealed manner, for example, by means of adhesive bonding, thermoplastic forming, ferrules, etc. At least a part of the transition portion may comprise a flexible material, or at least a part of the transition portion may comprise a folding part that can be expanded or collapsed. Therefore, when the drive part 130 is moved in the support part 110, the sealing member 140 can be adaptively deformed, so as to achieve sealing without affecting the relative movement between the drive part 130 and the support part 110.

Figure 5:
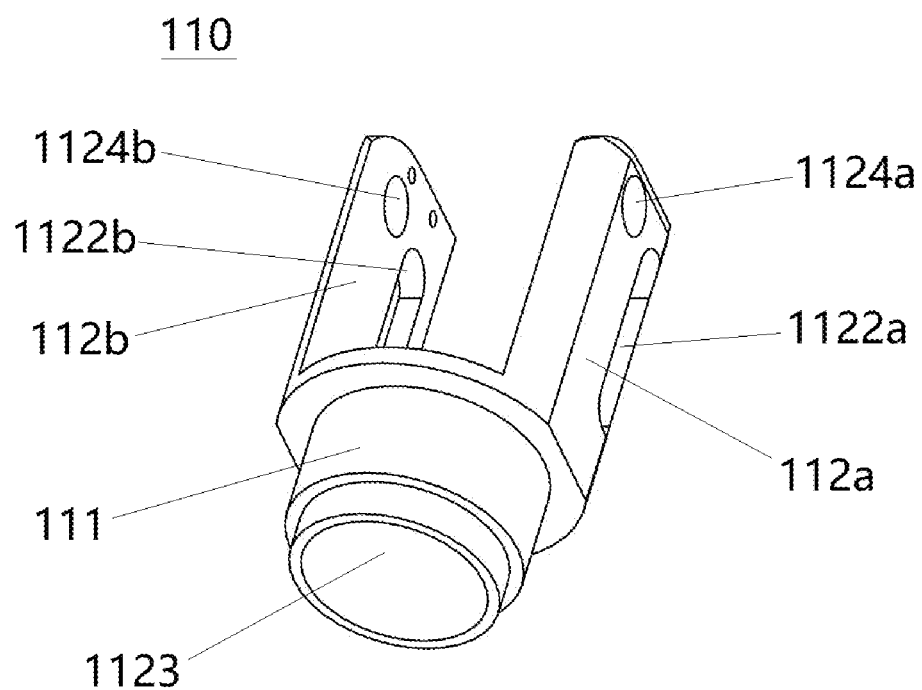
FIG. 5 shows a perspective view of a support part according to some embodiments of the present disclosure.
Figure 6:
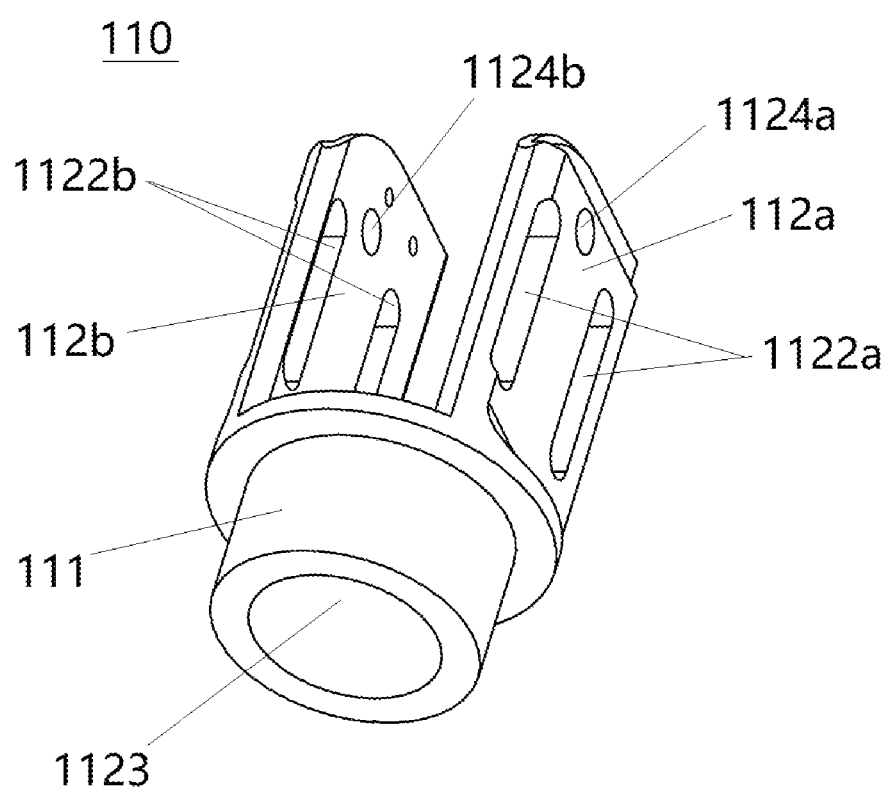
FIG. 6 shows a perspective view of a support part according to some other embodiments of the present disclosure.

FIGS. 5 and 6 respectively show a perspective view of a support part 110 according to some embodiments of the present disclosure. In some embodiments, the support part 110 may comprise at least one pair of support part slide slots 1122*a-b*. As shown in FIG. 5, the support part slide slots 1122*a-b* may be a pair of axial slide slots radially opposed to each other and extending axially. In some embodiments, as shown in FIG. 6, the support part 110 may comprise two pairs of support part slide slots 1122*a-b*, which may be two pairs of axial slide slots radially opposed to each other and extending axially.

In some embodiments, as shown in FIGS. 5 and 6, the support part 110 may comprise a support connector 111 at the proximal end and at least one support member (e.g., a pair of support members 112*a-b*) arranged circumferentially spaced apart from each other at a distal end of the support connector 111. The support connector 111 may be tubular, and its cross section may be circular, oval, rectangular, polygonal, etc. An axially-arranged hollow slideway 1123 is formed in the support connector (also referring to FIG. 4). A support member 112*a* and a support member 112*b* may be arranged opposite each other, and the support part slide slots 1122*a-b* may be oppositely formed in the support members 112*a-b*, respectively. The support members 112 may be fixedly connected to or integrally molded with the support connector 111. In some embodiments, the support members 112 of the support part 110 may be tubular or partially tubular, and their cross sections may be circular, oval, rectangular, polygonal, etc. By arranging the support members 112 that are circumferentially spaced apart from each other, hollow structures are increased at the distal end of the support part 110, internal pores and the shielding area are reduced, thereby facilitating cleaning of the distal end of the surgical tool. The support part slide slots 1122*a-b* are oppositely formed on side walls of the support part 110. In some embodiments, the support part 110 may comprise a plurality of support members 112 arranged spaced apart from one another so as to facilitate cleaning of the surgical tool.

Figure 4:
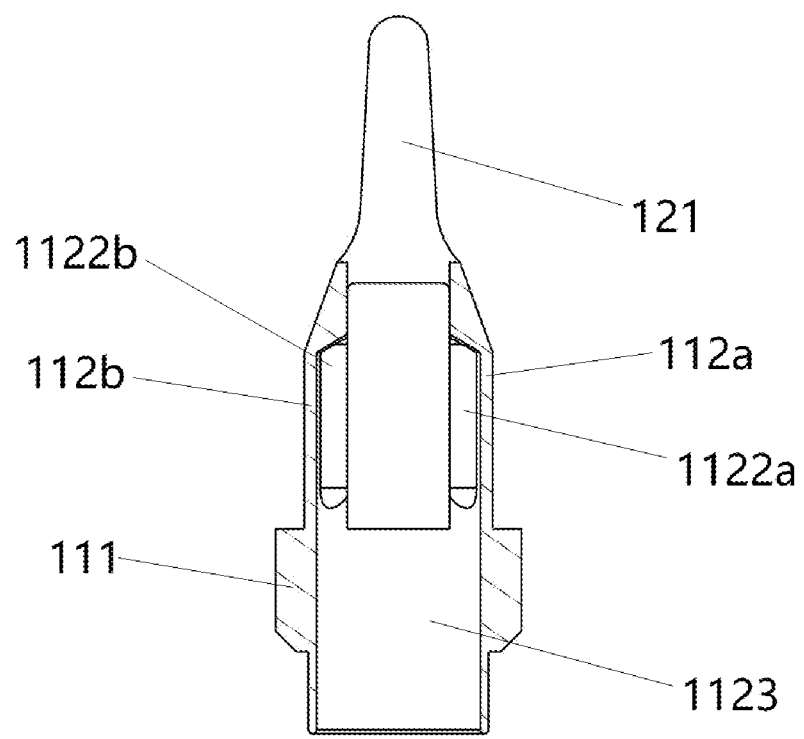
FIG. 4 shows a sectional view of a first head member and a support part according to some embodiments of the present disclosure.

As shown in FIGS. 1 to 3, the head part 120 may comprise a first head member 121 and a second head member 122 capable of incorporating with the first head member 121. In some embodiments, as shown in FIGS. 1 and 2, the first head member 121 may be fixedly arranged at the distal end of the support part 110, for example, by means of welding, bonding or integral molding. The second head member 122 may be rotatably connected to the first head member 121 or the support part 110, for example, by means of hinging. FIG. 4 shows a sectional view of a first head member 121 and a support part 110 according to some embodiments of the present disclosure. As shown in FIG. 4, the first head member 121 is fixedly arranged at a distal end of the support part 110. In some embodiments, the first head member 121 may be integrally molded with the support part 110.

Figure 7:
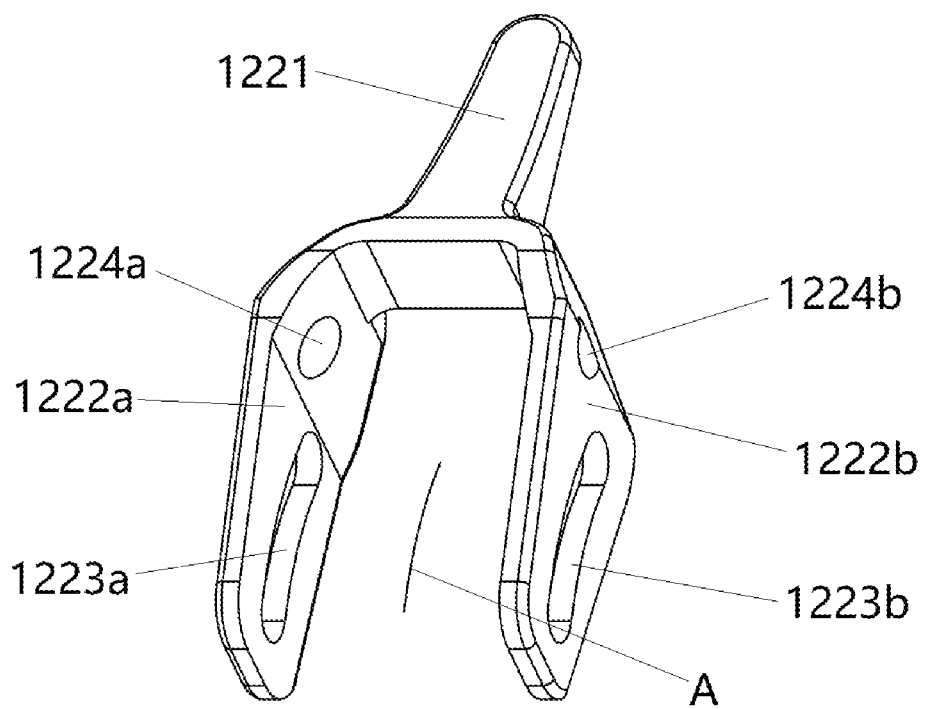
FIG. 7 shows a perspective view of a second head member according to some embodiments of the present disclosure.

FIG. 7 shows a perspective view of a second head member 122 according to some embodiments of the present disclosure. As shown in FIG. 7, the second head member 122 may comprise a jaw 1221 and a pair of jaw support members 1222*a* and 1222*b* which are connected to and support the jaw 1221. The pair of jaw support members 1222*a-b* may be symmetrically arranged on two sides of a proximal end of the jaw 1221. Distal ends of the jaw support members 1222*a-b* are respectively provided with connecting holes 1224*a-b* opposed to each other. As shown in FIG. 7, the jaw support members 1222*a-b* may comprise jaw slide slots 1223*a-b*, respectively. In some embodiments, the jaw slide slots 1223*a-b* may be arc-shaped slide slots, and the jaw slide slots 1223*a-b* are arranged opposite each other on the jaw support members 1222*a-b*. Each arc-shaped slide slot may have a contour of, for example, an arc A, as shown in FIG. 7. The contour line of the arc-shaped slide slot is composed of one or more arcs. A clamping force output by the surgical tool can be adjusted by adjusting a curvature of the arc. Those skilled in the art should understand that the contour line of the arc-shaped slide slot may alternatively be an approximate arc formed from a plurality of straight line segments. In some embodiments, as shown in FIG. 7, the jaw support members 1222*a-b* may comprise connecting holes 1224*a-b*, respectively. The connecting holes 1224*a-b* may be used for mounting of the second head member 122, as will be described in detail below.

In some embodiments, the drive part 130 comprises a drive wire 131, as shown in FIGS. 1 and 3. In some embodiments, the drive wire 131 may be a nickel-titanium wire or a steel wire. The head part is driven by pushing and/or pulling the drive wire, and the drive structure can be simplified in the case where one jaw is driven to move and the other jaw is fixedly arranged. Therefore, this can be widely used in various minimally invasive operations, especially in a minimally invasive surgical robot such as an endoscopic surgical robot.

In some embodiments, as shown in FIG. 1, the jaw support members 1222*a-b* may be arranged outside the support part 110. Those skilled in the art can understand that, in some embodiments, the jaw support members 1222*a-b* may alternatively be arranged inside the support part 110. As shown in FIG. 2, a drive part connecting pin 150 may be slidably arranged in the support part slide slots 1122a-b (as shown in FIG. 5) and the jaw slide slots 1223a-b (as shown in FIG. 7). A pivotal connecting pin 151 passes through a pair of connecting holes 1224a-b (as shown in FIG. 7), and two ends of the pivotal connecting pin are respectively pivotally connected to the pair of support part connecting holes 1124a-b (referring to FIGS. 5 and 6) of the support part 110, so that the second head member 122 is hinged to the support part 110. The drive part connecting pin 150 is connected to a distal end of the drive wire 131. When the drive wire 131 is pushed and/or pulled to relatively move in the hollow slideway 1123 of the support part 110, the drive part connecting pin 150 is driven to slide back and forth along the jaw slide slots 1223a-b and the support part slide slots 1122a-b, thereby driving the second head member 122 to be opened and closed relative to the first head member 121.

In some embodiments, a pair of drive part connecting pins 150 are respectively slidably arranged in two pairs of support part slide slots 1122a-b (as shown in FIG. 6), and one of the drive part connecting pins 150 is also slidably arranged in the jaw slide slots 1223a-b. The pair of drive part connecting pins 150 are both connected to the distal end of the drive wire 131, so that under the driving of the drive wire 131, the pair of drive part connecting pins 150 can slide along the support part slide slots 1122a-b. The drive part connecting pins 150 arranged in the jaw slide slots 1223a-b can also reciprocate along the support part slide slots 1122a-b, so that the second head member 122 is driven to be opened and closed relative to the first head member 121. With the two pairs of support part slide slots 1122a-b, and the drive part connecting pins 150 respectively arranged therein, more stable driving is achieved.

Figure 8:
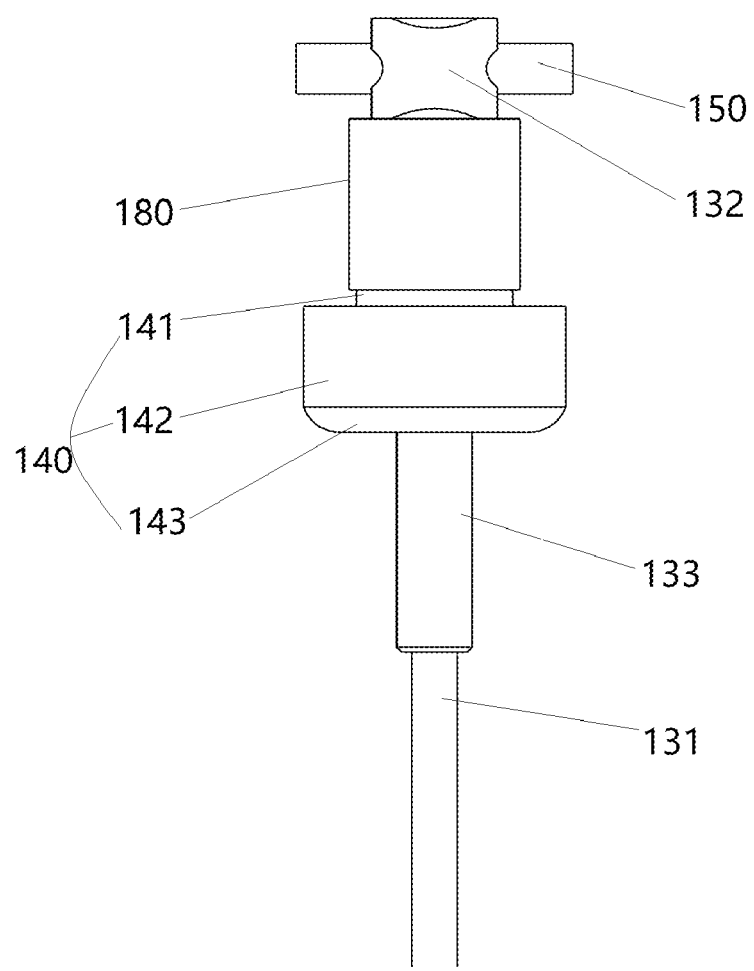
FIG. 8 shows a side view of a slider according to some embodiments of the present disclosure.

In some embodiments, as shown in FIG. 3, the drive part 130 further comprises a slider 132. The drive part connecting pin 150 may be fixedly arranged at a distal end of the slider 132. The distal end of the drive wire 131 is connected to a proximal end of the slider 132. The slider 132 is slidably arranged in the inner cavity 1121 of the support part 110, and the drive wire 131 is configured to drive the slider 132 to reciprocate in the support part 110. FIG. 8 shows a side view of a slider 132 according to some embodiments of the present disclosure. As shown in FIGS. 3 and 8, the sealing member 140 may be sleeved over an outer peripheral surface of the slider 132 or an outer peripheral surface of the proximal end part of the slider 132 in a sealed and enclosed manner at the first end, and the sealing member 140 may enclose an end portion of the proximal end of the support part 110 in a sealed manner at the second end. In some embodiments, the sealing member 140 may alternatively be configured to be attached to an inner wall of the proximal end of the support part 110 in a sealed manner at the second end. With the sealing member 140, the distal end part of the drive part 130 may be sealed relative to the hollow slideway 1123 of the support part 110. In some embodiments, the slider 132 may be of a structure in a cylindrical shape, a cube shape, a polyhedral shape or a special shape, and the drive part connecting pin 150 may be fixedly arranged at the distal end of a sliding block in a radial direction of the sliding block, or there may be two drive part connecting pins 150, which are relatively fixedly arranged at the distal end of the sliding block in a radial direction, respectively. In some embodiments, as shown in FIG. 8, a ferrule 180 may be arranged on the outer periphery of the first end of the sealing member 140 to secure the first end of the sealing member 140 to the proximal end of the slider 132.

Figure 10:
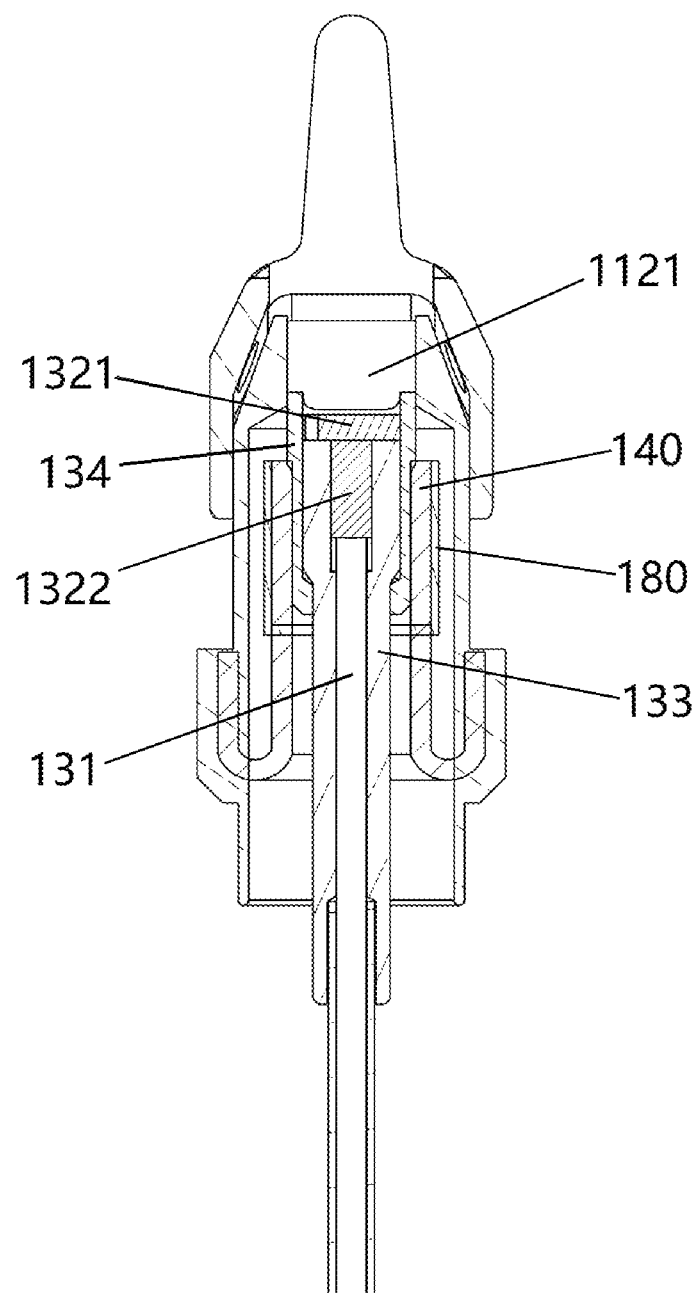
FIG. 10 shows a sectional view of two jaws in an open state according to some embodiments of the present disclosure.

FIG. 10 shows a sectional view of two jaws in an open state according to some embodiments of the present disclosure. As shown in FIG. 10, the slider 132 may comprise a radially-extending pin connecting part 1321 and a slide bar 1322 extending axially from the pin connecting part 1321 to the proximal side. The pin connecting part 1321 and the slide bar 1322 may be integrally formed with each other, or may be separate from and fixedly connected to each other, for example, by means of welding, bonding, or integral molding. The drive part connecting pin 150 is fixedly arranged on the pin connecting part 1321. In some embodiments, as shown in FIG. 10, a sealing sleeve 133 may also be sleeved over outer peripheries of the slide bar 1322 and the drive wire 131. As shown in FIG. 10, an outer distal end of the sealing sleeve 133 may also be sleeved into a sliding sleeve 134. In some embodiments, instead of the pin connecting part 1321, a radially-extending drive part connecting pin 150 may be arranged on the sliding sleeve 134. In some embodiments, the sliding sleeve 134 may be integrally molded with or fixedly connected to the pin connecting part 1321. The sealing member 140 may be sleeved over an outer peripheral surface of the sliding sleeve 134 in a sealed manner at the first end, and the sealing member 140 may enclose an end portion of the proximal end of the support part 110 in a sealed manner at the second end, so that the distal end of the drive part 130 and the head part 120 are sealed relative to the hollow slideway 1123 of the support part 110. Although in the above embodiments, the drive part 130 may comprise the slider 132, the drive wire 131, the sealing sleeve 133, and the sliding sleeve 134, it should be understood that the drive part 130 may be wholly or at least partially integrally molded. In some embodiments, the sealing sleeve 133 and the slide bar 1322 may be insulators of rubber, plastic, ceramic, etc., so as to avoid the surgical from being energized which results in burning the patient during a surgical operation.

Figure 9:
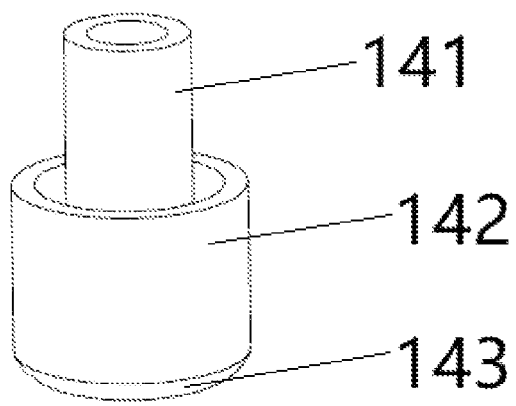
FIG. 9 shows a perspective view of a sealing member according to some embodiments of the present disclosure.

FIG. 9 shows a perspective view of a sealing member 140 according to some embodiments of the present disclosure. As shown in FIGS. 8 and 9, the sealing member 140 may comprise an inner tubular portion 141, an outer tubular portion 142, and a curved transition portion 143. The inner tubular portion 141 may be sleeved over an outer peripheral surface of the proximal end of the slider 132 (e.g., of the sliding sleeve 134, the sealing sleeve 133, or the slide bar 1322) and located in the inner cavity 1121 of the support part 110, and the inner tubular portion 141 can be driven by the slider 132 to axially move along the inner cavity 1121. An inner wall of the outer tubular portion 142 can be attached around an outer peripheral surface of the proximal end of the support part 110 in a sealed manner. However, it should be understood that an outer wall of the outer tubular portion 142 may be attached to an inner peripheral surface of the proximal end of the support part 110 in a sealed manner. The outer tubular portion 142 is integrally connected to the inner tubular portion 141 via the curved transition portion 143. Thus, with the sealing member 140, it is possible to seal the distal end of slider 132, the head part 120 and the drive wire 131 relative to the distal side of the sealing member 140, so that the drive wire 131 is isolated from a surgical interface, and body fluids from the patient, bacteria from the outside world, etc. are prevented from penetrating into the interior of the surgical effector through pores during the surgical operation. The slider and the drive wire can form an integral sealed structure by arranging the deformable sealing member. Therefore, during cleaning and disinfection, it is possible that the surgical effector is not disassembled, and only surfaces of the jaws are cleaned, thereby facilitating cleaning, and reducing or avoiding secondary infection.

In some embodiments, as shown in FIG. 10, a ferrule 180 may be sleeved outside the inner tubular portion 141 of the sealing member 140 so that the sealing member 140 is connected to the slider 132 in a sealed and secured manner. The provision of the ferrule 180 can further ensure a sealing performance between the sealing member 140 and the drive wire 131. The risk of the sealing member 140 slipping off during expanding and retracting movements is reduced.

In some embodiments, as shown in FIGS. 1 and 2, a protective sleeve 170 may also be arranged on the outer periphery of the proximal end of the support part 110. The protective sleeve 170 may comprise a proximal segment 171 and a distal segment 172. The distal segment 172 has a radial dimension greater than that of the proximal segment 171. The distal segment 172 of the protective sleeve 170 may comprise a receiving groove at the distal end thereof. The receiving groove of the protective sleeve 170 receives the proximal end of the support part 110 and forms a sealing with an end portion of the support part 110, and the proximal segment 171 of the protective sleeve 170 receives the drive wire 131. A through hole for the drive wire 131 to pass through may be formed at an end portion of the proximal segment 171 of the protective sleeve 170. In some embodiments, the protective sleeve 170 may be an insulator of rubber, plastic, ceramic, etc. The protective sleeve 170 can avoid the surgical effector from being energized which results in burning the patient during a surgical operation. In some embodiments, the protective sleeve 170 can insulate the surgical effector from an arm of a surgical tool, and can prevent contaminants from entering the interior of the surgical tool, which makes cleaning difficult.

Figure 11:
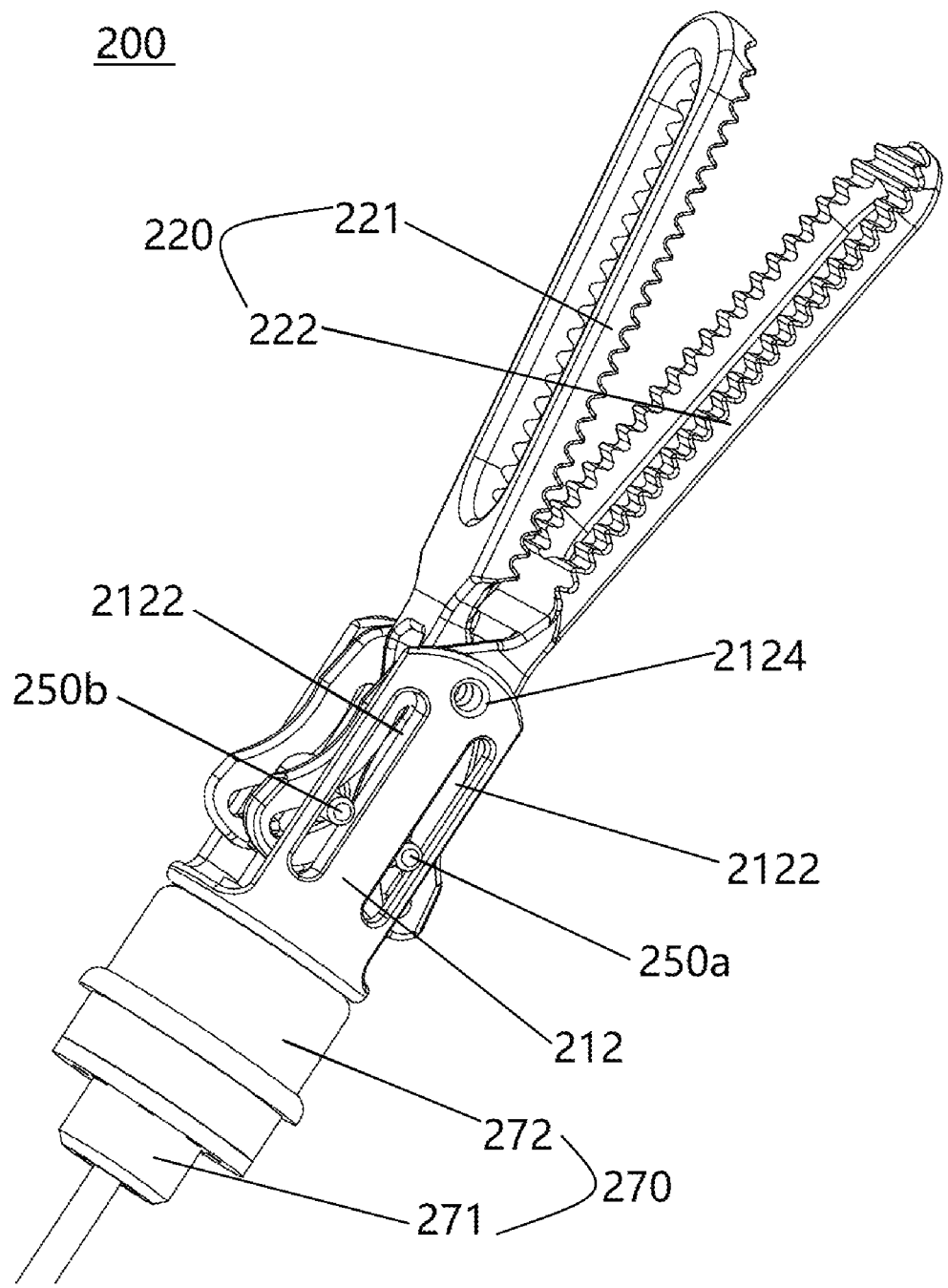
FIG. 11 shows a perspective view of a surgical effector according to some embodiments of the present disclosure.
Figure 12:
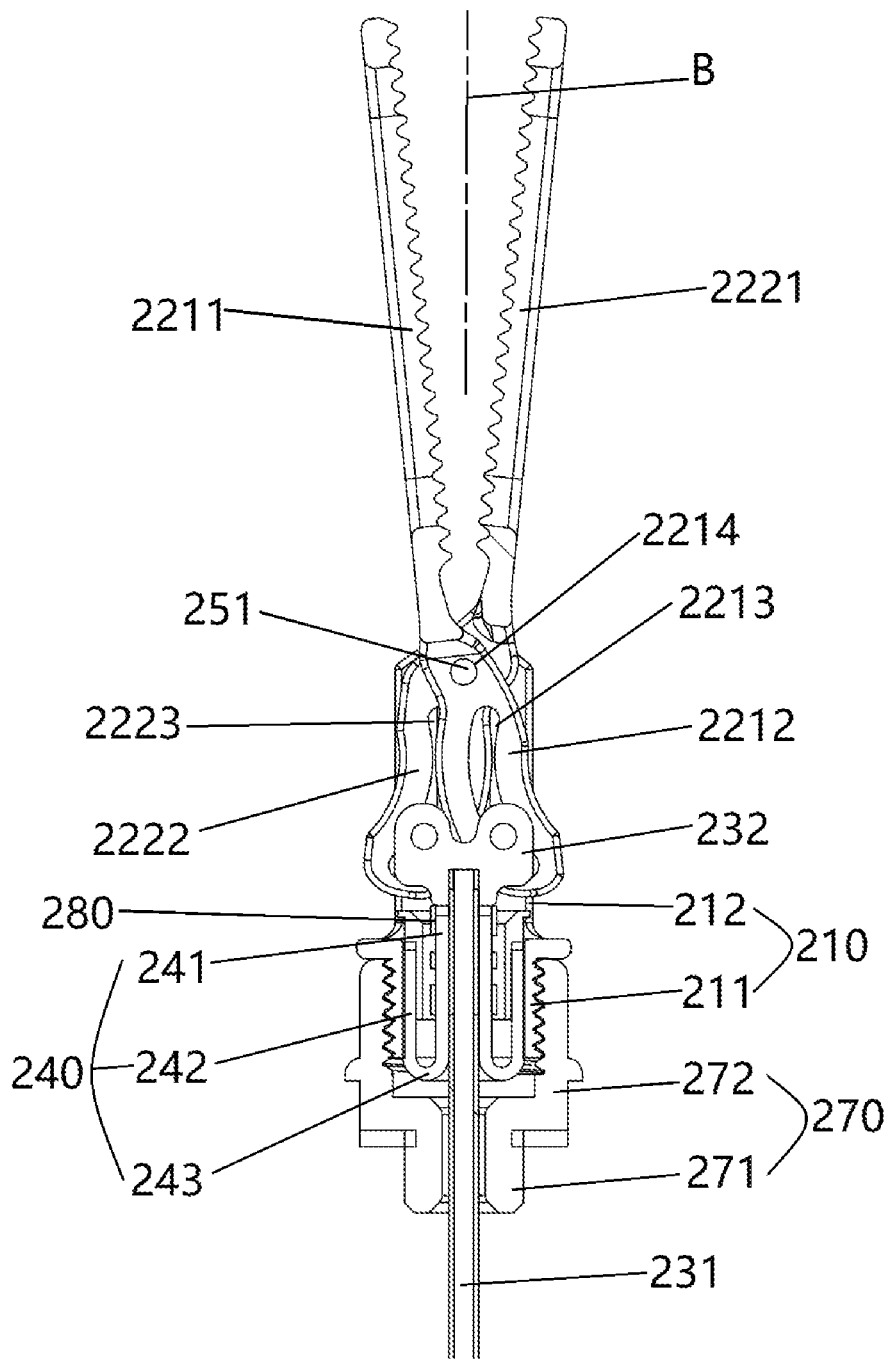
FIG. 12 shows a sectional view of a surgical effector according to some embodiments of the present disclosure.
Figure 13:
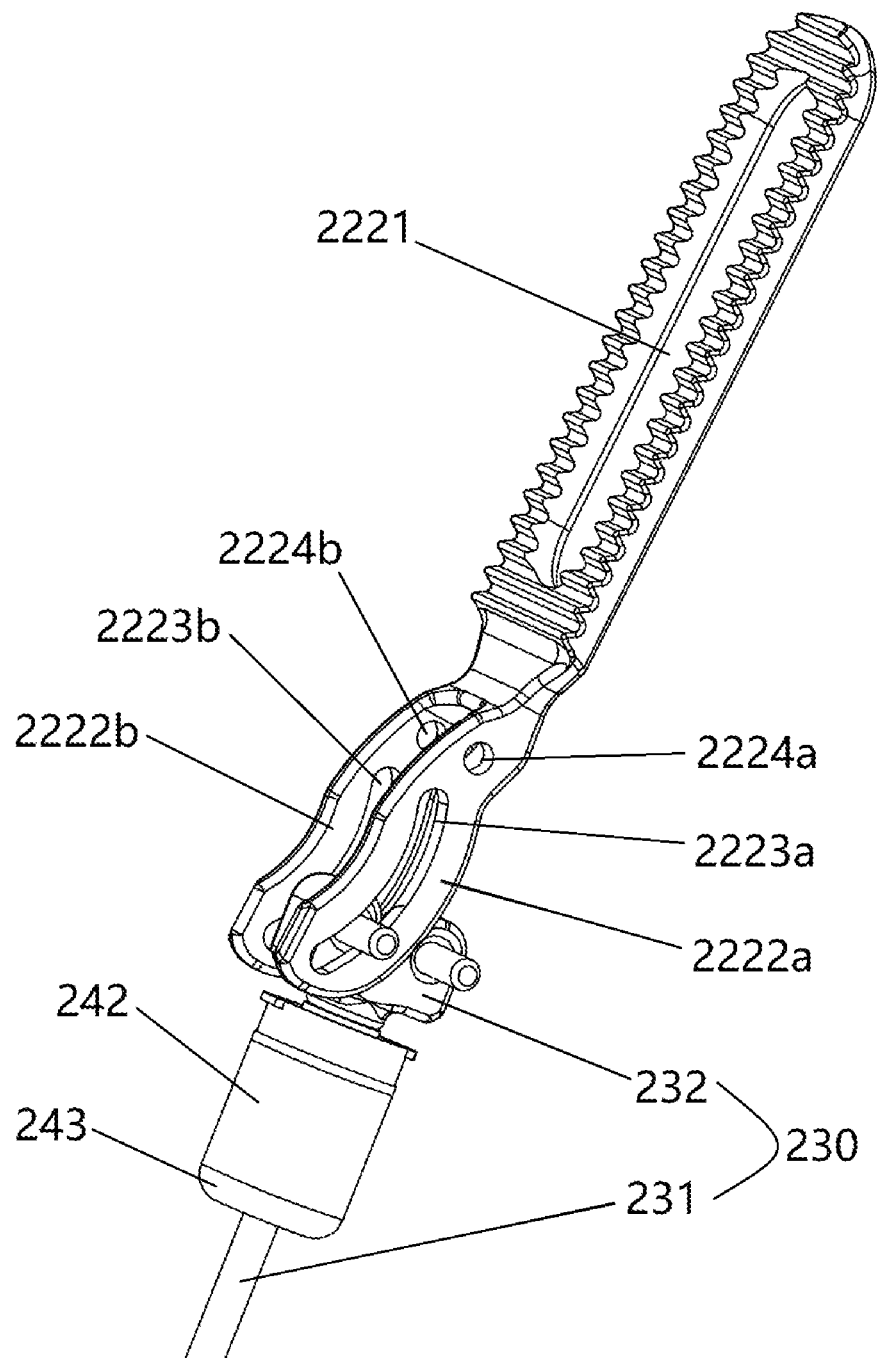
FIG. 13 shows a perspective view of a partial structure of a surgical effector according to some embodiments of the present disclosure.

FIGS. 11, 12 and 13 respectively show a perspective view, a sectional view, and a partial perspective structural view of a surgical effector 200 according to some embodiments of the present disclosure.

In some embodiments, the surgical effector 200 may comprise a head part 220, a support part 210, a drive part 230, and a sealing member 240.

As shown in FIGS. 11 and 13, the head part 220 is at least partially movably arranged at a distal end of the support part 210. The support part 210 may comprise an inner cavity (not shown in the figures), the drive part 230 is slidably arranged in the inner cavity of the support part 210 and is connected to a proximal end of the head part 220, so that at least a part of the head part 220 is driven to move relative to the distal end of the support part 210 by the movement of the drive part inside the support part 210.

The sealing member 240 may be connected to an outer peripheral surface of the drive part 230 in a sealed manner at a first end (e.g., a proximal end, or a distal end shown in FIG. 12) thereof and be connected to an inner peripheral surface of the proximal end of the support part 210 in a sealed manner at a second end (e.g., a distal end, or a proximal end shown in FIG. 12) thereof, and at least a part of the sealing member 240 is deformable. Therefore, when the drive part 230 is relatively moved in the support part 210, the sealing member 240 can be deformed adaptively. The sealing member 240 can form a sealed isolation between the drive part 230, the support part 210 and the head part 220, so as to prevent patient's body fluids, bacteria and viruses from entering the interior of the surgical effector 200 through pores during a surgical operation, thereby facilitating repeated cleaning and disinfection of the surgical effector 200.

In some embodiments, the support part 210 may comprise at least one pair of support part slide slots 2122. As shown in FIG. 11, the support part 210 may comprise two pairs of support part slide slots 2122 The two pairs of support part slide slots 2122 may be two pairs of axial slide slots radially opposed to each other and extending axially. In some embodiments, as shown in FIG. 11, the support part 210 may comprise a support connector 211 at the proximal end and a pair of support members 212 arranged circumferentially spaced apart from each other at the distal end of the support connector 211. The support connector 211 may be tubular, and its cross section may be circular, oval, rectangular, polygonal, etc. An axially-arranged hollow slideway is formed in the support connector (not shown in the figures). The two pairs of support part slide slots 2122 may be oppositely and symmetrically formed in the support members 212, respectively. The support members 212 may be fixedly connected to or integrally molded with the support connector 211. In some embodiments, the support members 212 of the support part 210 may be tubular or partially tubular, and their cross sections may be circular, oval, rectangular, polygonal, etc.

In some embodiments, as shown in FIGS. 11 to 12, the head part 220 may comprise a first head member 221 and a second head member 222 capable of mating with the first head member 221. The first head member 221 and the second head member 222 may be respectively rotatably connected to the support part 210, for example, by means of hinging.

In some embodiments, as shown in FIG. 13, the second head member 222 may comprise a jaw 2221 and a pair of jaw support members 2222a-b. The pair of jaw support members 2222a-b may be symmetrically arranged on two sides of a proximal end of the jaw 2221. The jaw support members 2222a-b are oppositely provided with connecting holes 2224a-b at the distal ends respectively, the jaw support members 2222a-b may respectively comprise jaw slide slots 2223a-b, and the jaw slide slots 2223a-b are arranged opposite each other in the jaw support members 2222a-b. The jaw slide slots 2223a-b may be arc-shaped slide slots.

As shown in FIG. 12, the first head member 221 may have the similar structure as the second head member 222. The first head member 221 may comprise a jaw 2211 and a pair of jaw support members 2212. The pair of jaw support members 2212 may be symmetrically arranged on two sides of a proximal end of the jaw 2211. A spacing between the pair of jaw support members 2212 may be greater or less than a spacing between the pair of jaw support members 2222a-b to facilitate rotational hinging between the jaw support members 2212 and the jaw support members 2222a-b. A pair of connecting holes 2214 may be respectively oppositely formed at the distal ends of the pair of jaw support members 2212, and the pair of jaw support members 2212 may respectively comprise jaw slide slots 2213. In some embodiments, as shown in FIG. 12, the jaw slide slots 2213 may be arc-shaped slide slots, and a pair of jaw slide slots 2213 may be arranged opposite each other in the pair of jaw support members 2212. The connecting holes 2214 and 2224a-b may be used for mounting of the first head member 221 and the second head member 222, respectively, as will be described in detail below.

In some embodiments, the drive part 230 comprises a drive wire 231, as shown in FIG. 13.

In some embodiments, as shown in FIG. 11, the pair of jaw support members 2222a-b of the second head member 222 may be arranged inside a pair of support members 212 of the support part 210, and the pair of jaw support members 2212 of the first head member 221 may be arranged inside the jaw support members 2222a-b. It should be understood that the pair of jaw support members 2222a-b of the second head member 122 may alternatively be arranged inside the pair of jaw support members 2212 of the first head member 221. As shown in FIGS. 11 and 12, the jaw 2211 of the first head member 221 and most of the jaw support members 2222a-b of the second head member 222 may be located on one side of a center line B of the support members 212; and most of the pair of jaw support members 2212 of the first head member 221 and the jaw 2221 of the second head member 222 may be located on the other side opposite to the one side of the centerline B.

As shown in FIG. 11, a pair of drive part connecting pins 250a-b may be slidably arranged in two pairs of support part slide slots 2122 located on the one side and the other side of the center line B (referring to FIG. 12) of the support members 212, respectively. As shown in FIG. 12, the drive part connecting pin 250b may also be slidably arranged in the pair of jaw slide slots 2223a-b of the second head member 222, and the drive part connecting pin 250a may also be slidably arranged in the pair of jaw slide slots 2213 of the first head member 221. The pair of connecting holes 2214 of the first head member 221 and the pair of connecting holes 2224a-b of the second head member 222 are aligned with each other, and a pivotal connecting pin 251 may pass through the pair of connecting holes 2214 and the pair of connecting holes 2224a-b in a radial direction (as shown in FIGS. 12 and 13), and has two ends which can be pivotally connected to a pair of support part connecting holes 2124 on the support part 210, respectively, so that the first head member 221 and the second head member 222 are respectively hinged to the support part 210. The drive part connecting pins 250a-b may be connected to the distal end of the drive wire 231. When the drive wire 231 is pushed and/or pulled to relatively move in the hollow slideway of the support part 210, the drive part connecting pin 250b can be driven to slide back and forth along the jaw slide slots 2223a-b and one pair of support part slide slots 2122, and the drive part connecting pin 250a can be driven to slide back and forth along the pair of jaw slide slots 2213 and the other pair of support part slide slots 2122, thereby driving the first head member 221 and the second head member 222 to be opened and closed relative to each other.

In some embodiments, as shown in FIGS. 12 and 13, the drive part 230 may further comprise a slider 232. The pair of drive part connecting pins 250a-b may be respectively fixedly arranged at a distal end of the slider 232. The distal end of the drive wire 231 is connected to a proximal end of the slider 232. The slider 232 is slidably arranged in the inner cavity of the support part 210, and the drive wire 231 is configured to drive the slider 232 to reciprocate in the support part 210.

As shown in FIG. 12, the sealing member 240 may be sleeved over an outer peripheral surface of the slider 232 or an outer peripheral surface of the proximal end part of the slider 232 or the outer periphery of the distal end of the drive wire 231 in a sealed manner at the first end thereof, and the sealing member 240 may be attached to an inner peripheral surface of the proximal end of the support part 210 in a sealed manner at the second end thereof, or is attached around the outer periphery of the proximal end of the support part 210 in a sealed manner at the second end. With the sealing member 240, the distal end part of the drive part 230 may be sealed relative to the hollow slideway of the support part 210. In some embodiments, the slider 232 may be of a structure in a cylindrical shape, a cube shape, a polyhedron shape or a special shape. The pair of drive part connecting pins 250a-b may be fixedly arranged at the distal end of the slider 232 in a transverse direction of the slider 232. In some embodiments, as shown in FIG. 12, a ferrule 280 may be arranged on the outer periphery of the first end of the sealing member 240 to secure the first end of the sealing member 240 to the proximal end of the slider 232. In some embodiments, a ferrule may also be arranged on the outer periphery of the second end of the sealing member 240 to secure the second end of the sealing member 240 to the support part 210.

As shown in FIG. 12, the sealing member 240 may comprise an inner tubular portion 241, an outer tubular portion 242, and a curved transition portion 243. The inner tubular portion 241 may be sleeved over an outer peripheral surface of the proximal end of the slider 232 and located in the inner cavity of the support part 210, and the inner tubular portion 241 can be driven by the slider 232 to axially move along the inner cavity. An outer wall of the outer tubular portion 242 can be attached to an inner peripheral surface of the proximal end of the support part 210 in a sealed manner. However, it should be understood that an inner wall of the outer tubular portion 242 can be attached around an outer peripheral surface of the proximal end of the support part 210 in a sealed manner. The outer tubular portion 242 is integrally connected to the inner tubular portion 241 via the curved transition portion 243. Thus, with the sealing member 240, it is possible to seal the distal end of slider 232, the head part 220 and the drive wire 231 relative to the distal side of the sealing member 240, so that the drive wire 231 is isolated from a surgical interface, and body fluids from the patient, bacteria from the outside world, etc. are prevented from penetrating into the interior of the surgical effector through pores during the surgical operation. Therefore, during cleaning and disinfection, it is possible that the surgical effector is not disassembled, and only surfaces of the jaws are cleaned, thereby facilitating cleaning, and reducing or avoiding secondary infection.

In some embodiments, as shown in FIG. 12, a protective sleeve 270 may also be arranged on the outer periphery of the proximal end of the support part 210. The protective sleeve 270 may comprise a proximal segment 271 and a distal segment 272. The distal segment 272 has a radial dimension greater than that of the proximal segment 271. The distal segment 272 of the protective sleeve 270 may comprise a receiving groove at the distal end (not shown in the figure). The receiving groove of the protective sleeve 270 receives the proximal end of the support part 210, for example, the support connector 211, and forms a sealing with an end portion of the support part 210. Those skilled in the art should understand that the distal segment 272 and the support connector 211 at the proximal end of the support part 210 may be in threaded connection, in interference-fit connection, welded, bonded, integral molded, etc. The proximal segment 271 of the protective sleeve 270 receives the drive wire 231. A through hole for the drive wire 231 to pass through may be formed at an end portion of the proximal segment 271 of the protective sleeve 270. The protective sleeve 270 can insulate the surgical effector from an arm of a surgical tool, and can prevent contaminants from entering the interior of the surgical tool, which makes cleaning difficult.

Figure 14:
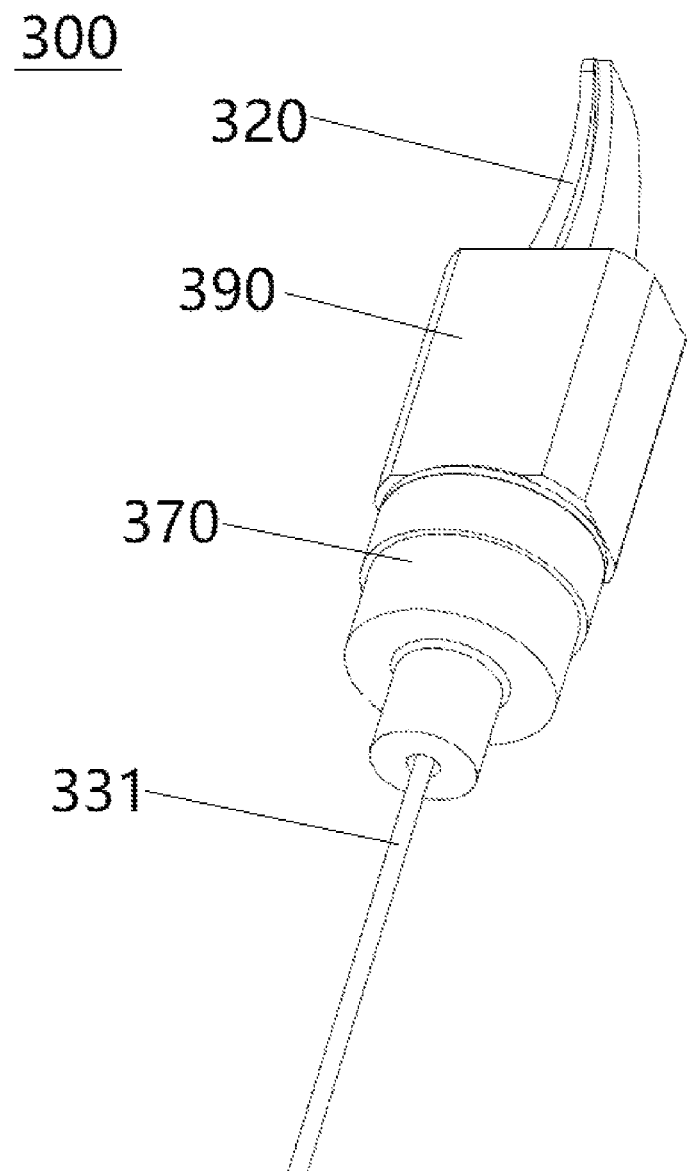
FIG. 14 shows a perspective view of a surgical effector according to some embodiments of the present disclosure.
Figure 15:
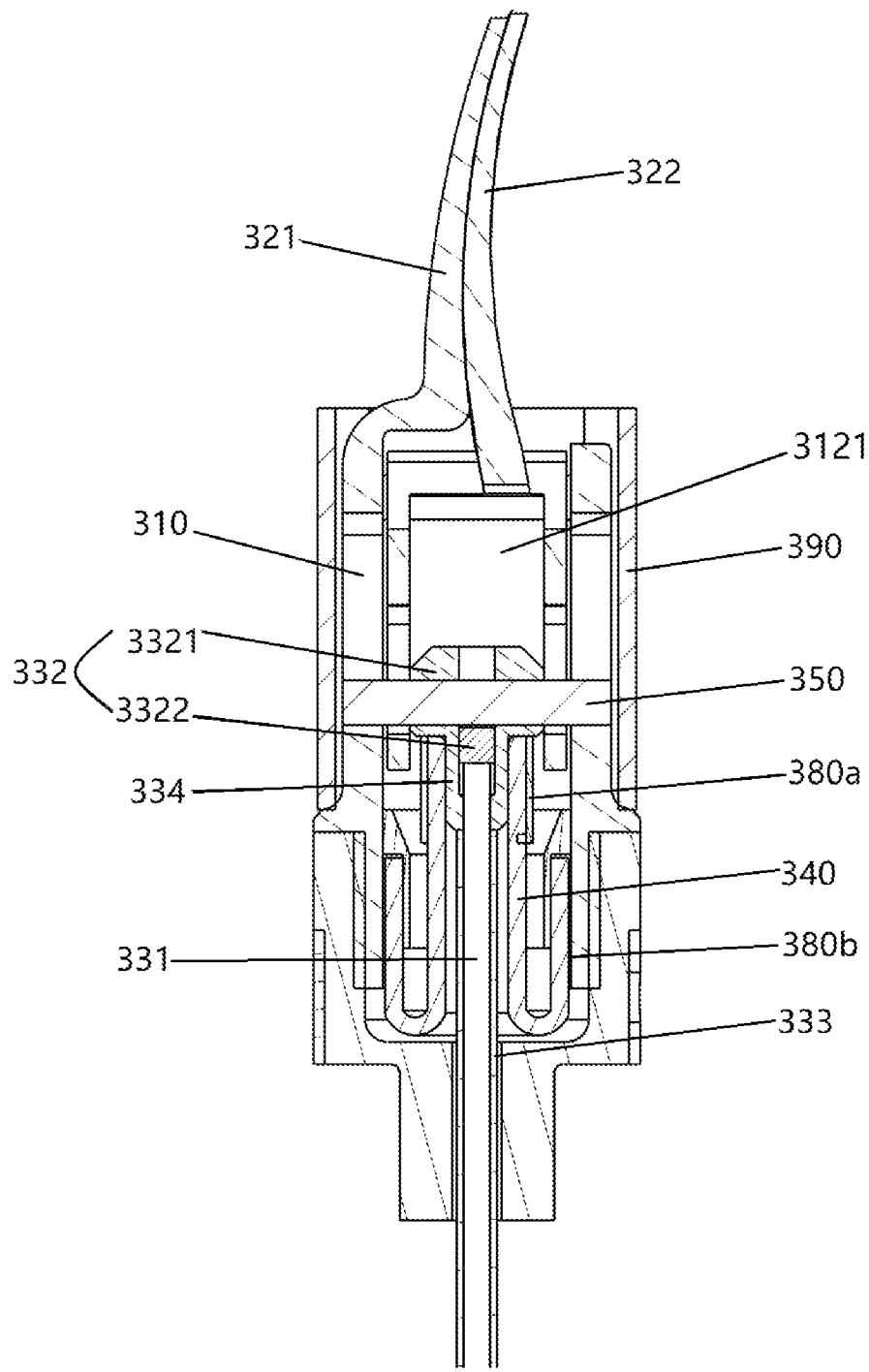
FIG. 15 shows a sectional view of a surgical effector according to some embodiments of the present disclosure.
Figure 16:
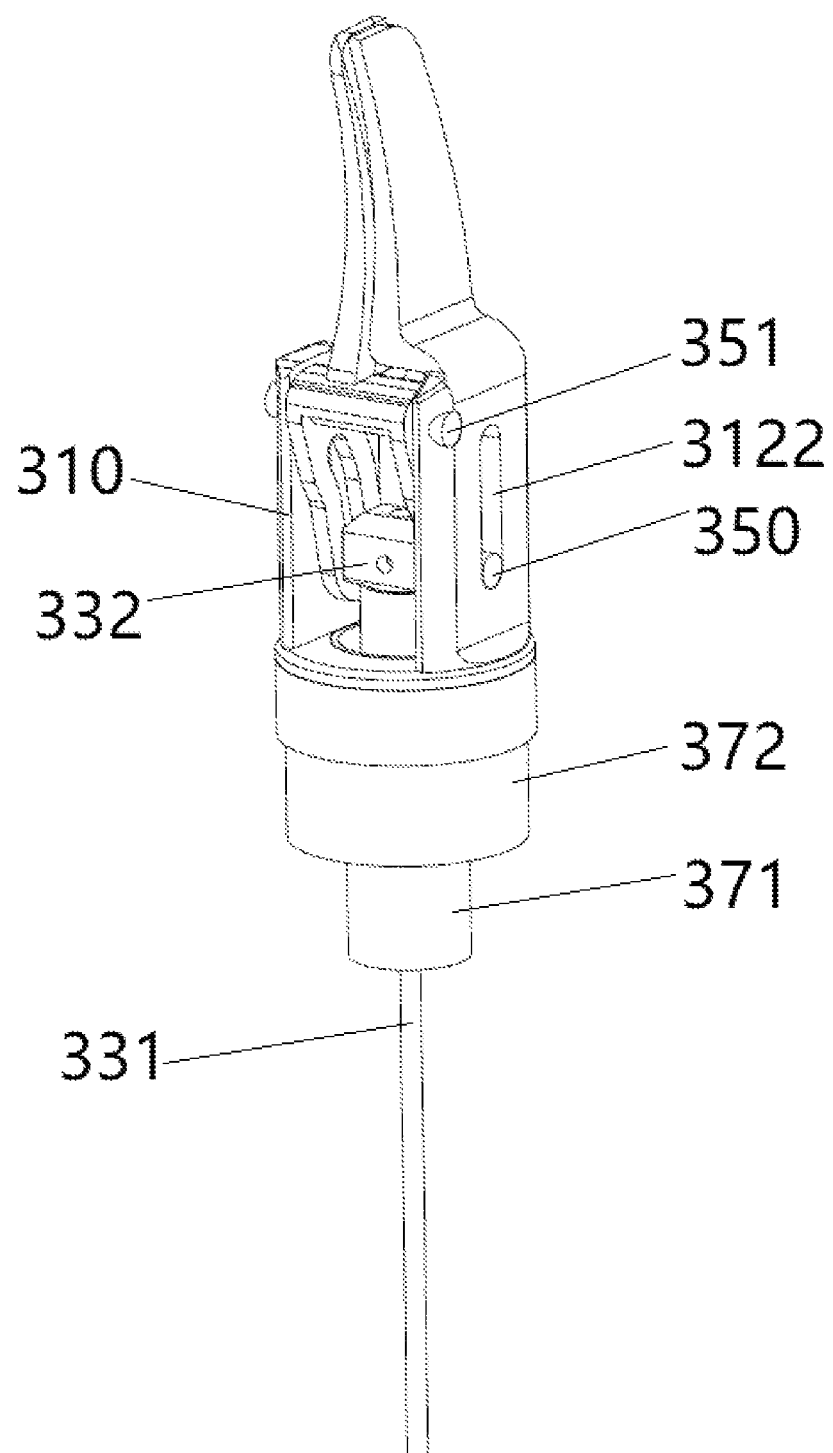
FIG. 16 shows a perspective view of a partial structure of a surgical effector according to some embodiments of the present disclosure.

FIGS. 14, 15 and 16 respectively show a perspective view, a sectional view, and a partial perspective structural view of a surgical effector 300 according to some embodiments of the present disclosure.

In some embodiments, the surgical effector 300 may comprise a head part 320, a support part 310, a drive part 330 (referring to FIG. 18), and a sealing member 340.

As shown in FIGS. 14 and 15, the head part 320 is at least partially movably arranged at a distal end of the support part 310. The support part 310 may comprise an inner cavity 3121, the drive part 330 (referring to FIG. 18) may be slidably arranged in the inner cavity 3121 of the support part 310 and is connected to a proximal end of the head part 320, so that at least a part of the head part 320 is driven to move relative to the distal end of the support part 310 by the movement of the drive part inside the support part 310.

The sealing member 340 may have a first end (e.g., a proximal end, or a distal end shown in FIG. 15) connected to the drive part 330 (referring to FIG. 18) in a sealed manner and a second end (e.g., a distal end, or a proximal end shown in FIG. 15) connected to the support part 310 in a sealed manner, and at least a part of the sealing member 340 is deformable. Therefore, when the drive part 330 is relatively moved in the support part 310, the sealing member 340 can be deformed adaptively. The sealing member 340 can form a sealed isolation between the drive part 330, the support part 310 and the head part 320, so as to prevent patient's body fluids, bacteria and viruses from entering the interior of the surgical effector 300 through pores during a surgical operation, thereby facilitating repeated cleaning and disinfection of the surgical effector 300.

Figure 19:
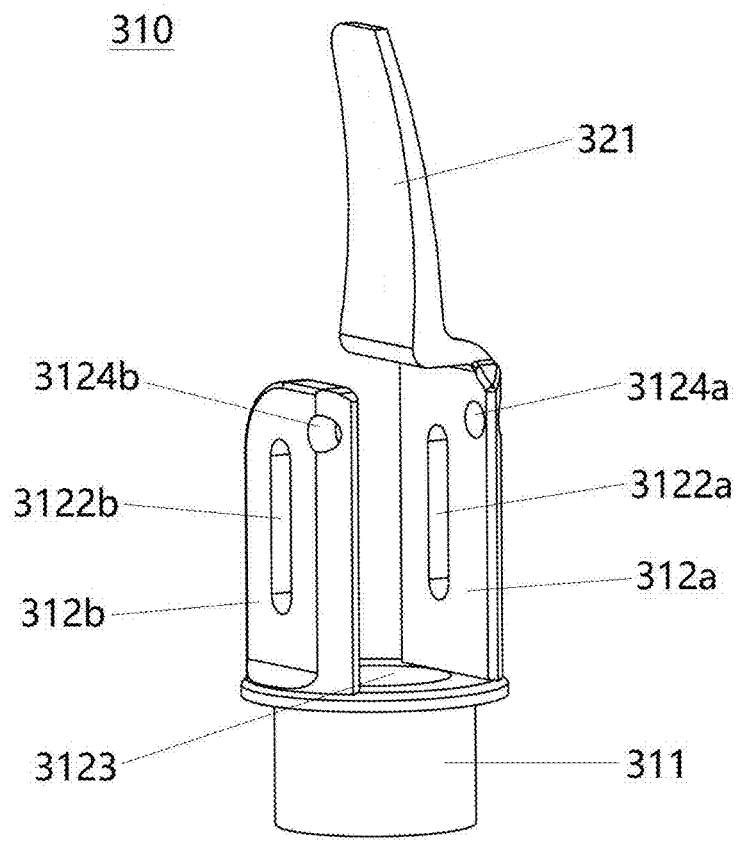
FIG. 19 shows a perspective view of a support part according to some embodiments of the present disclosure.

In some embodiments, the support part 310 may comprise at least one pair of support part slide slots. FIG. 19 shows a perspective view of a support part 310 according to some embodiments of the present disclosure. As shown in FIG. 19, the support part 310 may comprise a pair of support part slide slots 3122*a-b*. The support part slide slots 3122*a-b* may be a pair of axial slide slots radially opposed to each other and extending axially.

In some embodiments, as shown in FIG. 19, the support part 310 may comprise a support connector 311 at the proximal end and a pair of support members 312*a-b* arranged circumferentially spaced apart from each other at the distal end of the support connector 311. The support connector 311 may be tubular, and its cross section may be circular, oval, rectangular, polygonal, etc. An axially-arranged hollow slideway 3123 is formed in the support connector. The support part slide slots 3122*a-b* may be oppositely and symmetrically formed in the support members 312*a-b*, respectively. The support members 312 may be fixedly connected to or integrally molded with the support connector 311. In some embodiments, the support members 312 of the support part 310 may be tubular or partially tubular, and their cross sections may be circular, oval, rectangular, polygonal, etc.

As shown in FIG. 15, the head part 320 may comprise a first head member 321 and a second head member 322 capable of mating with the first head member 321. In some embodiments, the first head member 321 may be fixedly arranged at the distal end of the support part 310, for example, by means of welding, bonding or integral molding. The second head member 322 may be rotatably connected to the first head member 321 or the support part 310, for example, by means of hinging. As shown in FIG. 19, the first head member 321 may be integrally molded with or fixedly connected to one of the support member 312*a* and the support member 312*b* of the support part 310. It should be understood that the first head member 321 may alternatively be integrally molded with or fixedly connected to the pair of support members 312*a-b*.

Figure 17:
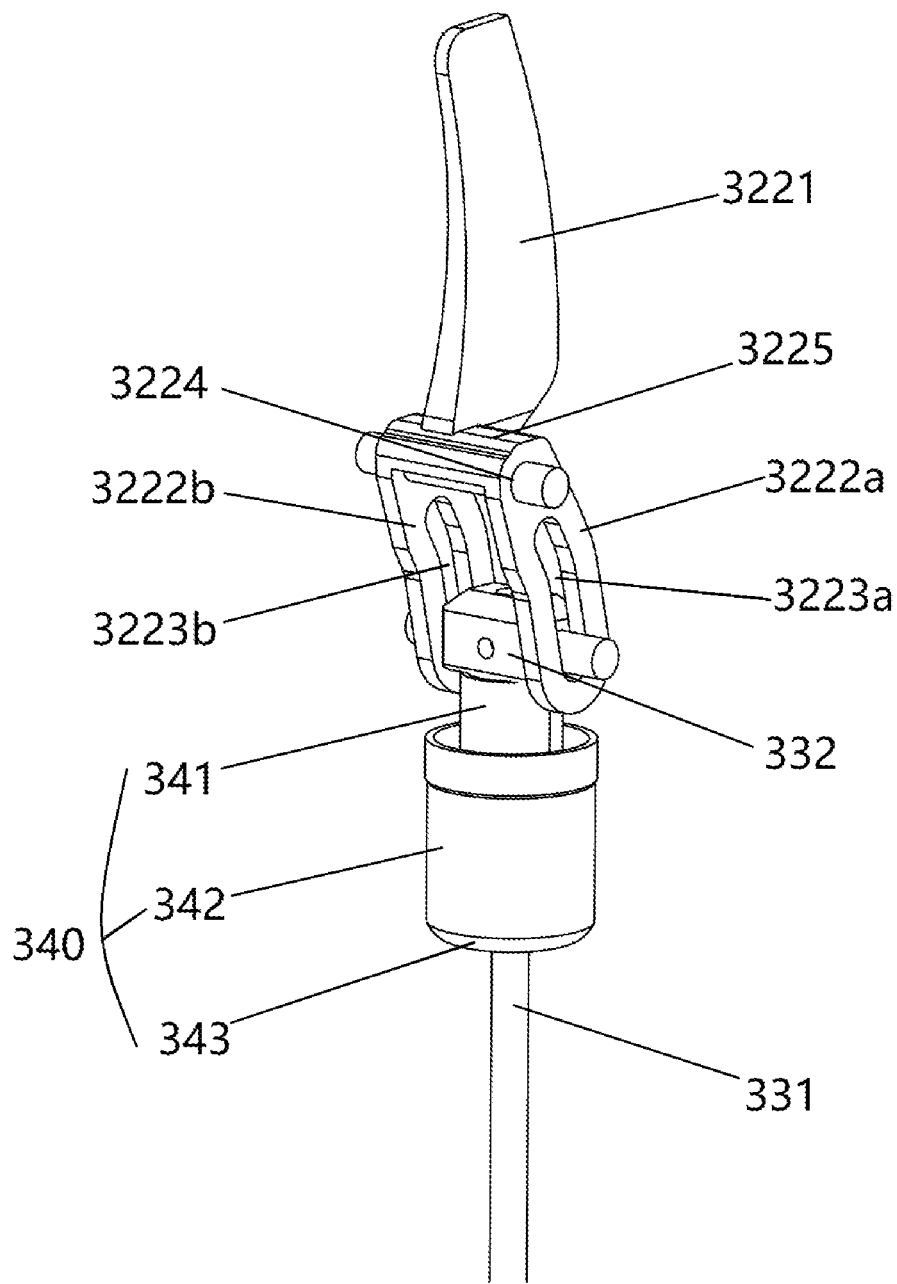
FIG. 17 shows a perspective view of a head part and a drive part cooperating with each other according to some embodiments of the present disclosure.

FIG. 17 shows a perspective view of a head part 320 and a drive part 330 cooperating with each other according to some embodiments of the present disclosure. As shown in FIG. 17, the second head member 322 may comprise a jaw 3221, a jaw connector 3225, and a pair of jaw support members 3222*a* and 3222*b*. The jaw connector 3225 may be integrally molded or fixedly connected at a proximal end of the jaw 3221. The pair of jaw support members 3222*a-b* may be symmetrically arranged on two sides of a proximal end of the jaw connector 3225. The jaw 3221, the jaw connector 3225, and the pair of the jaw support members 3222*a-b* may be integrally molded or partially integrally molded or fixedly connected. The jaw connector 3225 may be respectively provided with a pair of connecting holes 3224 opposed to each other. As shown in FIG. 17, the jaw support members 3222*a-b* may comprise jaw slide slots 3223*a-b*, respectively. In some embodiments, the jaw slide slots 3223*a-b* may be arc-shaped slide slots, and the jaw slide slots 3223*a-b* are arranged opposite each other on the jaw support members 3222*a-b*.

In some embodiments, the drive part 330 comprises a drive wire 331, as shown in FIGS. 14 to 18.

In some embodiments, the jaw support members 3222*a-b* may also be arranged inside the support part 310. As shown in FIGS. 15 and 16, a drive part connecting pin 350 may be slidably arranged in the support part slide slots 3122*a-b* (as shown in FIG. 19) and the jaw slide slots 3223*a-b* (as shown in FIG. 17). A pivotal connecting pin 351 passes through a pair of connecting holes 3224 (as shown in FIG. 17), and two ends of the pivotal connecting pin are respectively pivotally connected to the pair of support part connecting holes 3124*a-b* (referring to FIG. 19) of the support part 310, so that the second head member 322 is hinged to the support part 310. The drive part connecting pin 350 is connected to a distal end of the drive wire 331. When the drive wire 331 is pushed and/or pulled to relatively move in the hollow slideway 3123 of the support part 310, the drive part connecting pin 350 is driven to slide back and forth along the jaw slide slots 3223*a-b* and the support part slide slots 3122*a-b*, thereby driving the second head member 322 to be opened and closed relative to the first head member 321.

Figure 18:
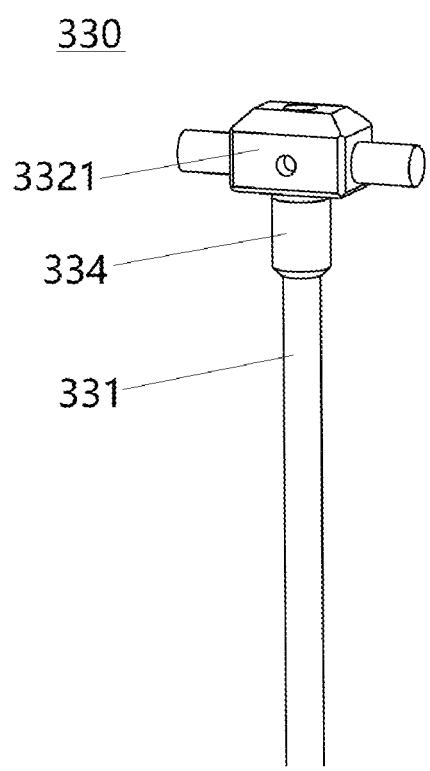
FIG. 18 shows a schematic structural view of a drive part according to some embodiments of the present disclosure.

FIG. 18 shows a schematic structural view of a drive part 330 according to some embodiments of the present disclosure. In some embodiments, as shown in FIGS. 15 and 18, the drive part 330 further comprises a slider 332. The drive part connecting pin 350 may be fixedly arranged at a distal end of the slider 332. The distal end of the drive wire 331 is connected to a proximal end of the slider 332. The slider 332 is slidably arranged in the inner cavity 3121 of the support part 310, and the drive wire 331 is configured to drive the slider 332 to reciprocate in the support part 310. As shown in FIGS. 15 and 17, the sealing member 340 may be sleeved over an outer peripheral surface of the slider 332 or an outer peripheral surface of the proximal end part of the slider 332 in a sealed manner at the first end, and the sealing member 340 may also be configured to be attached to an inner wall of the proximal end of the support part 310 in a sealed manner at the second end. In some embodiments, the sealing member 340 may enclose an end portion of the proximal end of the support part 310, for example, an outer peripheral surface of the support connector 311, in a sealed manner at the second end. With the sealing member 340, the distal end part of the drive part 330 may be sealed relative to the hollow slideway 3123 of the support part 310. In some embodiments, the slider 332 may be of a structure in a cylindrical shape, a cube shape, a polyhedral shape or a special shape, and the drive part connecting pin 350 may be fixedly arranged at the distal end of the slider 332 in a radial direction of the slider 332.

As shown in FIG. 15, the slider 332 may comprise a radially-extending pin connecting part 3321 and a slide bar 3322 extending axially from the pin connecting part 3321 to the proximal side. The pin connecting part 3321 and the slide bar 3322 may be integrally formed, or may be separate from and fixedly connected to each other, for example, by means of welding or bonding. The drive part connecting pin 350 is fixedly arranged on the pin connecting part 3321. In some embodiments, as shown in FIGS. 15 and 18, a sliding sleeve 334 is sleeved over outer peripheries of the slide bar 3322 and the drive wire 331, the sliding sleeve 334 may be integrally molded with the pin connecting part 3321, and the pin connecting part 3321 is provided with the drive part connecting pin 350 extending radially. It should be understood that the sliding sleeve 334 and the pin connecting part 3321 may be separate from and fixedly connected to each other, for example, by means of welding or bonding. The sealing member 340 may be sleeved over an outer peripheral surface of the sliding sleeve 334 in a sealed manner at the first end, and the sealing member 340 may be attached to an inner peripheral surface of the proximal end of the support part 310 in a sealed manner at the second end, so that the distal end of the drive part 330 and the head part 320 are sealed relative to the hollow slideway 3123 of the support part 310. Although in the above embodiments, the drive part 330 may comprise the slider 332, the drive wire 331, and the sliding sleeve 334, it should be understood that the drive part 330 may be wholly or at least partially integrally molded.

In some embodiments, a proximal end of the drive wire 331 may be connected to a power supply apparatus (not shown in the figure) so that a conductive pathway is formed between the second head member 322 and the drive wire 331. In some embodiments, the slider 332, each of the drive part connecting pin 350, and the support members 312 may comprise a conductive material, for example, metal. Those skilled in the art should understand that the slider 332, the drive part connecting pin 350 and the support members 312 may alternatively be plated with a conductive layer on their surfaces to achieve a function of electric conduction. The proximal end of the drive wire 331 is connected to the power supply apparatus, a conductive pathway may be formed between the second head member 322 and the drive wire 331 by means of the slider 332, and the first head member 321 may be connected to this conductive pathway via the support members 312 and the drive part connecting pin 350. The conductive pathway can supply power to the first head member 321 and the second head member 322 to form a "monopolar" structure, so that operations such as electric shearing and electric cutting can be carried out.

In some embodiments, as shown in FIG. 15, the outer periphery of a part of the drive wire 331 located outside the proximal end of the slider 332 (e.g., the sliding sleeve 334 or the slide bar 3322) may be enclosed by an insulating protective sleeve 333, and the distal end of the drive wire 331 passes through the insulating protective sleeve 333 and is connected to the proximal end of the slider 332. The insulating protective sleeve 333 can prevent the external conduction of the proximal end of the surgical effector, which causing a safety hazard.

In some embodiments, the outer periphery of the pair of support members 312a-b of the support part 310 may be enclosed by an insulating cover 390 (referring to FIG. 14), and distal end parts of the first head member 321 and the second head member 322 may extend out of the insulating cover 390. The insulating cover 390 may be a tubular member, and its cross section may be circular, oval, rectangular, polygonal, etc. The insulating cover 390 may be an insulator of rubber, plastic, ceramic, etc. The insulating cover 390 can reduce the conductive area of the surgical effector, and can avoid forming conductive pathways between the surgical effector and body tissues other than a target tissue to burn the patient, which case results burning the patient.

As shown in FIG. 17, the sealing member 340 may comprise an inner tubular portion 341, an outer tubular portion 342, and a curved transition portion 343. The inner tubular portion 341 may be sleeved over an outer peripheral surface of the proximal end of the slider 332 (e.g., of the sliding sleeve 334, or the slide bar 3322) and located in the inner cavity 3121 of the support part 310, and the inner tubular portion 341 can be driven by the slider 332 to axially move along the inner cavity 3121. An outer wall of the outer tubular portion 342 can be attached to an inner peripheral surface of the proximal end of the support part 310 in a sealed manner. However, it should be understood that an inner wall of the outer tubular portion 342 can be attached around an outer peripheral surface of the proximal end of the support part 310 in a sealed manner. The outer tubular portion 342 is integrally connected to the inner tubular portion 341 via the curved transition portion 343. Thus, with the sealing member 340, it is possible to seal the distal end of slider 332, the head part 320 and the drive wire 331 relative to the distal side of the sealing member 340, so that the drive wire 331 is isolated from a surgical interface, and body fluids from the patient, bacteria from the outside world, etc. are prevented from penetrating into the interior of the surgical effector through pores during the surgical operation. Therefore, during cleaning and disinfection, it is possible that the surgical effector is not disassembled, and only surfaces of the jaws are cleaned, thereby facilitating cleaning, and reducing or avoiding secondary infection.

In some embodiments, as shown in FIG. 15, a ferrule 380a may be sleeved outside the inner tubular portion 341 of the sealing member 340 so that the sealing member 340 is connected to the slider 332 in a sealed and secured manner. In some embodiments, as shown in FIG. 15, a ferrule 380b may be sleeved outside the outer tubular portion 342 of the sealing member 340, and the ferrule 380b may be fixedly connected to the proximal end of the support part 310, so that the outer tubular portion 342 is connected to the support part 310 in a sealed and secured manner. With the arrangement of the ferrules 380a-b, the sealing performance between the sealing member 340 and the drive wire 331 as well as between the sealing member 340 and the support part 310 can be ensured respectively, and the risk of the sealing member 340 slipping off during expanding and retracting movements can be reduced.

Figure 20:
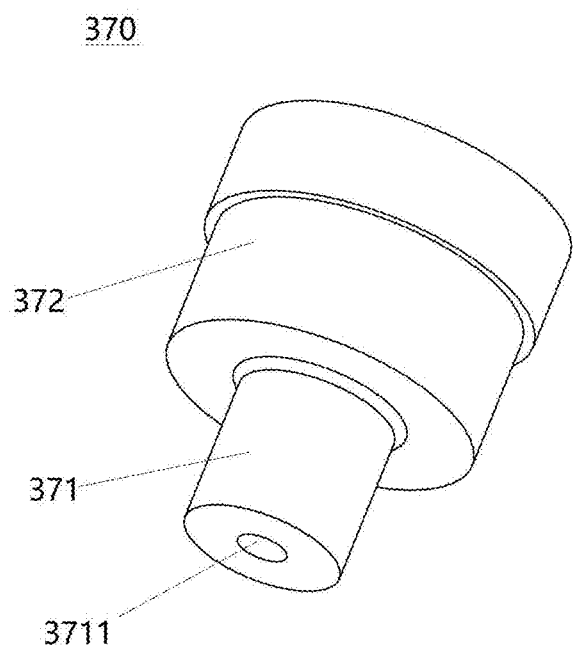
FIG. 20 shows a perspective view of a protective sleeve according to some embodiments of the present disclosure.

FIG. 20 shows a perspective view of a protective sleeve 370 according to some embodiments of the present disclosure. In some embodiments, a protective sleeve 370 may also be arranged on the outer periphery of the proximal end of the support part 310. As shown in FIGS. 16 and 20, the protective sleeve 370 may comprise a proximal segment 371 and a distal segment 372. The distal segment 372 has a radial dimension greater than that of the proximal segment 371. The distal segment 372 of the protective sleeve 370 may comprise a receiving groove at the distal end (not shown in the figure). The receiving groove of the protective sleeve 370 receives the proximal end of the support part 310 and forms a sealing with an end portion of the support part 310. Those skilled in the art should understand that the distal segment 372 and the proximal end of the support part 310 may be in threaded connection, in interference-fit connection, welded, bonded, integral molded, etc. The proximal segment 371 of the protective sleeve 370 receives the drive wire 331. A through hole 3711 for the drive wire 331 to pass through may be formed at an end portion of the proximal segment 371 of the protective sleeve 370. In some embodiments, the protective sleeve 370 may be an insulator of rubber, plastic, ceramic, etc. The protective sleeve 370 can insulate the surgical effector from an arm of a surgical tool, and can prevent contaminants from entering the interior of the surgical tool, which makes cleaning difficult.

Figure 21:
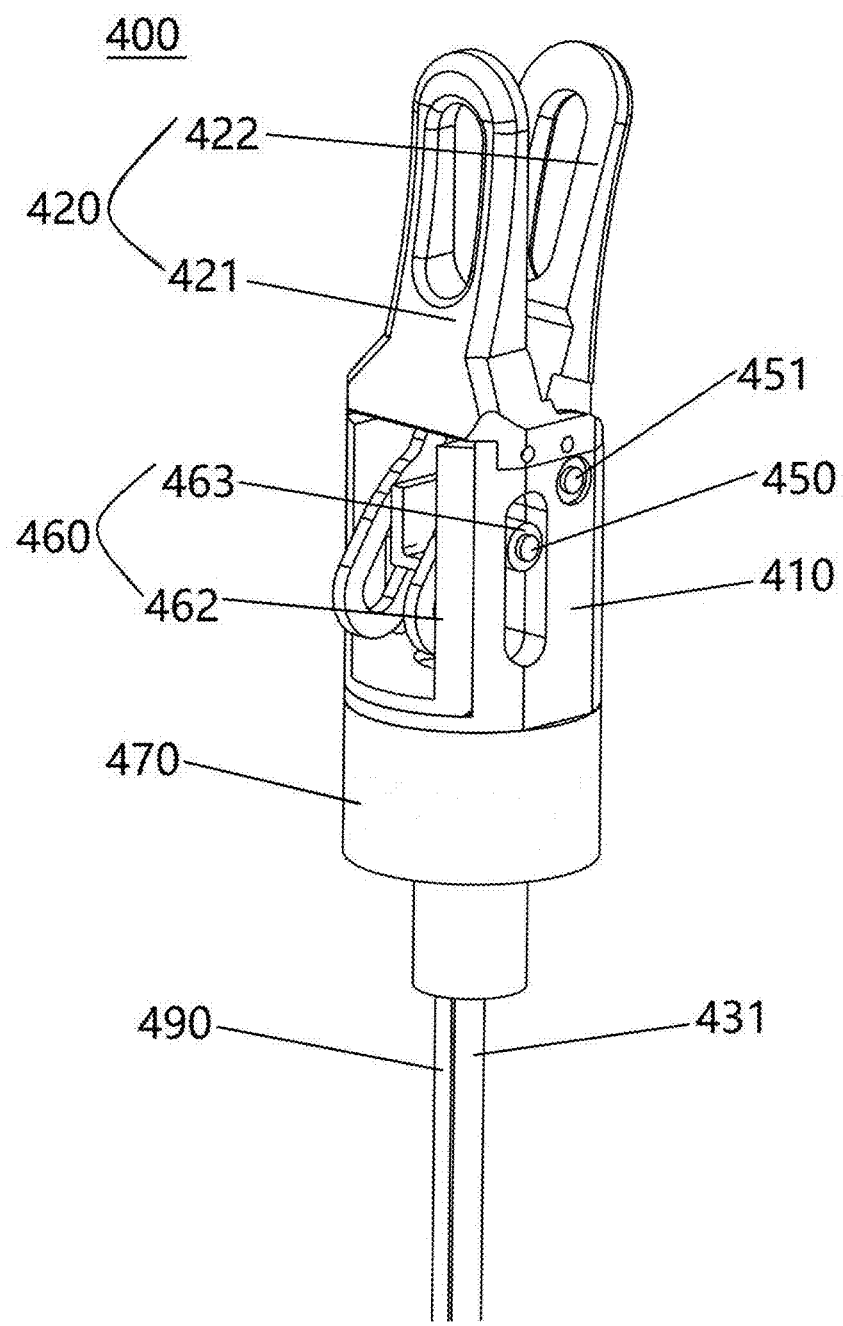
FIG. 21 shows a perspective view of a surgical effector according to some embodiments of the present disclosure.
Figure 22:
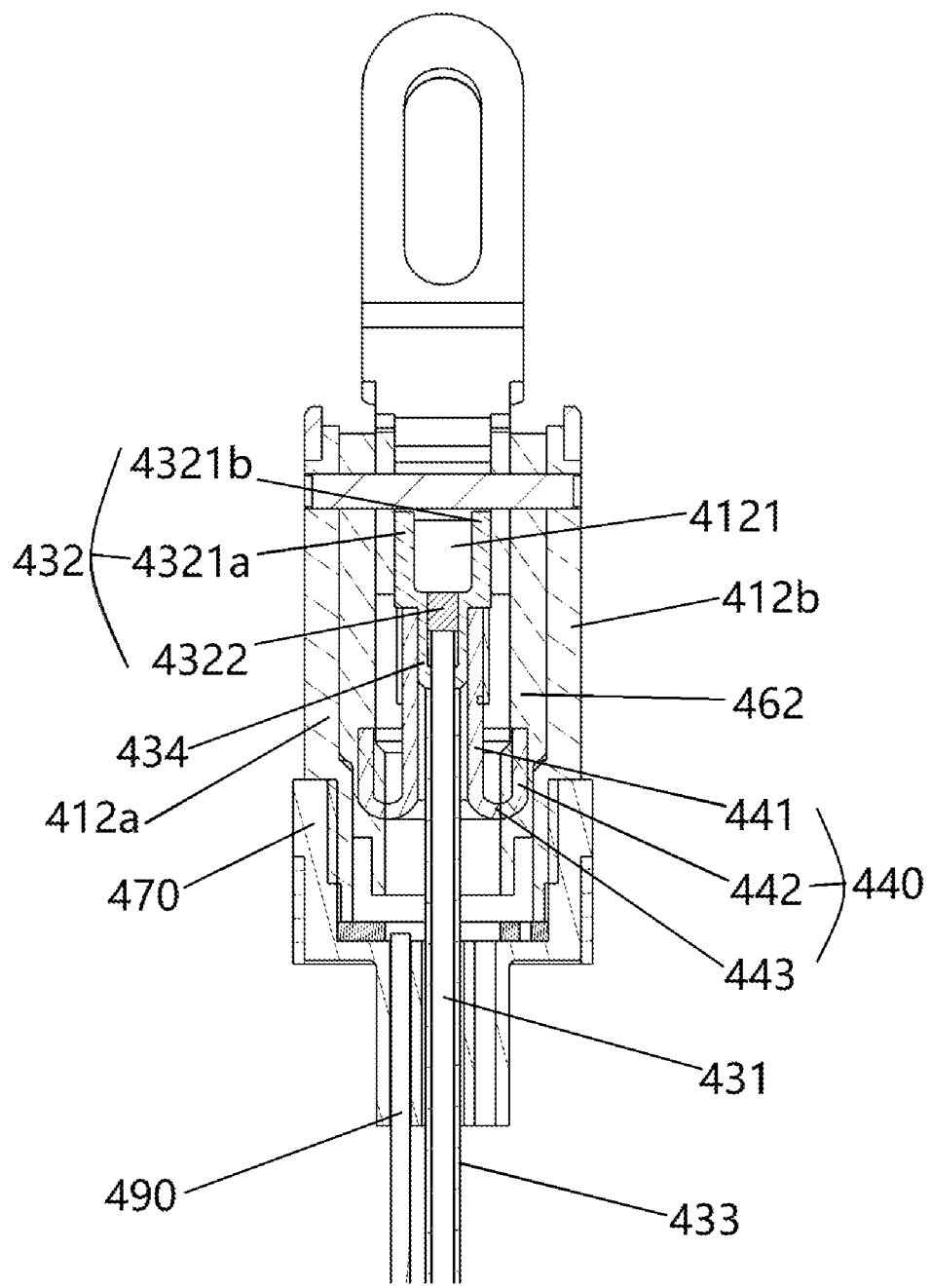
FIG. 22 shows a sectional view of a surgical effector according to some embodiments of the present disclosure.

FIGS. 21 and 22 respectively show a perspective view and a sectional view of a surgical effector 400 according to some embodiments of the present disclosure.

In some embodiments, the surgical effector 400 may comprise a head part 420, a support part 410, a drive part 430 (referring to FIG. 25), and a sealing member 440.

As shown in FIGS. 21 and 22, the head part 420 is at least partially movably arranged at a distal end of the support part 410. The support part 410 may comprise an inner cavity 4121, the drive part 430 (referring to FIG. 25) may be slidably arranged in the inner cavity 4121 of the support part 410 and is connected to a proximal end of the head part 420, so that at least a part of the head part 420 is driven to move relative to the distal end of the support part 410 by the movement of the drive part inside the support part 410.

The sealing member 440 may have a first end (e.g., a proximal end, or a distal end shown in FIG. 22) connected to the drive part 430 in a sealed manner and a second end (e.g., a distal end, or a proximal end shown in FIG. 22) connected to the support part 410 in a sealed manner, and at least a part of the sealing member 440 is deformable. Therefore, when the drive part 430 is relatively moved in the support part 410, the sealing member 440 can be deformed adaptively. The sealing member 440 can form a sealed isolation between the drive part 430, the support part 410 and the head part 420, so as to prevent patient's body fluids, bacteria and viruses from entering the interior of the surgical effector 400 through pores during a surgical operation, thereby facilitating repeated cleaning and disinfection of the surgical effector 400.

Figure 24:
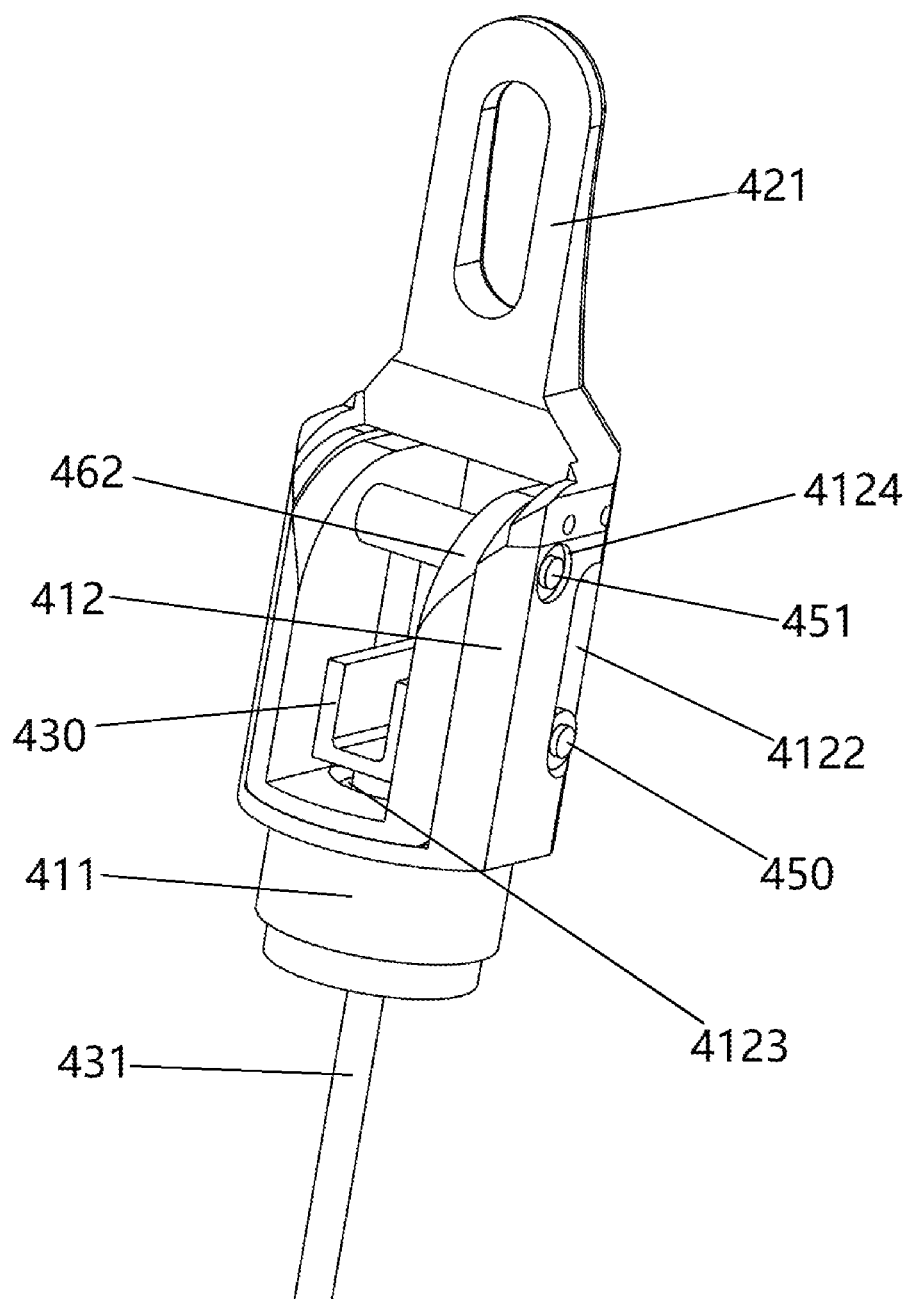
FIG. 24 shows a schematic structural view of a support part according to some embodiments of the present disclosure.

In some embodiments, the support part 410 may comprise at least one pair of support part slide slots. FIG. 24 shows a schematic structural view of a support part 410 according to some embodiments of the present disclosure. As shown in FIG. 24, the support part 410 may comprise a pair of support part slide slots 4122. The pair of support part slide slots 4122 may be a pair of axial slide slots radially opposed to each other and extending axially.

In some embodiments, as shown in FIGS. 22 and 24, the support part 410 may comprise a support connector 411 at the proximal end and a pair of support members 412a-b arranged circumferentially spaced apart from each other at the distal end of the support connector 411. The support connector 411 may be tubular, and its cross section may be circular, oval, rectangular, polygonal, etc. An axially-arranged hollow slideway 4123 (referring to FIG. 24) is formed in the support connector. The pair of support part slide slots 4122 may be oppositely and symmetrically formed in the support members 412a-b, respectively. The support members 412a-b may be fixedly connected to or integrally molded with the support connector 411. In some embodiments, the support members 412 of the support part 410 may be tubular or partially tubular, and their cross sections may be circular, oval, rectangular, polygonal, etc.

As shown in FIG. 21, the head part 420 may comprise a first head member 421 and a second head member 422 capable of mating with the first head member 421. In some embodiments, the first head member 421 may be fixedly arranged at the distal end of the support part 410, for example, by means of welding, bonding, integral molding, etc. The second head member 422 may be rotatably connected to the first head member 421 or the support part 410, for example, by means of hinging. As shown in FIG. 21, the first head member 421 may be integrally molded with or fixedly connected to a pair of support members 412. It should be understood that the first head member 421 may alternatively be integrally molded with or fixedly connected to one of the pair of support members 412 of the support part 410.

Figure 23:
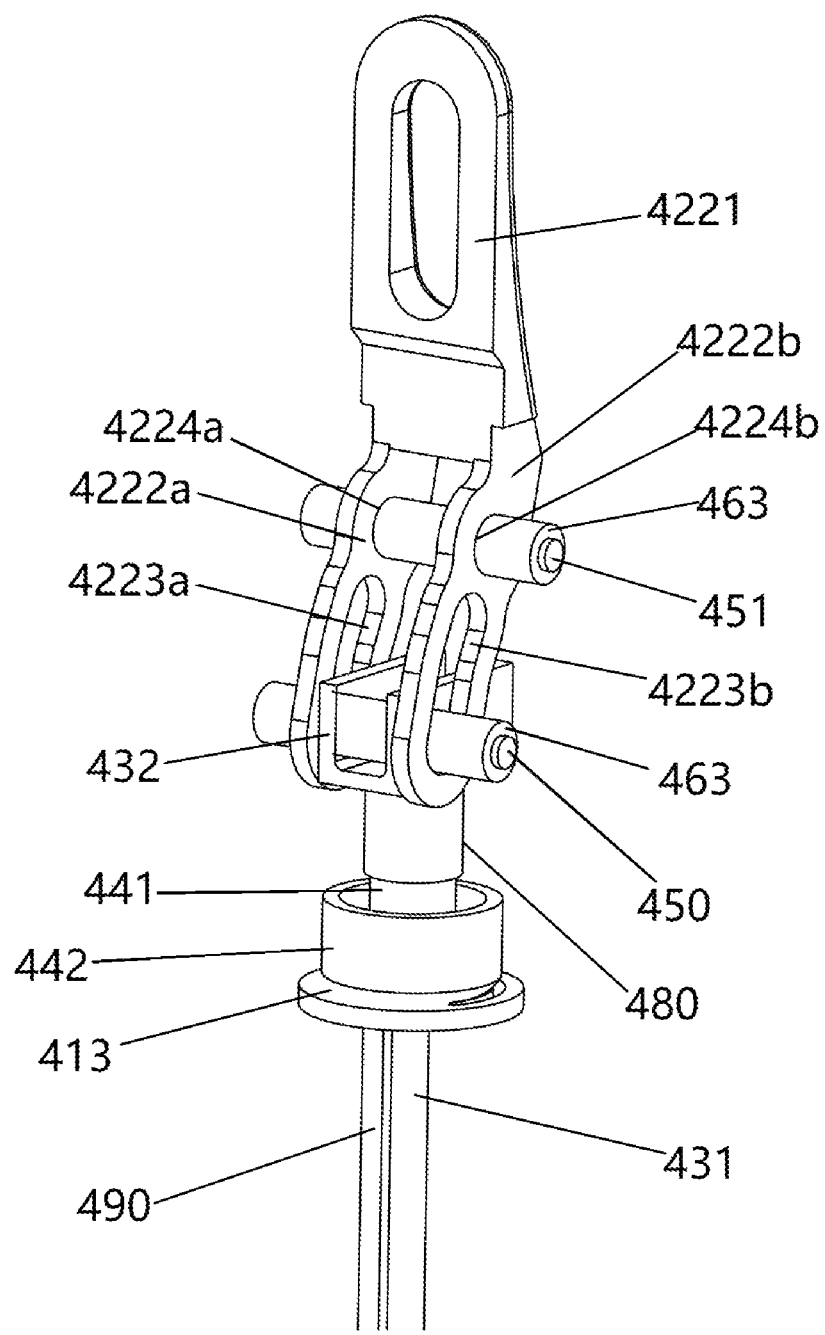
FIG. 23 shows a perspective view of a head part and a drive part cooperating with each other according to some embodiments of the present disclosure.

FIG. 23 shows a perspective view of a head part 420 and a drive part 430 cooperating with each other according to some embodiments of the present disclosure. As shown in FIG. 23, the second head member 422 may comprise a jaw 4221 and a pair of jaw support members 4222a and 4222b which are connected to and support the jaw 4221. The pair of jaw support members 4222a-b may be symmetrically arranged on two sides of a proximal end of the jaw 4221. Distal ends of the jaw support members 4222a-b are respectively provided with connecting holes 4224a-b opposed to each other. As shown in FIG. 23, the jaw support members 4222a-b may comprise jaw slide slots 4223a-b, respectively. In some embodiments, the jaw slide slots 4223a-b may be arc-shaped slide slots, and the jaw slide slots 4223a-b are arranged opposite each other on the jaw support members 4222a-b.

In some embodiments, the drive part 430 comprises a drive wire 431, as shown in FIGS. 21 to 25.

In some embodiments, the jaw support members 4222a-b may be arranged inside the support part 410. As shown in FIG. 21, a drive part connecting pin 450 may be slidably arranged in a pair of support part slide slots 4122 (as shown in FIG. 24) and a pair of jaw slide slots 4223a-b (as shown in FIG. 23). A pivotal connecting pin 451 passes through a pair of connecting holes 4224a-b (as shown in FIG. 23), and two ends of the pivotal connecting pin are respectively pivotally connected to the pair of support part connecting holes 4124 (referring to FIG. 24) of the support part 410, so that the second head member 422 is hinged to the support part 410. The drive part connecting pin 450 is connected to a distal end of the drive wire 431. When the drive wire 431 is pushed and/or pulled to relatively move in the hollow slideway 4123 of the support part 410, the drive part connecting pin 450 is driven to slide back and forth along the jaw slide slots 4223a-b and the pair of support part slide slots 4122, thereby driving the second head member 422 to be opened and closed relative to the first head member 421.

Figure 25:
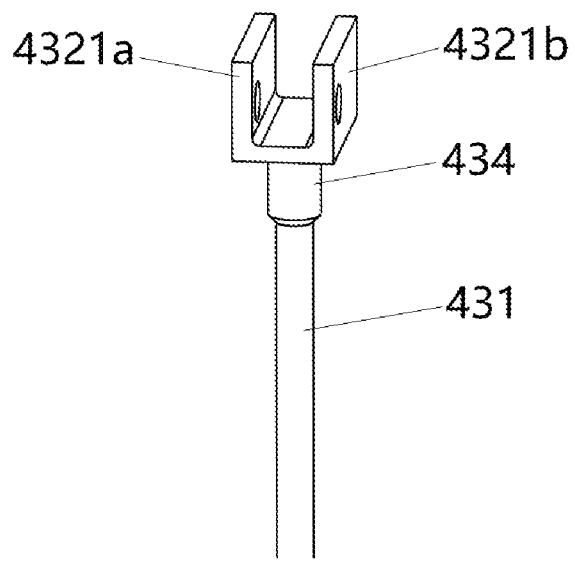
FIG. 25 shows a perspective view of a drive part according to some embodiments of the present disclosure.

FIG. 25 shows a schematic structural view of a drive part 430 according to some embodiments of the present disclosure. In some embodiments, as shown in FIGS. 22 and 25, the drive part 430 further comprises a slider 432. The drive part connecting pin 450 may be fixedly arranged at a distal end of the slider 432. The distal end of the drive wire 431 is connected to a proximal end of the slider 432. The slider 432 is slidably arranged in the inner cavity 4121 of the support part 410, and the drive wire 431 is configured to drive the slider 432 to reciprocate in the support part 410. As shown in FIG. 22, the sealing member 440 may be sleeved over an outer peripheral surface of the slider 432 or an outer peripheral surface of the proximal end part of the slider 432 in a sealed manner at the first end, and the sealing member 440 may also be configured to be attached to an inner wall of the proximal end of the support part 410 in a sealed manner at the second end. In some embodiments, the sealing member 440 may enclose an end portion of the proximal end of the support part 410, for example, an outer peripheral surface of the support connector 411, in a sealed manner at the second end. With the sealing member 440, the distal end part of the drive part 430 may be sealed relative to the hollow slideway 4123 of the support part 410. In some embodiments, the slider 432 may be of a structure in a cylindrical shape, a cube shape, a polyhedral shape or a special shape, and the drive part connecting pin 450 may be fixedly arranged at the distal end of the slider 432 in a radial direction of the slider 432.

As shown in FIGS. 22 and 25, the slider 432 may comprise a slide bar 4322 and a pair of slider connecting parts 4321a-b symmetrically arranged at a distal end of the slide bar 4322 and extending axially. The slide bar 4322 and the pair of slider connecting parts 4321a-b may be integrally formed, or may be separate from and fixedly connected to each other, for example, by means of welding or bonding. The drive part connecting pin 450 is fixedly arranged on the pair of slider connecting part 4321a-b. In some embodiments, as shown in FIGS. 22 and 25, a sliding sleeve 434 is sleeved over outer peripheries of the slide bar 4322 and the drive wire 431, and the sliding sleeve 434 and the pair of slider connecting parts 4321a-b may be integrally molded. It should be understood that the sliding sleeve 434 and the pair of slider connecting part 4321a-b may be separate from and fixedly connected to each other, for example, by means of welding or bonding. The sealing member 440 may be sleeved over an outer peripheral surface of the sliding sleeve 434 in a sealed manner at the first end, and the sealing member 440 may be attached to an inner peripheral surface of the proximal end of the support part 410, for example, an inner wall of the support connector 411, in a sealed manner at the second end, so that the distal end of the drive part 430 and the head part 420 are sealed relative to the hollow slideway 4123 of the support part 410. Although in the above embodiments, the drive part 430 may comprise the slider 432, the drive wire 431, and the sliding sleeve 434, it should be understood that the drive part 430 may be wholly or at least partially integrally molded.

In some embodiments, as shown in FIG. 22, the outer periphery of a part of the drive wire 431 located outside the sliding sleeve 434 is enclosed by an insulating protective sleeve 433, and the distal end of the drive wire 431 may pass through the insulating protective sleeve 433 and is connected to the end portion of the proximal end of the slider 432 in a secured manner, for example, by means of welding, bonding, integral molding, or secured snap-fit connection.

In some embodiments, the first head member 421 may be connected to a first power supply apparatus (not shown in the figure) so that a first conductive pathway is formed between the first head member 421 and the first power supply apparatus. A proximal end of the drive wire 431 may be connected to a second power supply apparatus (not shown in the figure) so that a second conductive pathway is formed between the second head member 422 and the drive wire 431. The first conductive pathway and the second conductive pathway are insulated from each other when the first head member 421 and the second head member 422 are not in contact with each other. The first conductive pathway and the second conductive pathway respectively supply power to the first head member 421 and the second head member 422 to form a "bipolar" structure, so as to carry out operations such as clamping and electrocoagulation.

In some embodiments, the slider 432 may be made of a conductive material, for example, metal. Those skilled in the art should understand that the slider 432 may alternatively be plated with a conductive layer on its surface to achieve a function of electric conduction. The proximal end of the drive wire 431 may be connected to the second power supply apparatus so that a second conductive pathway may be formed between the second head member 422 and the drive wire 431 by means of the slider 432. The first power supply apparatus may directly form a first conductive pathway with the first head member 421 by means of a conductive wire 490 (referring to FIGS. 22 and 23), or the first power supply apparatus may be electrically connected to the support part 410 by means of a conductive wire 490, and the support part 410 is electrically connected to the first head member 421 to form a first conductive pathway. An insulation part 460 (referring to FIG. 21) is arranged between at least one of the first head member 421 and the second head member 422, and the support part 410, so that the first head member 421 and the second head member 422 are insulated from each other when they are separated. The first head member 421 and the second head member 422 can form a conductive pathway by means of a tissue when clamping the tissue, so as to carry out operations such as tissue clamping and electrocoagulation.

In some embodiments, an insulation part 460 may be arranged between the first head member 421 and the support part 410. Those skilled in the art should understand that the support part 410 may be directly made of an insulating material, the insulation part 460 may be directly a part of the support part 410, or the insulation part 460 may comprise a first insulating member (not shown in the figure) that is fixedly arranged on the support part 410. The first insulating member may comprise an insulating layer or an insulating fixing member arranged at a joint between the first head member 421 and the support part 410, so as to realize insulation between the first head member 421 and the support part 410, thereby realizing insulation between the first head member and the second head member 422. The first head member 421 is fixedly arranged or integrally molded on the support part 410, or is fixedly arranged on the first insulating member, and the first power supply apparatus may be directly electrically connected to the first head member 421 via the conductive wire 490 to form the first conductive pathway. As shown in FIG. 24, the first head member 421 may be fixedly arranged on a pair of support members 412 of the support part 410.

In some embodiments, the support part 410 may be made of a conductive material, the first power supply apparatus and the support part 410 form a conductive pathway by means of the conductive wire 490, and the first head member 421 and the first power supply apparatus form a first conductive pathway by means of the support part 410. An insulation part 460 may be arranged between the second head member 422 and the support part 410. As shown in FIGS. 22 and 24, the insulation part 460 may comprise a support frame insulating lining 462 closely attached to an inner wall of the support part 410, and a second insulating member 463 arranged at a contact position between the second head member 422 and the support part 410. The first head member 421 is fixedly arranged at the distal ends of the support members 412a-b, or is integrally molded with the support members 412a-b. The support frame insulating lining 462 may be made of an insulating material such as rubber, plastic, or ceramic. The support frame insulating lining 462 can prevent the second head member 422 from coming into contact with an inner peripheral surface of the support part 410 to form a conductive pathway during moving. In some embodiments, as shown in FIG. 24, the support frame insulating lining 462 may match the support part 410 in shape. The support frame insulating lining 462 has an inner cavity. The jaw support members 4222a-b of the second head member 422, the slider 432, and the sealing member 440 are all located in the inner cavity of the support frame insulating lining 462. An outer wall of the support frame insulating lining 462 is closely attached to an inner wall of the support part 410. The support frame insulating lining 462 is provided with a pair of slide slots corresponding to the support part slide slots 4122, and a pair of connecting holes corresponding to the connecting holes 4224a-b and the pair of support part connecting holes 4124. As shown in FIG. 23, the jaw support members 4222a-b may be respectively located on two sides of the slider connecting parts 4321a-b, the drive part connecting pin 450 is fixedly arranged in the slider connecting parts 4321a-b, and two ends of the drive part connecting pin 450 may be respectively slidably arranged in the jaw slide slots 4223a-b, the pair of slide slots of the support frame insulating lining 462, and the pair of support part slide slots 4122. Two ends of the pivotal connecting pin 451 may be arranged in the pair of connecting holes 4224a-b of the support part 410 after respectively passing through the jaw support members 4222a-b, and the pair of connecting holes in the support frame insulating lining 462. It should be understood that the support frame insulating lining 462 may alternatively be any other structure capable of preventing the second head member 422 from coming into contact with the inner peripheral surface of the support part 410 to form a conductive pathway, without departing from the scope of disclosure.

Contact positions between the jaw support members 4222a-b of the second head member 422 and the support part 410 may comprise the inner peripheral surface of the support part 410, or the drive part connecting pin 450 and the pivotal connecting pin 451, or surfaces of the support part slide slots 4122a-b of the support part 410, or the jaw slide slots 4223a-b of the jaw support members 4222a-b. As shown in FIG. 23, the second insulating member 463 may be a connecting pin insulating sleeve or an insulating layer enclosing the outer periphery of each of the drive part connecting pin 450 and the pivotal connecting pin 451 or the out peripheries of two end portions of the drive part connecting pin and the pivotal connecting pin. It should be understood that, in some embodiments, the second insulating member 463 may alternatively be an insulating layer arranged on the surfaces of the support part slide slots 4122a-b. Therefore, insulation between the second head member 422 and the support part 410 can be ensured when they are connected via the drive part connecting pin 450 and the pivotal connecting pin 451 at the contact position. A second conductive pathway may be formed between the second head member 422 and the second power supply apparatus by means of the drive part connecting pin 450, the slider 432, and the drive wire 431, or a second conductive pathway may be formed between the second head member 422 and the second power supply apparatus by means of the slider 432 and the drive wire 431. The second conductive pathway can be insulated from the first conductive pathway through the matching between the support frame insulating lining 462 and the second insulating member 463, so that the structure of the insulation part can be simplified. The first head member 421 and the second head member 422 respectively form a conductive pathway, and the two conductive pathways are insulated from each other. The first head member 421, the second head member 422, the drive wire 431, the slider 432, the drive part connecting pin 450, and the pivotal connecting pin 451 may all be made of a conductive material, such as metal and a stainless steel material, or may be plated with a conductive layer on their surfaces to achieve a function of electric conduction. In some embodiments, the drive part connecting pin 450 and the pivotal connecting pin 451 may also be made of an insulating material. Since insulation of monopolar or bipolar tools of small-sized surgical effectors is realized, insulation between the surgical effectors, and between a surgical effector and a surgical tool arm or a robot arm of a surgical robot is formed, thereby ensuring that the parts other than the surgical effector will not burn the patient and the user, avoiding damage to devices, etc.

In some embodiments, an annular conductive plate 413 is arranged on an end portion of the support part 410 away from the first head member 421, the conductive wire 490 is connected to the annular conductive plate 413, and a conductor in the conductive wire 490 is in contact with the annular conductive plate 413 to form an electrical connection, as shown in FIG. 23. With the arrangement of the annular conductive plate 413, the contact area with the support part 410 can be increased, which is easier for the conductive wire 490 to form a conductive pathway with the support part 410.

Figure 26:
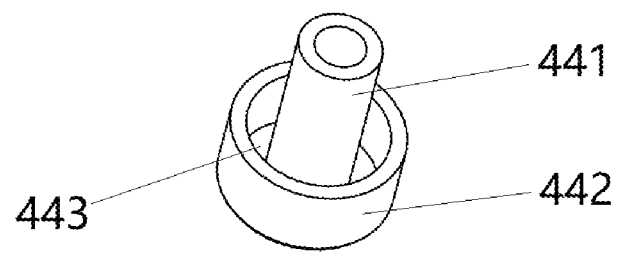
FIG. 26 shows a perspective view of a sealing member according to some embodiments of the present disclosure.

FIG. 26 shows a perspective view of a sealing member 440 according to some embodiments of the present disclosure. As shown in FIGS. 22 and 26, the sealing member 440 may comprise an inner tubular portion 441, an outer tubular portion 442, and a curved transition portion 443. The inner tubular portion 441 may be sleeved over an outer peripheral surface of the proximal end of the slider 432 (e.g., of the sliding sleeve 434, or the slide bar 4322) and located in the inner cavity 4121 of the support part 410, and the inner tubular portion 441 can be driven by the slider 432 to axially move along the inner cavity 4121. An outer wall of the outer tubular portion 442 may be attached to an inner peripheral surface of the proximal end of the support part 410 in a sealed manner, or enclose the outer peripheral surface of the proximal end of the support part 410 in a sealed manner. In some embodiments, as shown in FIG. 22, the outer wall of the outer tubular portion 442 may be attached to an inner peripheral surface of a proximal end of the support frame insulating lining 462 in a sealed manner. However, it should be understood that an inner wall of the outer tubular portion 442 may enclose an outer peripheral surface of the proximal end of the support frame insulating lining 462 in a sealed manner. The outer tubular portion 442 is integrally connected to the inner tubular portion 441 via the curved transition portion 443. Thus, with the sealing member 440, it is possible to seal the distal end of slider 432, the head part 420 and the drive wire 431 relative to the distal side of the sealing member 440, so that the drive wire 431 is isolated from a surgical interface.

In some embodiments, as shown in FIG. 23, a ferrule 480 may be sleeved outside the inner tubular portion 441 of the sealing member 440 so that the sealing member 440 is connected to the slider 432 in a sealed and secured manner. In some embodiments, a ferrule (not shown in the figure) may also be sleeved outside the outer tubular portion 442 of the sealing member 440, and the ferrule may be connected to the proximal end of the support part 410 in a secured manner, so that the outer tubular portion 442 is connected to the proximal end of the support part 410 in a sealed and secured manner. With the arrangement of the ferrules, the sealing performance between the sealing member 440 and the drive wire 431 as well as between the sealing member 440 and the support part 410 can be further ensured respectively, and the risk of the sealing member 440 slipping off during expanding and retracting movements can be reduced.

Figure 27:
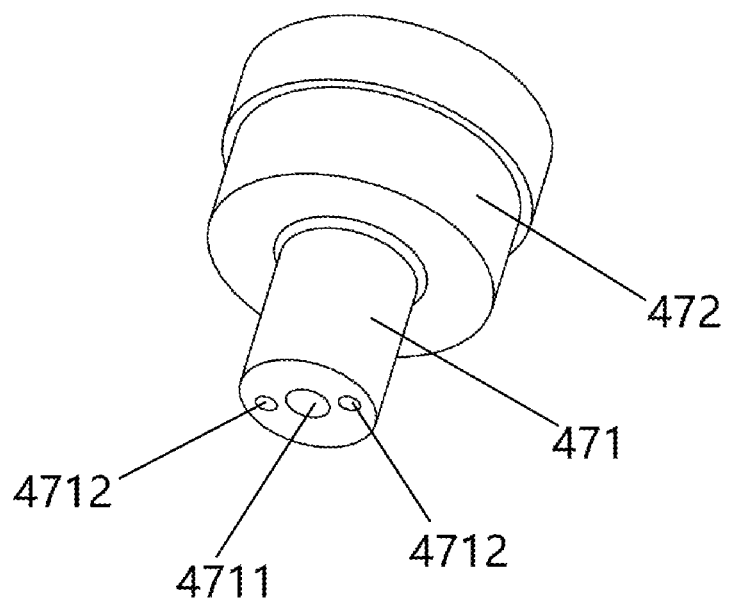
FIG. 27 shows a perspective view of a protective sleeve according to some embodiments of the present disclosure.

FIG. 27 shows a perspective view of a protective sleeve 470 according to some embodiments of the present disclosure. In some embodiments, a protective sleeve 470 may also be arranged on the outer periphery of the proximal end of the support part 410. As shown in FIG. 27, the protective sleeve 470 may comprise a proximal segment 471 and a distal segment 472. The distal segment 472 has a radial dimension greater than that of the proximal segment 471. The distal segment 472 of the protective sleeve 470 may comprise a receiving groove at the distal end (not shown in the figure). The receiving groove of the protective sleeve 470 receives the proximal end of the support part 410 and forms a sealing with an end portion of the support part 410. Those skilled in the art should understand that the distal segment 472 and the proximal end of the support part 410 may be in threaded connection, in interference-fit connection, welded, bonded, integral molded, etc. The proximal segment 471 of the protective sleeve 470 receives the drive wire 431. As shown in FIG. 27, a drive wire through hole 4711 and at least one conductive wire through hole 4712 respectively for the drive wire 431 and the conductive wire 490 to pass through may be formed in an end portion of the proximal segment 471 of the protective sleeve 470. In some embodiments, the protective sleeve 470 may be an insulator of rubber, plastic, ceramic, etc. The protective sleeve 470 can insulate the surgical effector from an arm of a surgical tool, and can prevent contaminants from entering the interior of the surgical tool, which makes cleaning difficult.

Figure 28:
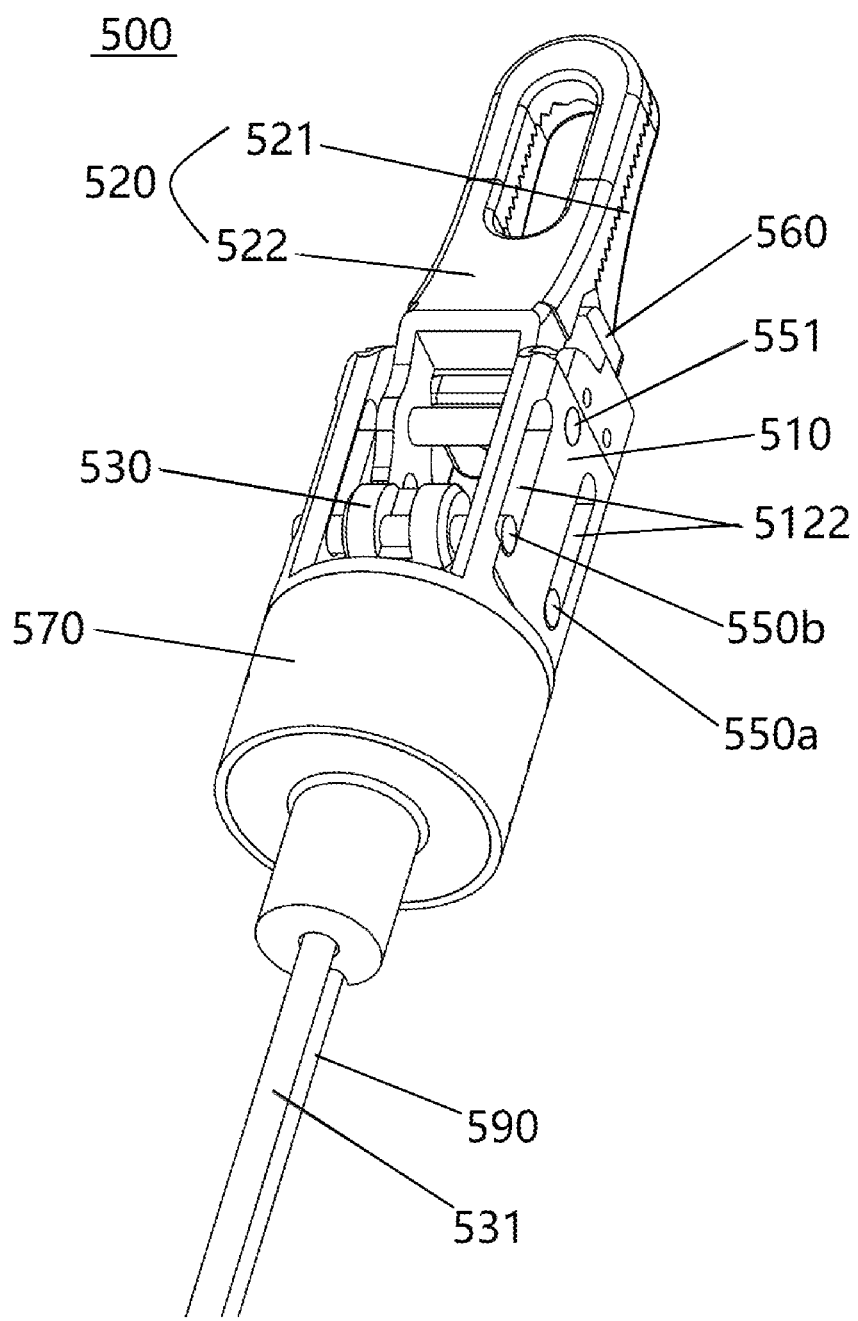
FIG. 28 shows a perspective view of a surgical effector according to some embodiments of the present disclosure.
Figure 29:
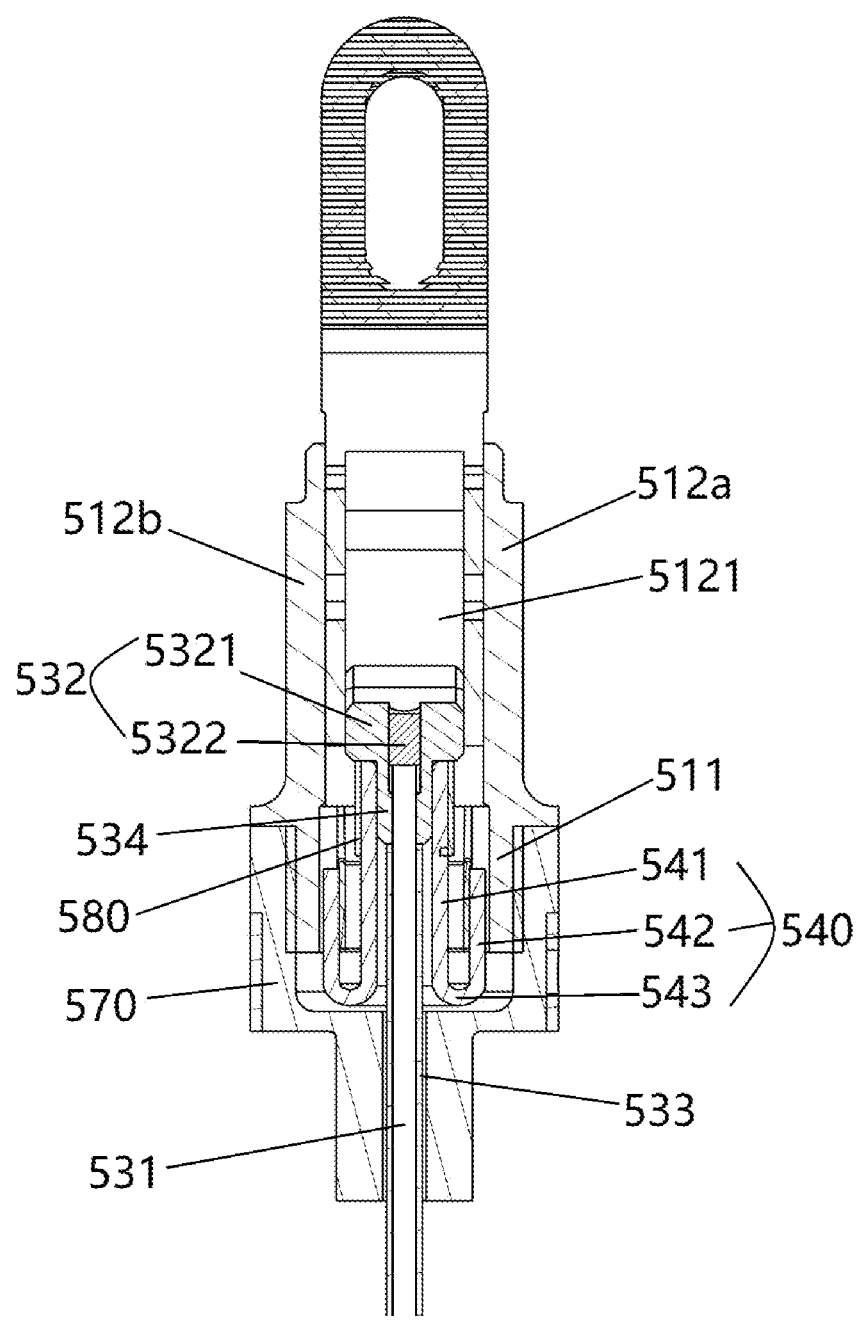
FIG. 29 shows a sectional view of a surgical effector according to some embodiments of the present disclosure.

FIGS. 28 and 29 respectively show a perspective view and a sectional view of a surgical effector 500 according to some embodiments of the present disclosure.

In some embodiments, the surgical effector 500 may comprise a head part 520, a support part 510, a drive part 530, and a sealing member 540.

As shown in FIGS. 28 and 29, the head part 520 is at least partially movably arranged at a distal end of the support part 510. The support part 510 may comprise an inner cavity 5121, the drive part 530 (referring to FIG. 33) may be slidably arranged in the inner cavity 5121 of the support part 510 and is connected to a proximal end of the head part 520, so that at least a part of the head part 520 is driven to move relative to the distal end of the support part 510 by the movement of the drive part inside the support part 510.

The sealing member 540 may be connected to the drive part 530 in a sealed manner at a first end (e.g., a proximal end, or a distal end shown in FIG. 29) thereof and connected to the support part 510 in a sealed manner at a second end (e.g., a distal end, or a proximal end shown in FIG. 29) thereof, and at least a part of the sealing member 540 is deformable. Therefore, when the drive part 530 is relatively moved in the support part 510, the sealing member 540 can be deformed adaptively. The sealing member 540 can form a sealed isolation between the drive part 530, the support part 510 and the head part 520, so as to prevent patient's body fluids, bacteria and viruses from entering the interior of the surgical effector 500 through pores during a surgical operation, thereby facilitating repeated cleaning and disinfection of the surgical effector 500.

Figure 30:
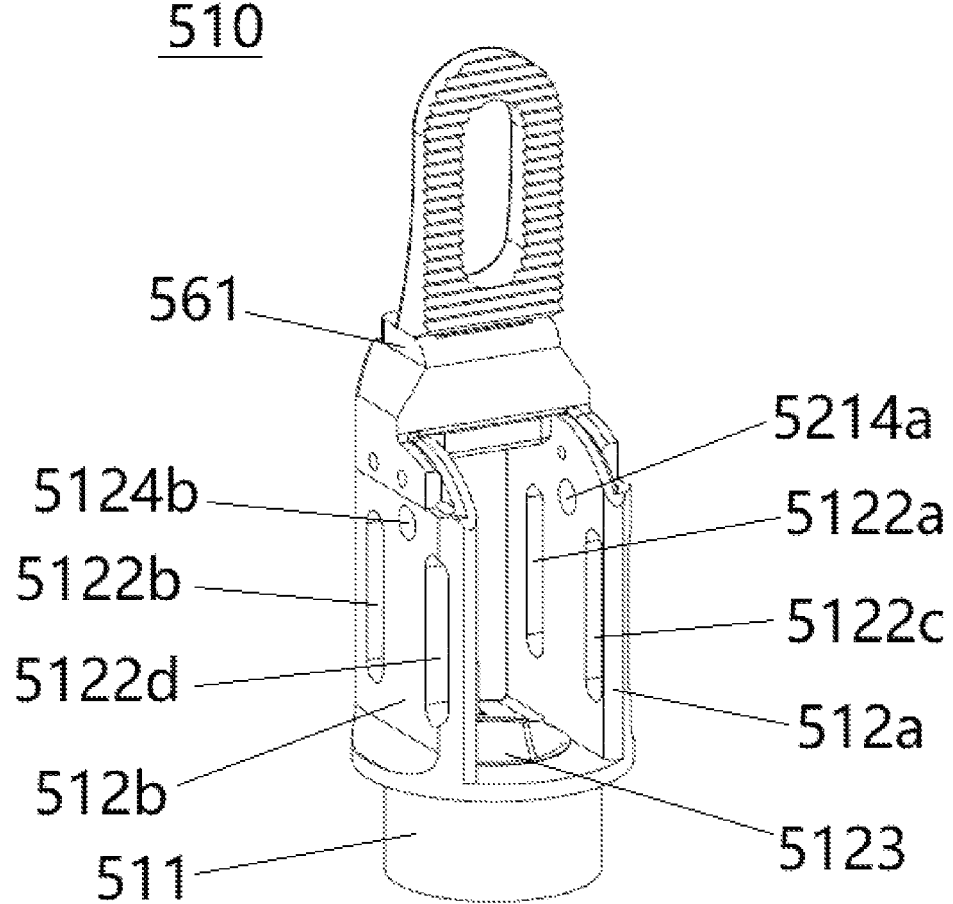
FIG. 30 shows a schematic structural view of a support part according to some embodiments of the present disclosure.

In some embodiments, the support part 510 may comprise at least one pair of support part slide slots 5122. FIG. 30 shows a schematic structural view of a support part 510 according to some embodiments of the present disclosure. As shown in FIG. 30, the support part 510 may comprise support part slide slots 5122a-d, and the support part slide slots 5122a-b and 5122c-d may be two pairs of axial slide slots radially opposed to each other and extending axially.

In some embodiments, as shown in FIGS. 29 and 30, the support part 510 may comprise a support connector 511 at the proximal end and a pair of support members 512a-b arranged circumferentially spaced apart from each other at the distal end of the support connector 511. The support connector 511 may be tubular, and its cross section may be circular, oval, rectangular, polygonal, etc. An axially-arranged hollow slideway 5123 is formed in the support connector. The two pairs of support part slide slots 5122a-b and 5122c-d may be oppositely and symmetrically formed in the support members 512a-b, respectively. The support members 512a-b may be fixedly connected to or integrally molded with the support connector 511. In some embodiments, the support members 512 of the support part 510 may be tubular or partially tubular, and their cross sections may be circular, oval, rectangular, polygonal, etc.

As shown in FIG. 28, the head part 520 may comprise a first head member 521 and a second head member 522 capable of mating with the first head member 521. In some embodiments, the first head member 521 may be fixedly arranged at the distal end of the support part 510, for example, by means of welding, bonding, integral molding, etc. The second head member 522 may be rotatably connected to the first head member 521 or the support part 510, for example, by means of hinging. As shown in FIGS. 28 and 30, the first head member 521 may be integrally molded with or fixedly connected to a pair of support members 512a-b. It should be understood that the first head member 521 may alternatively be integrally molded with or fixedly connected to one of the support members 512a-b of the support part 510.

Figure 31:
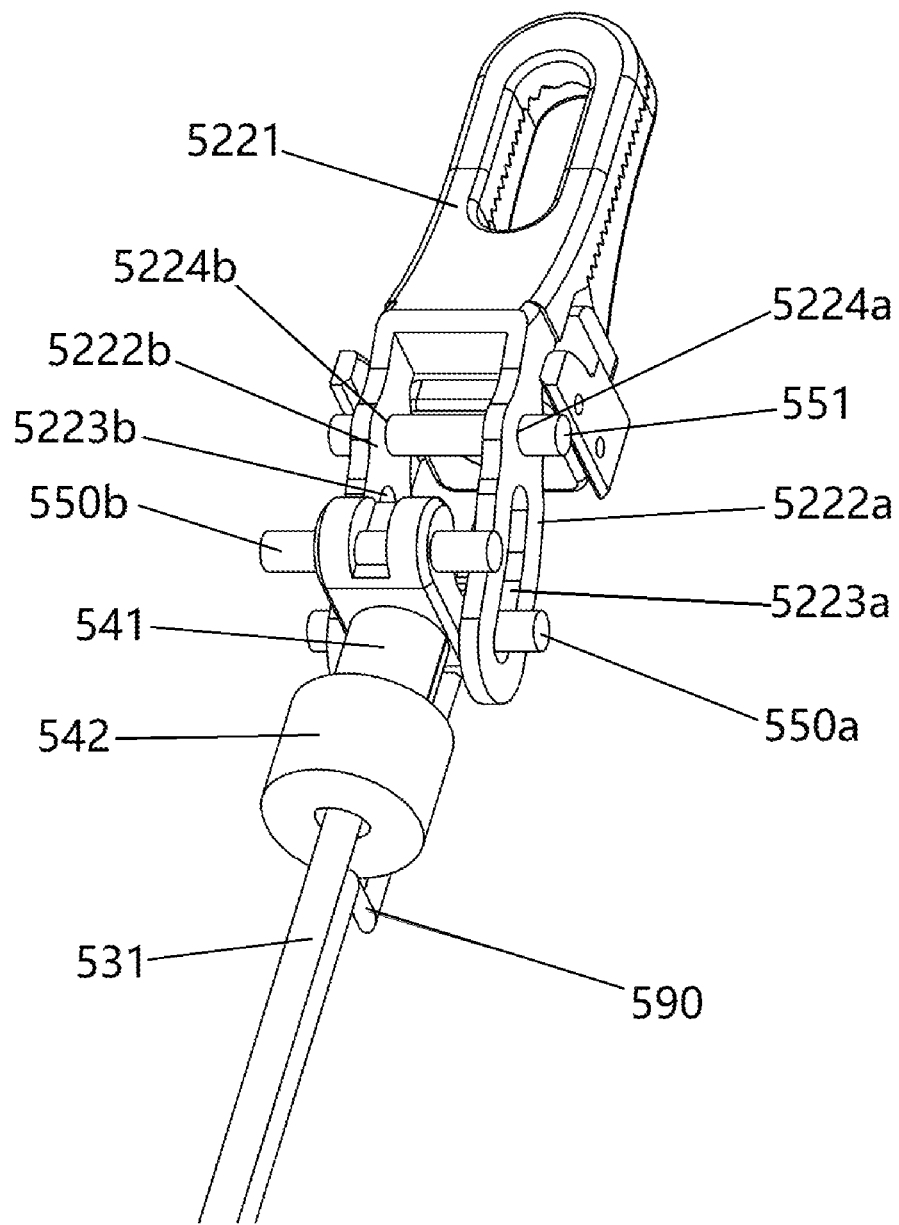
FIG. 31 shows a perspective view of a head part and a drive part cooperating with each other according to some embodiments of the present disclosure.
Figure 32:
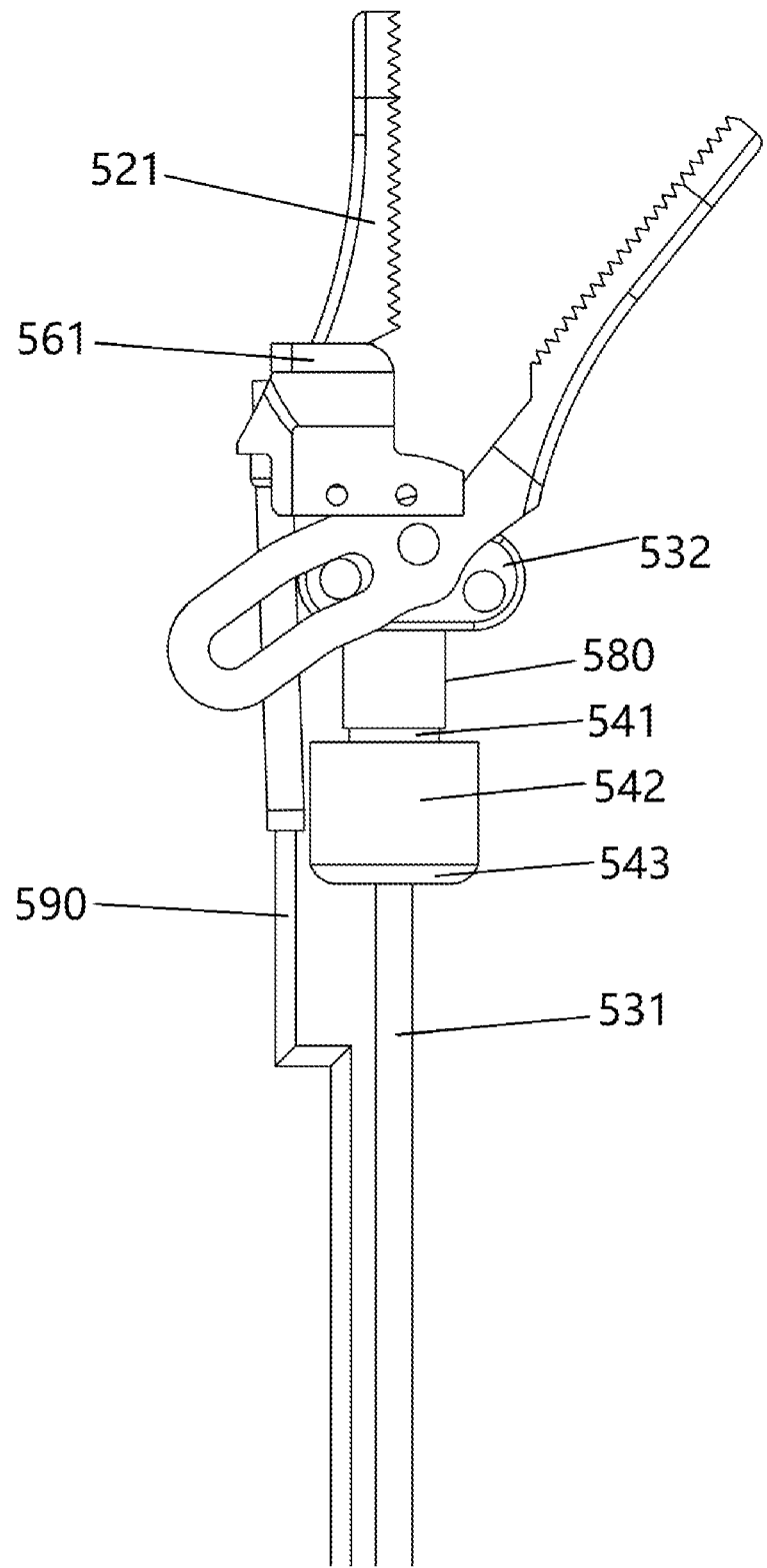
FIG. 32 shows a side view of a head part and a drive part cooperating with each other according to some embodiments of the present disclosure.

FIGS. 31 and 32 respectively show a perspective view and a side view of a head part 520 and a drive part 530 cooperating with each other according to some embodiments of the present disclosure. As shown in FIG. 31, the second head member 522 may comprise a jaw 5221 and a pair of jaw support members 5222a and 5222b which are connected to and support the jaw 5221. The pair of jaw support members 5222a-b may be symmetrically arranged on two sides of a proximal end of the jaw 5221. Distal ends of the jaw support members 5222a-b are respectively provided with connecting holes 5224a-b opposed to each other. As shown in FIG. 31, the jaw support members 5222a-b may comprise jaw slide slots 5223a-b, respectively. In some embodiments, the jaw slide slots 5223a-b may be arc-shaped slide slots, and the jaw slide slots 5223a-b are arranged opposite each other on the jaw support members 5222a-b.

Figure 33:
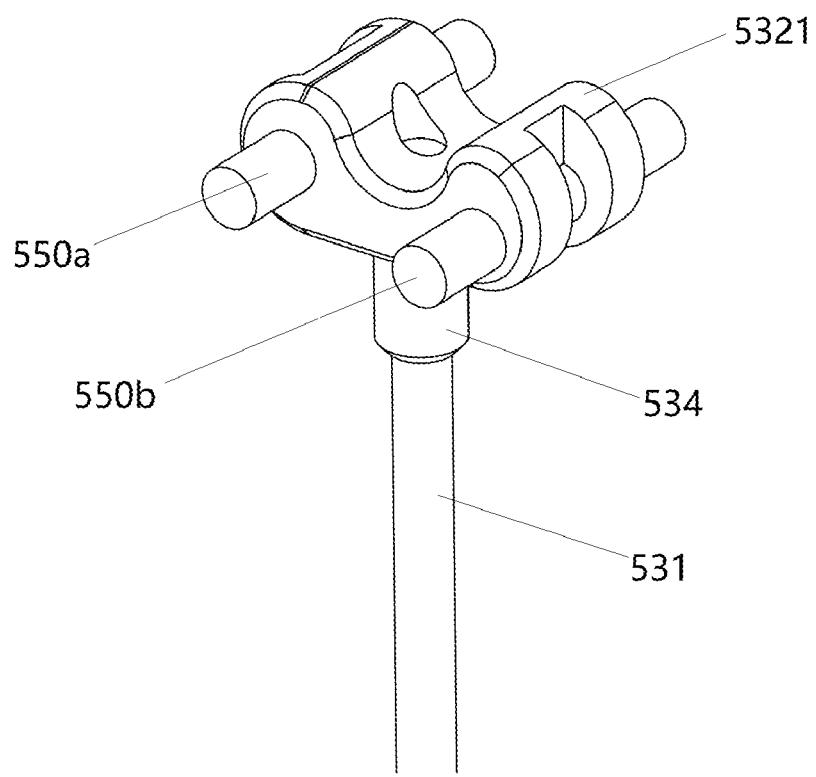
FIG. 33 shows a perspective view of a drive part according to some embodiments of the present disclosure.

FIG. 33 shows a perspective view of a drive part according to some embodiments of the present disclosure. As shown in FIG. 33, in some embodiments, the drive part 530 comprises a drive wire 531.

In some embodiments, the jaw support members 5222a-b may be arranged inside the support part 510. As shown in FIG. 31, a pair of drive part connecting pins 550a-b may be respectively slidably arranged in two pairs of support part slide slots 5122a-b and 5122c-d (as shown in FIG. 30), and the drive part connecting pin 550a may also be slidably arranged in the jaw slide slots 5223a-b. A pivotal connecting pin 551 passes through a pair of connecting holes 5224a-b, and two ends of the pivotal connecting pin are respectively pivotally connected to the pair of support part connecting holes 5124a-b (referring to FIG. 30) of the support part 510, so that the second head member 522 is hinged to the support part 510. The pair of drive part connecting pins 550a-b are connected to a distal end of the drive wire 531. When the drive wire 531 is pushed and/or pulled to relatively move in the hollow slideway 5123 of the support part 510, the drive part connecting pin 550a is driven to slide back and forth along the jaw slide slots 5223a-b and one pair of support part slide slots 5122a-b, and the drive part connecting pin 550b is driven to slide back and forth along the other pair of support part slide slots 5122c-d, thereby driving the second head member 522 to be opened and closed relative to the first head member 521.

In some embodiments, as shown in FIGS. 29 and 33, the drive part 530 may further comprise a slider 532. The drive part connecting pins 550a-b may be fixedly arranged at a distal end of the slider 532. The distal end of the drive wire 531 is connected to a proximal end of the slider 532. The slider 532 is slidably arranged in the inner cavity 5121 of the support part 510, and the drive wire 531 is configured to drive the slider 532 to reciprocate in the support part 510. As shown in FIGS. 29, 31 and 32, the sealing member 540 may be sleeved over an outer peripheral surface of the slider 532 or an outer peripheral surface of the proximal end part of the slider 532 in a sealed manner at the first end, and the sealing member 540 may also be configured to be attached to an inner wall of the proximal end of the support part 510 in a sealed manner at the second end. In some embodiments, the sealing member 540 may enclose an end portion of the proximal end of the support part 510 in a sealed manner at the second end. With the sealing member 540, the distal end part of the drive part 530 may be sealed relative to the hollow slideway 5123 of the support part 510. In some embodiments, the slider 532 may be of a structure in a cylindrical shape, a cube shape, a polyhedral shape or a special shape, and the drive part connecting pin 550a-b may be fixedly arranged at the distal end of the slider 532 and spaced apart from each other in a transverse direction of the slider 532.

As shown in FIGS. 29 and 33, the slider 532 may comprise a radially-extending pin connecting part 5321 and a slide bar 5322 extending axially from the pin connecting part 5321 to the proximal side. The slide bar 5322 and the pin connecting part 5321 may be integrally formed, or may be separate from and fixedly connected to each other, for example, by means of welding or bonding. The drive part connecting pins 550a-b are fixedly arranged on the pin connecting part 5321. In some embodiments, as shown in FIGS. 29 and 33, a sliding sleeve 534 is sleeved over outer peripheries of the slide bar 5322 and the drive wire 531, and the sliding sleeve 534 and the pair of slider connecting parts 5321a-b may be integrally molded. It should be understood that the sliding sleeve 534 and the pair of slider connecting part 5321a-b may be separate from and fixedly connected to each other, for example, by means of welding or bonding. The sealing member 540 may be sleeved over an outer peripheral surface of the sliding sleeve 534 in a sealed manner at the first end, and the sealing member 540 may be attached to an inner peripheral surface of the proximal end of the support part 510 in a sealed manner at the second end, so that the distal end of the drive part 530 and the head part 520 are sealed relative to the hollow slideway 5123 of the support part 510. Although in the above embodiments, the drive part 530 may comprise the slider 532, the drive wire 531, and the sliding sleeve 534, it should be understood that the drive part 530 may be wholly or at least partially integrally molded.

In some embodiments, as shown in FIG. 29, the outer periphery of each part of the drive wire 531 located outside the sliding sleeve 534 is enclosed by an insulating protective sleeve 533, and the distal end of the drive wire 531 may pass through the insulating protective sleeve 533 and is connected to the end portion of the proximal end of the slider 532 in a secured manner, for example, by means of welding, bonding, integral molding, or secured snap-fit connection.

In some embodiments, the first head member 521 may be connected to a first power supply apparatus (not shown in the figure) so that a first conductive pathway is formed between the first head member 521 and the first power supply apparatus. A proximal end of the drive wire 531 may be connected to a second power supply apparatus (not shown in the figure) so that a second conductive pathway is formed between the second head member 522 and the drive wire 531. The first conductive pathway and the second conductive pathway are insulated from each other when the first head member 521 and the second head member 522 are not in contact with each other. The first conductive pathway and the second conductive pathway respectively supply power to the first head member 521 and the second head member 522 to form a "bipolar" structure, so as to carry out operations such as clamping and electrocoagulation.

In some embodiments, the slider 532 may be made of a conductive material, for example, metal. Those skilled in the art should understand that the slider 532 may alternatively be plated with a conductive layer on its surface to achieve a function of electric conduction. The proximal end of the drive wire 531 may be connected to the second power supply apparatus so that a second conductive pathway may be formed between the second head member 522 and the drive wire 531 by means of the slider 532. The first power supply apparatus may directly form a first conductive pathway with the first head member 521 by means of a conductive wire 590 (referring to FIG. 32), or the first power supply apparatus may be electrically connected to the support part 510 by means of a conductive wire 590, and the support part 510 is electrically connected to the first head member 521 to form a first conductive pathway. An insulation part 560 (referring to FIG. 28) is arranged between at least one of the first head member 521 and the second head member 522, and the support part 510, so that the first head member 521 and the second head member 522 are insulated from each other when they are separated. The first head member 521 and the second head member 522 can form a conductive pathway by means of a tissue when clamping the tissue, so as to carry out operations such as tissue clamping and electrocoagulation.

As shown in FIG. 28, in some embodiments, an insulation part 560 may be arranged between the first head member 521 and the support part 510. Those skilled in the art should understand that the support part 510 may be directly made of an insulating material, the insulation part 560 may be directly a part of the support part 510, or the insulation part 560 may comprise a first insulating member 561 that is fixedly arranged on the support part 510, as shown in FIG. 31. As shown in FIGS. 30 and 32, the first insulating member 561 may comprise an insulating isolation layer or an insulating fixing member arranged at a joint between the first head member 521 and the support part 510, so as to realize insulation between the first head member 521 and the support part 510, thereby realizing insulation between the first head member and the second head member 522. As shown in FIG. 30, the first head member 521 is fixedly arranged or integrally molded on the support part 510, or is fixedly arranged on the first insulating member 561, and the first power supply apparatus may be directly electrically connected to the first head member 521 via the conductive wire 590 to form the first conductive pathway. As shown in FIG. 30, the first head member 521 may be fixedly arranged on a pair of support members 512a-b of the support part 510.

In some embodiments, the support part 510 may be made of a conductive material, the first power supply apparatus and the support part 510 form a conductive pathway by means of the conductive wire 590, and the first head member 521 and the first power supply apparatus form a first conductive pathway by means of the support part 510. An insulation part 560 may be arranged between the second head member 522 and the support part 510. The insulation part 560 may comprise a second insulating member (not shown in the figure) arranged at a contact position between the second head member 522 and the support part 510. It should be understood that the contact positions between the jaw support members 5222a-b of the second head member 522 and the support part 510 may comprise the drive part connecting pins 550a-b and two ends of the pivotal connecting pin 551 or surfaces of the support part slide slots 5122a-d of the support part 510. The second insulating member may comprise insulating members that are in contact with the second head member 522 and arranged on the support part slide slots 5122a-d, insulating layers arranged at the drive part connecting pins 550a-b and the two ends of the pivotal connecting pin 551, or an insulating layer or insulating member arranged at another contact position. Therefore, the second head member 522 can be insulated from the support part 510, so that insulation between the second conductive pathway and the first conductive pathway can be realized, and the structure of the insulation part may be simplified. The first head member 521 and the second head member 522 respectively form a conductive pathway, and the two conductive pathways are insulated from each other. The first head member 521, the second head member 522, the drive wire 531 and the slider 532 may all be made of a conductive material, such as metal and a stainless steel material, or may be plated with a conductive layer on their surfaces to achieve a function of electric conduction. In some embodiments, the drive part connecting pins 550a-b and the pivotal connecting pin 551 may be made of a conductive material or an insulating material.

As shown in FIGS. 29 and 32, the sealing member 540 may comprise an inner tubular portion 541, an outer tubular portion 542, and a curved transition portion 543. The inner tubular portion 541 may be sleeved over an outer peripheral surface of the proximal end of the slider 532 (e.g., of the sliding sleeve 534, or the slide bar 5322) and located in the inner cavity 5121 of the support part 510, and the inner tubular portion 541 can be driven by the slider 532 to axially move along the inner cavity 5121. An outer wall of the outer tubular portion 542 may be attached to an inner peripheral surface of the proximal end of the support part 510 in a sealed manner, or enclose the outer peripheral surface of the proximal end of the support part 510 in a sealed manner. The outer tubular portion 542 is integrally connected to the inner tubular portion 541 via the curved transition portion 543. Thus, with the sealing member 540, it is possible to seal the distal end of slider 532, the head part 520 and the drive wire 531 relative to the distal side of the sealing member 540, so that the drive wire 531 is isolated from a surgical interface.

In some embodiments, as shown in FIGS. 29 and 32, a ferrule 580 may be sleeved outside the inner tubular portion 541 of the sealing member 540 so that the sealing member 540 is connected to the slider 532 in a sealed and secured manner. In some embodiments, a ferrule (not shown in the figure) may also be sleeved outside the outer tubular portion 542 of the sealing member 540, and the ferrule may be connected to the proximal end of the support part 510 in a secured manner, so that the outer tubular portion 542 is connected to the proximal end of the support part 510 in a sealed and secured manner. With the arrangement of the ferrules, the sealing performance between the sealing member 540 and the drive wire 531 as well as between the sealing member 540 and the support part 510 can be further ensured respectively, and the risk of the sealing member 540 slipping off during expanding and retracting movements can be reduced.

Figure 34:
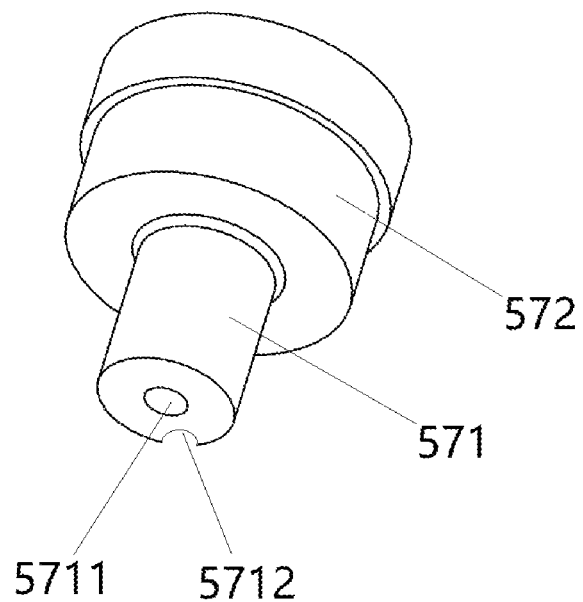
FIG. 34 shows a perspective view of a protective sleeve according to some embodiments of the present disclosure.

FIG. 34 shows a perspective view of a protective sleeve 570 according to some embodiments of the present disclosure. In some embodiments, a protective sleeve 570 may also be arranged on the outer periphery of the proximal end of the support part 510. As shown in FIG. 34, the protective sleeve 570 may comprise a proximal segment 571 and a distal segment 572. The distal segment 572 has a radial dimension greater than that of the proximal segment 571. The distal segment 572 of the protective sleeve 570 may comprise a receiving groove at the distal end (not shown in the figure). The receiving groove of the protective sleeve 570 receives the proximal end of the support part 510 and forms a sealing with an end portion of the support part 510. Those skilled in the art should understand that the distal segment 572 and the proximal end of the support part 510 may be in threaded connection, in interference-fit connection, welded, bonded, integral molded, etc. The proximal segment 571 of the protective sleeve 570 receives the drive wire 531. A drive wire through hole 5711 and a conductive wire through hole 5712 respectively for the drive wire 531 and the conductive wire 590 to pass through may be formed in an end portion of the proximal segment 571 of the protective sleeve 570. As shown in FIG. 34, the conductive wire through hole 5712 may be a conductive wire slot arranged along a side wall of the protective sleeve 570. In some embodiments, the protective sleeve 570 may be an insulator of rubber, plastic, ceramic, etc. The protective sleeve 570 can insulate the surgical effector from an arm of a surgical tool, and can prevent contaminants from entering the interior of the surgical tool, which makes cleaning difficult.

Figure 35:
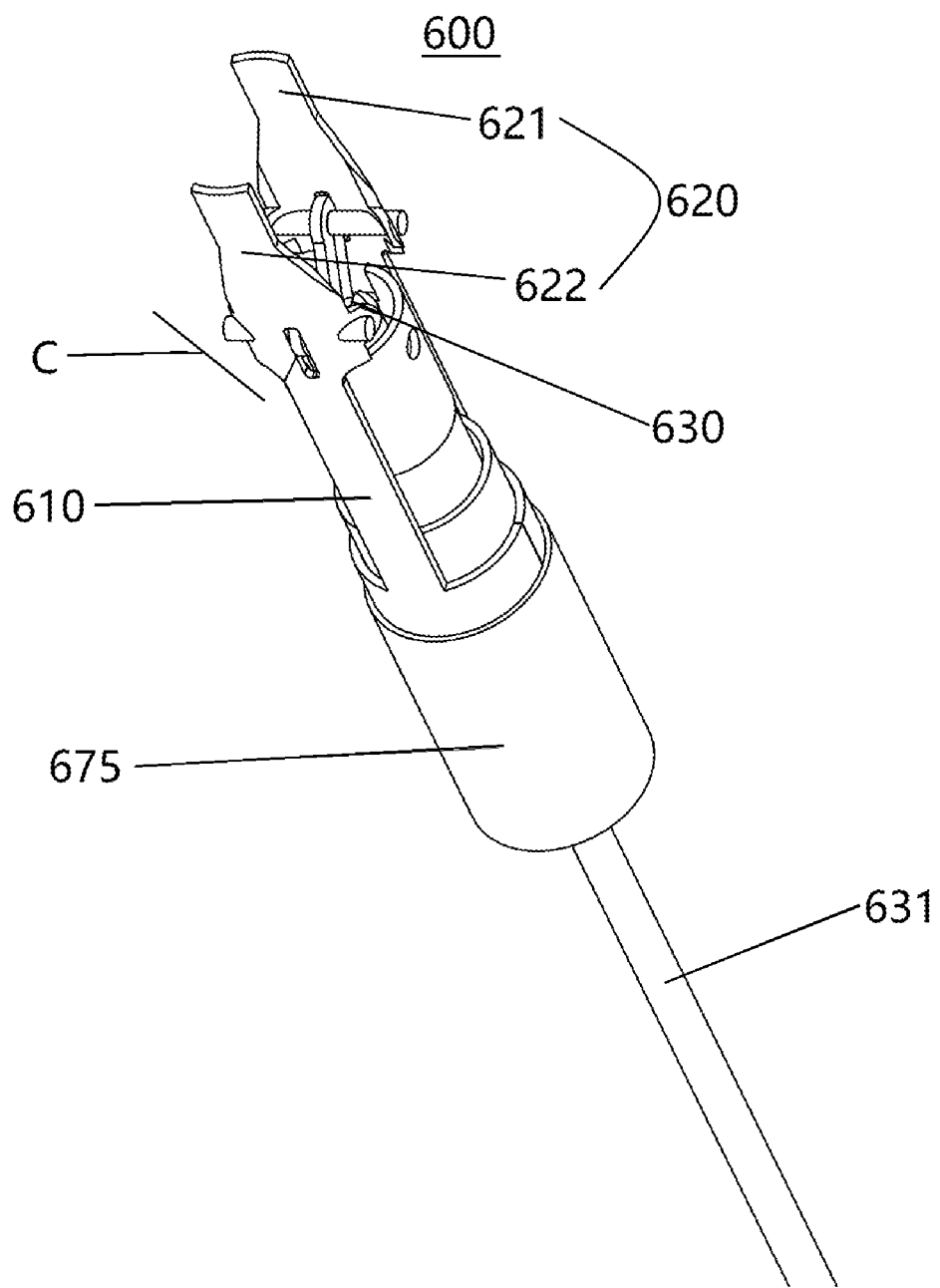
FIG. 35 shows a perspective view of a surgical effector according to some embodiments of the present disclosure.
Figure 36:
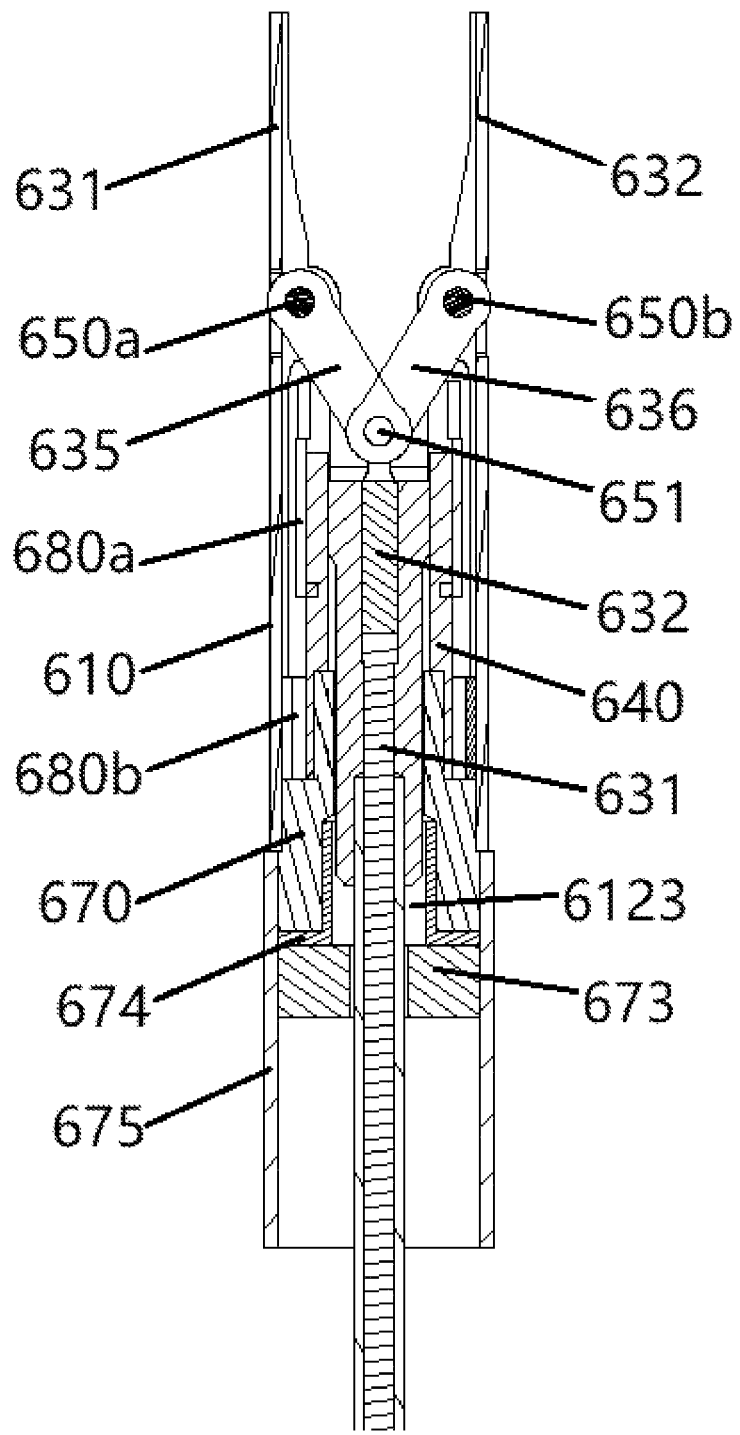
FIG. 36 shows a sectional view of a surgical effector according to some embodiments of the present disclosure.
Figure 37:
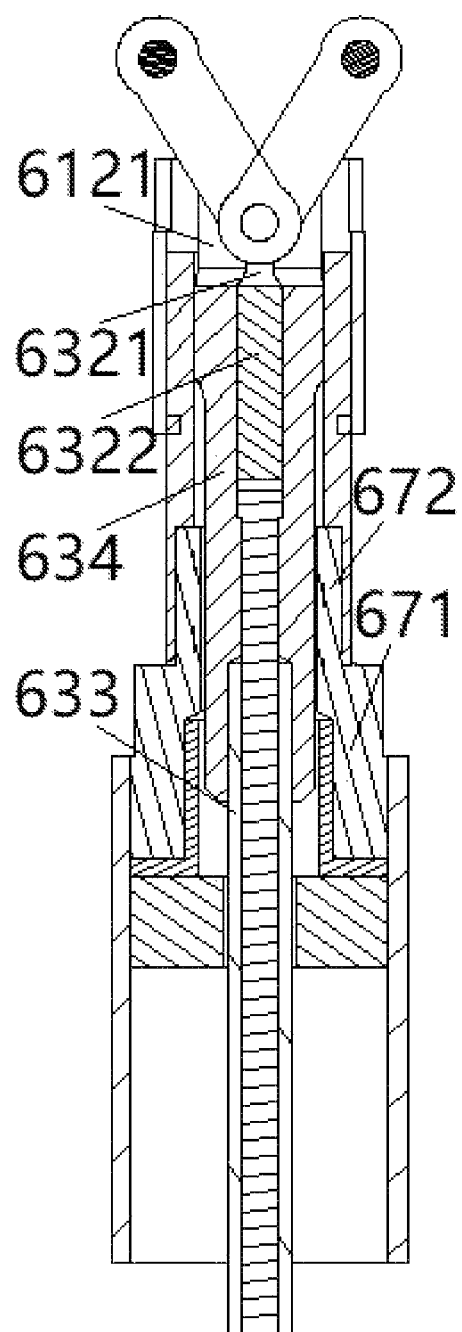
FIG. 37 shows a sectional view of a partial structure of a surgical effector according to some embodiments of the present disclosure.

FIGS. 35, 36 and 37 respectively show a perspective view, a sectional view, and a partial sectional view of a surgical effector 600 according to some embodiments of the present disclosure.

In some embodiments, the surgical effector 600 may comprise a head part 620, a support part 610, a drive part 630, and a sealing member 640.

Figure 38:
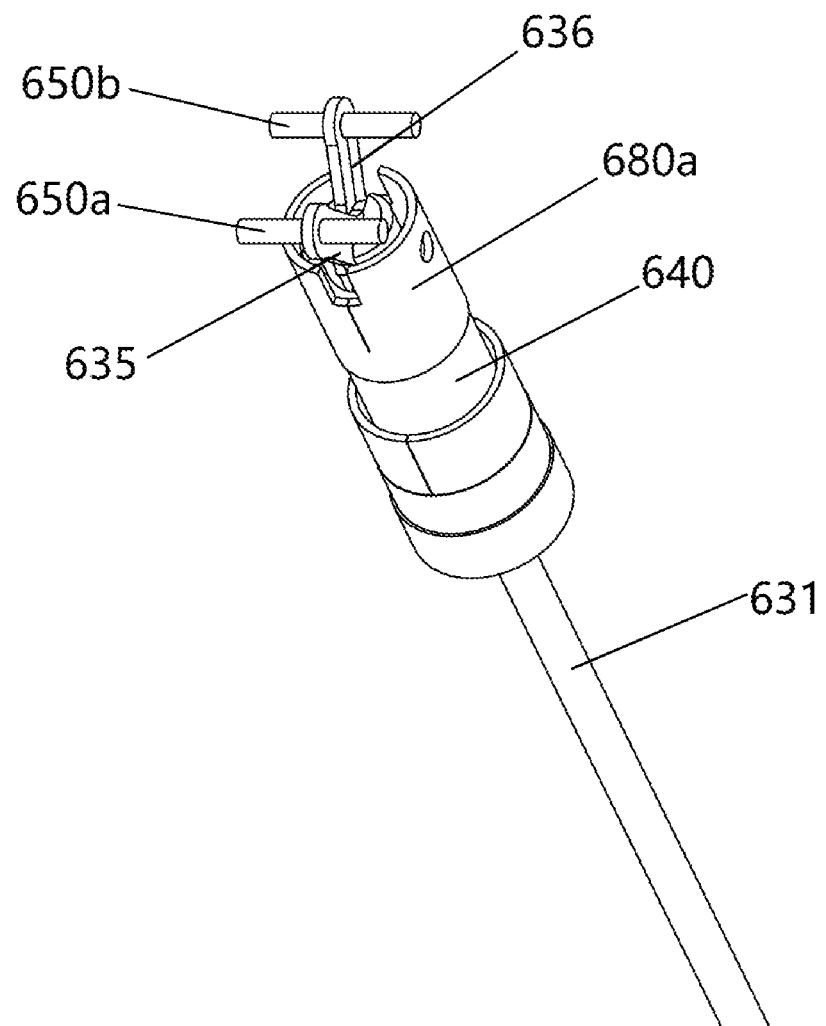
FIG. 38 shows a perspective view of a partial structure of a surgical effector according to some embodiments of the present disclosure.

As shown in FIG. 35, the head part 620 is at least partially movably arranged at a distal end of the support part 610. FIG. 38 shows a perspective view of a partial structure of a surgical effector according to some embodiments of the present disclosure. As shown in FIGS. 35 and 37, the support part 610 may comprise an inner cavity 6121, the drive part 630 may be slidably arranged in the inner cavity 6121 of the support part 610 and is connected to a proximal end of the head part 620, so that at least a part of the head part 620 is driven to move relative to the distal end of the support part 610 by the movement of the drive part inside the support part 610.

The sealing member 640 may be connected to an outer peripheral surface of the drive part 630 in a sealed manner at a first end (e.g., a proximal end, or a distal end shown in FIG. 36) thereof and be connected to an inner peripheral surface of the proximal end of the support part 610 in a sealed manner at a second end (e.g., a distal end, or a proximal end shown in FIG. 36) thereof, and at least a part of the sealing member 640 is deformable. Therefore, when the drive part 630 is relatively moved in the support part 610, the sealing member 640 can be deformed adaptively. The sealing member 640 can form a sealed isolation between the drive part 630, the support part 610 and the head part 620, so as to prevent patient's body fluids, bacteria and viruses from entering the interior of the surgical effector 600 through pores during a surgical operation, thereby facilitating repeated cleaning and disinfection of the surgical effector 600.

Figure 39:
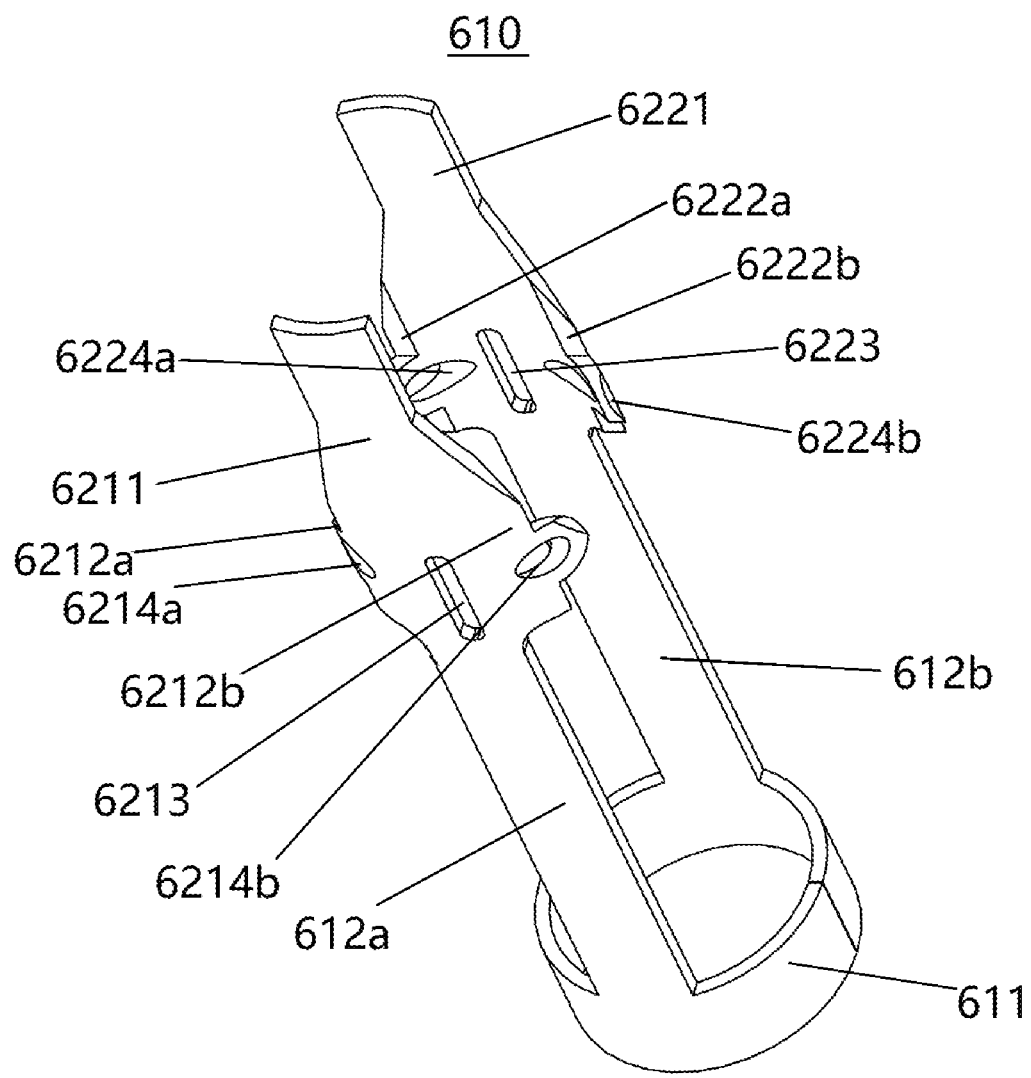
FIG. 39 shows a perspective view of a support part of a surgical effector according to some embodiments of the present disclosure.

FIG. 39 shows a perspective view of a support part 610 of a surgical effector according to some embodiments of the present disclosure. In some embodiments, as shown in FIG. 39, the support part 610 may comprise a support connector 611 at the proximal end and a pair of support members 612*a-b* arranged circumferentially spaced apart from each other at the distal end of the support connector 611. The support connector 611 may be tubular, and its cross section may be circular, oval, rectangular, polygonal, etc. The support members 612*a-b* may be fixedly connected to or integrally molded with the support connector 211. The support members of the support part 610 may be tubular or partially tubular, and their cross sections may be circular, oval, rectangular, polygonal, etc.

As shown in FIG. 39, the first head member 621 may comprise a jaw 6211 and a pair of first extension parts 6212*a-b* extending inwardly from two sides of the jaw 6211. The first extension parts 6212*a-b* are located inside the first head member 621, and the first extension parts 6212*a-b* may comprise a pair of connecting shaft through-holes 6214*a-b* arranged opposite each other. The second head member 622 may comprise a head member 6221 and a pair of second extension parts 6222*a-b* extending inwardly from two sides of the head member 6221. The second extension parts 6222*a-b* are located inside the second head member 622, and the second extension parts 6222*a-b* may comprise a pair of connecting shaft through-holes 6224*a-b* arranged opposite each other. In some embodiments, the first head member 621 may comprise an axially-extending jaw slot 6213, the second head member 622 may comprise an axially-extending jaw slot 6223, and the jaw slot 6213 and the jaw slot 6223 are arranged opposite each other to form a pair of jaw slots. As shown in FIGS. 35 and 38, a pair of drive part connecting pins 650*a-b* may be arranged in the connecting shaft through-holes 6214*a-b* of the first head member 621 and the connecting shaft through-holes 6224*a-b* of the second head member 622, respectively. The connecting shaft through-holes 6214*a-b* and 6224*a-b* may be configured to be connected to the drive part 630 respectively, as will be described in detail below.

In some embodiments, the first head member 621 and the second head member 622 are fixedly arranged at the distal end of the support part 610, and joints between the first head member 621 and/or the second head member 622 and the distal ends of the support members 612*a-b* are flexible, or the first head member 621 and the second head member 622 themselves are flexible. In some embodiments, the first head member 621 and the second head member 622 may be integrally molded with the support members 612*a-b*, as shown in FIG. 35. In some embodiments, the first head member 621 and the second head member 622 may be movably arranged at the distal ends of the support members 612*a-b*, respectively. The first head member 621 and the second head member 622 can be opened and closed under the driving of the drive wire 631, so that the size of the surgical effector 600 is reduced, thereby meeting the surgical requirements of tissue sites in small space, and the problem of operational inconvenience caused by the oversized existing surgical effector can be solved.

In some embodiments, the drive part 630 comprises a drive wire 631, as shown in FIGS. 35 and 38.

In some embodiments, the drive part connecting pins 650*a-b* may be connected to the drive wire 631 via a first connecting rod 635 and a second connecting rod 636, respectively. End portions of inner ends of the first connecting rod 635 and the second connecting rod 636 are hinged to each other, and the distal end of the drive wire 631 is connected to a hinged joint between the first connecting rod 635 and the second connecting rod 636. End portions of outer ends of the first connecting rod 635 and the second connecting rod 636 are respectively connected to the drive part connecting pins 650*a-b*, so that the first head member 621 and the second head member 622 can be driven by the drive wire 631 to approach each other or move away from each other.

In some embodiments, the drive part connecting pin 650*a* may be fixedly arranged in the connecting shaft through-holes 6214*a-b* of the first head member 621, and the drive part connecting pin 650*b* may be fixedly arranged in the connecting shaft through-holes 6214*a-b* of the second head member 622. The end portions of the inner ends of the first connecting rod 635 and the second connecting rod 636 may be hinged to each other via a pivotal connecting pin 651. The end portion of the outer end of the first connecting rod 635 may be hinged to the drive part connecting pin 650*a*. The end portion of the outer end of the second connecting rod 636 may be hinged to the drive part connecting pin 650*b*. The pivotal connecting pin 651 may be fixedly connected to the distal end of the drive wire 631. In some embodiments, the end portions of the inner ends of the first connecting rod 635 and the second connecting rod 636 may be directly hinged to the distal end of the drive wire 631. When the drive wire 631 is pulled toward the proximal end, the end portions of the outer ends of the first connecting rod 635 and the second connecting rod 636 approach each other, thereby driving the first head member 621 and the second head member 622 to approach each other. When the drive wire 631 moves toward the distal end, the end portions of the outer ends of the first connecting rod 635 and the second connecting rod 636 move away from each other, thereby driving the first head member 621 and the second head member 622 to move away from each other. The second head member 622 may move in a direction indicated by a movement trajectory C, and the first head member 621 may move in a direction away from the movement trajectory C, as shown in FIG. 35.

In some embodiments, as shown in FIG. 39, the jaw slots 6213 and 6223 are used for allowing the end portions of the outer ends of the first connecting rod 635 and the second connecting rod 636 to extend into same. When the first connecting rod 635 and the second connecting rod 636 reciprocate with the drive wire 631, the end portions of the outer ends of the first connecting rod 635 and the second connecting rod 636 can respectively move in the jaw slots 6213 and 6223. The jaw slots 6213 and 6223 can further reduce the transverse dimension of the head part 620.

In some embodiments, as shown in FIG. 36, the drive part 630 may further comprise a slider 632, and the end portions of the inner ends of the first connecting rod 635 and the second connecting rod 636 may be connected to a distal end of the slider 232 via the pivotal connecting pin 651. The distal end of the drive wire 631 is connected to a proximal end of the slider 632. The slider 632 is slidably arranged in the inner cavity of the support part 610, and the drive wire 631 is configured to drive the slider 632 to reciprocate in the support part 610.

In some embodiments, the slider 632 may comprise a slider connecting part 6321 and a slide bar 6322 extending axially from the slider connecting part 6321 to the proximal side. The slide bar 6322 and the slider connecting part 6321 may be integrally formed, or may be separate from and fixedly connected to each other, for example, by means of welding, bonding, or integral molding. The pivotal connecting pin 651 may be fixedly arranged on the slider connecting part 6321. In some embodiments, as shown in FIG. 37, a sliding sleeve 634 is sleeved over outer peripheries of the slide bar 6322 and the drive wire 631, and the sliding sleeve 634 and the slide bar 6322 or the slider connecting part 6321 may be integrally molded. It should be understood that the sliding sleeve 634 and the slide bar 6322 or the slider connecting part 6321 may alternatively be separate from and fixedly connected to each other, for example, by means of welding, bonding, or integral molding. In some embodiments, the slider 632 may be an insulator of rubber, plastic, ceramic, etc. The sealing member 640 may be sleeved over an outer peripheral surface of the sliding sleeve 634 in a sealed manner at the first end, and the sealing member 640 may also be attached to an inner peripheral surface of the proximal end of the support part 610 in a sealed manner or forms a sealing with the proximal end of the support part 610 at the second end, so that the distal end of the drive part 630 and the head part 620 are sealed relative to the inner side of the proximal end of the support part 610. Although in the above embodiments, the drive part 630 may comprise the slider 632, the drive wire 631, and the sliding sleeve 634, it should be understood that the drive part 630 may be wholly or at least partially integrally molded. In some embodiments, the slider 632 may be of a structure in a cylindrical shape, a cube shape, a polyhedron shape or a special shape.

In some embodiments, as shown in FIG. 37, the outer periphery of a part of the drive wire 631 located at the proximal end of the sliding sleeve 634 and outside the proximal end of the sliding sleeve 634 may be enclosed by an insulating protective sleeve 633, and the distal end of the drive wire 631 may pass through the insulating protective sleeve 633 and is connected to the end portion of the proximal end of the slider 632 in a secured manner, for example, by means of welding, bonding, integral molding, or secured snap-fit connection. The insulating protective sleeve 633 can ensure that during surgical operation, even if the surgical effector is in contact with an electrical device, no current will be conducted to the surgical tool arm, so that the patient and the user will not be burned, and safety hazards and device damage can be avoided.

In some embodiments, as shown in FIGS. 36 and 37, a protective sleeve 670 may also be arranged at the proximal end of the support part 610. The protective sleeve 670 may comprise a proximal segment 671 and a distal segment 672. The distal segment 672 has a radial dimension less than that of the proximal segment 671. As shown in FIG. 36, the proximal end of the support part 610 is closely sleeved over the outer periphery of the proximal segment 671 of the protective sleeve 670. In some embodiments, the support part 610 may be fixedly connected to or integrally molded with the protective sleeve 670. Those skilled in the art should understand that the proximal segment 671 and the proximal end of the support part 610 may be in threaded connection, in interference-fit connection, welded, bonded, integral molded, etc. In some embodiments, as shown in FIGS. 36 and 37, the proximal segment 671 and the distal segment 672 may be tubular, and their cross sections may be circular, oval, rectangular, polygonal, etc. An axially-arranged hollow slideway 6123 is formed in each of the proximal segment and the distal segment. In some embodiments, an outer wall of the protective sleeve 670 is closely attached to an inner wall of the support connector 611, an end portion of the proximal end of the protective sleeve 670 may be provided with a through hole for the drive wire 631 to pass through, and an axially-arranged hollow slideway is formed at the distal end of the protective sleeve 670 and used for sliding of the slider 632 and the drive wire 631. The sealing member 640 may be sleeved over an outer peripheral surface of the sliding sleeve 634 in a sealed manner at the first end, and the sealing member 640 may be sleeved over an outer peripheral surface of the distal end of the protective sleeve 670 in a sealed manner at the second end to realize sealing of the proximal end of the support part 610, so that the distal end of the drive part 630 and the head part 620 are sealed relative to the hollow slideway 6123 of the protective sleeve 670.

In some embodiments, the protective sleeve 670 may be made of a ceramic material, which can not only realize insulation but can also reduce friction, facilitating sliding of the slider 632 in the hollow slideway 6123. It should be understood that the protective sleeve 670 may be an insulator of rubber, plastic, etc. In some embodiments, as shown in FIG. 36, a fixing member 673 is arranged at an end portion of the proximal end of the protective sleeve 670, and the fixing member 673 may be directly fixedly connected to the end portion of the proximal end of the protective sleeve 670. In some embodiments, as shown in FIG. 36, the fixing member 673 may be fixedly connected to the protective sleeve 670 via a transition member 674. The fixing member 673 may be provided with a through hole for the drive wire 631 to pass through. The fixing member 673 can form a sealing with the proximal end of the drive part 630 to prevent tissue fluids from penetrating into the drive part 630, making cleaning difficult. It should be understood that the fixing member 673 and the protective sleeve 670 may be integrally molded.

In some embodiments, the sealing member 640 may be tubular, and its cross section may be circular, oval, rectangular, polygonal, etc. The distal end of the sealing member 640 forms the first end, and the proximal end of the sealing member 640 forms the second end. The sealing member 640 may be sleeved over an outer peripheral surface of the slider 632 in a sealed and enclosed manner at the first end. The sealing member 640 may be sleeved over the outer periphery of the distal segment 672 of the protective sleeve 670 in a sealed and enclosed manner at the second end. The sealing member 640 can seal the distal end of the slider 632, the head part 620 and the drive wire 631 relative to the hollow slideway 6123 of the protective sleeve 670, so that the drive wire 631 is isolated from a surgical interface.

In some embodiments, as shown in FIG. 36, a ferrule 680a may be sleeved outside the distal end of the sealing member 640 so that the sealing member 640 is connected to the slider 632 in a sealed and secured manner. In some embodiments, a ferrule 680b may also be sleeved outside the proximal end of the sealing member 640, and the sealing member 640 can be connected to the distal segment 672 of the protective sleeve 670 in a sealed and secured manner by means of the ferrule 680b. With the arrangement of the ferrules 680a-b, the sealing performance between the sealing member 640 and the drive wire 631 as well as between the sealing member 640 and the protective sleeve 670 can be ensured respectively, and the risk of the sealing member 640 slipping off during expanding and retracting movements can be reduced.

In some embodiments, as shown in FIG. 36, a shield 675 may be arranged at the proximal end of the support part 610. The shield 675 may be a tubular member, and its cross section may be circular, oval, rectangular, polygonal, etc. A distal end of the shield 675 is tightly sleeved over the outer periphery of the proximal lend of the protective sleeve 670 and the outer periphery of the fixing member 673. An inner wall of the shield 675 is fixedly connected to an outer wall of the fixing member 673. An end portion of the proximal end of the shield 675 is provided with a through hole for the drive wire 631 to pass through. In some embodiments, the shield 675 may be fixedly connected to or integrally molded with the support part 610. The shield 675 can further prevent body fluids from entering the surgical effector.

Figure 40:
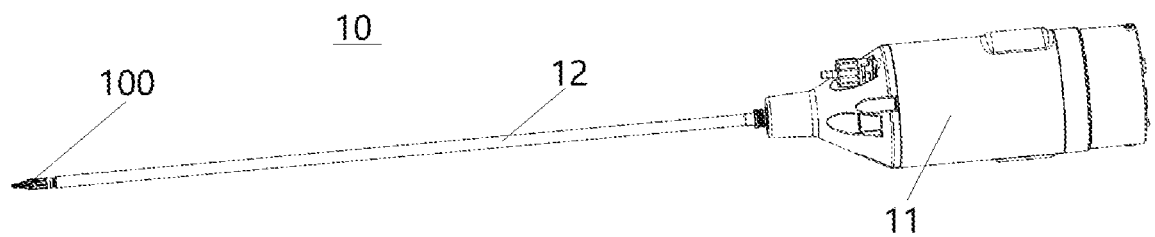
FIG. 40 shows a perspective view of a surgical tool according to some embodiments of the present disclosure.

FIG. 40 shows a perspective view of a surgical tool 10 according to some embodiments of the present disclosure. The surgical tool 10 may comprise a transmission part 11, a surgical tool arm 12, and the surgical effector 100 (or any one of surgical effectors 200 to 600). As shown in FIG. 40, the surgical effector 100 is arranged at a distal end of the surgical tool arm 12, the transmission part 11 is arranged at a proximal end of the surgical tool arm 12, the transmission part 11 can drive the drive wire 131 in the surgical effector 100 to move, and the head part 120 then can be driven to move by means of the drive wire 131. In some embodiments, the transmission part 11 can also drive the surgical tool arm 12 to move, so as to adjust the posture of the surgical effector 100 by means of the surgical tool arm 12.

In some embodiments, the transmission part 11 may comprise a transmission unit configured to be connected to an external motor drive unit, so that the drive wire can be driven. In some embodiments, the transmission part 11 may further comprise a motor drive unit which can drive the transmission unit, and the drive wire can be driven by the transmission unit.

In some embodiments, the surgical tool arm 12 may be a rigid arm body. In some embodiments, at least a part of the surgical tool arm 12 may be flexible, and may bend and move under the driving of the transmission part 11, so that the posture of the surgical effector at the distal end can be adjusted.

Figure 41:
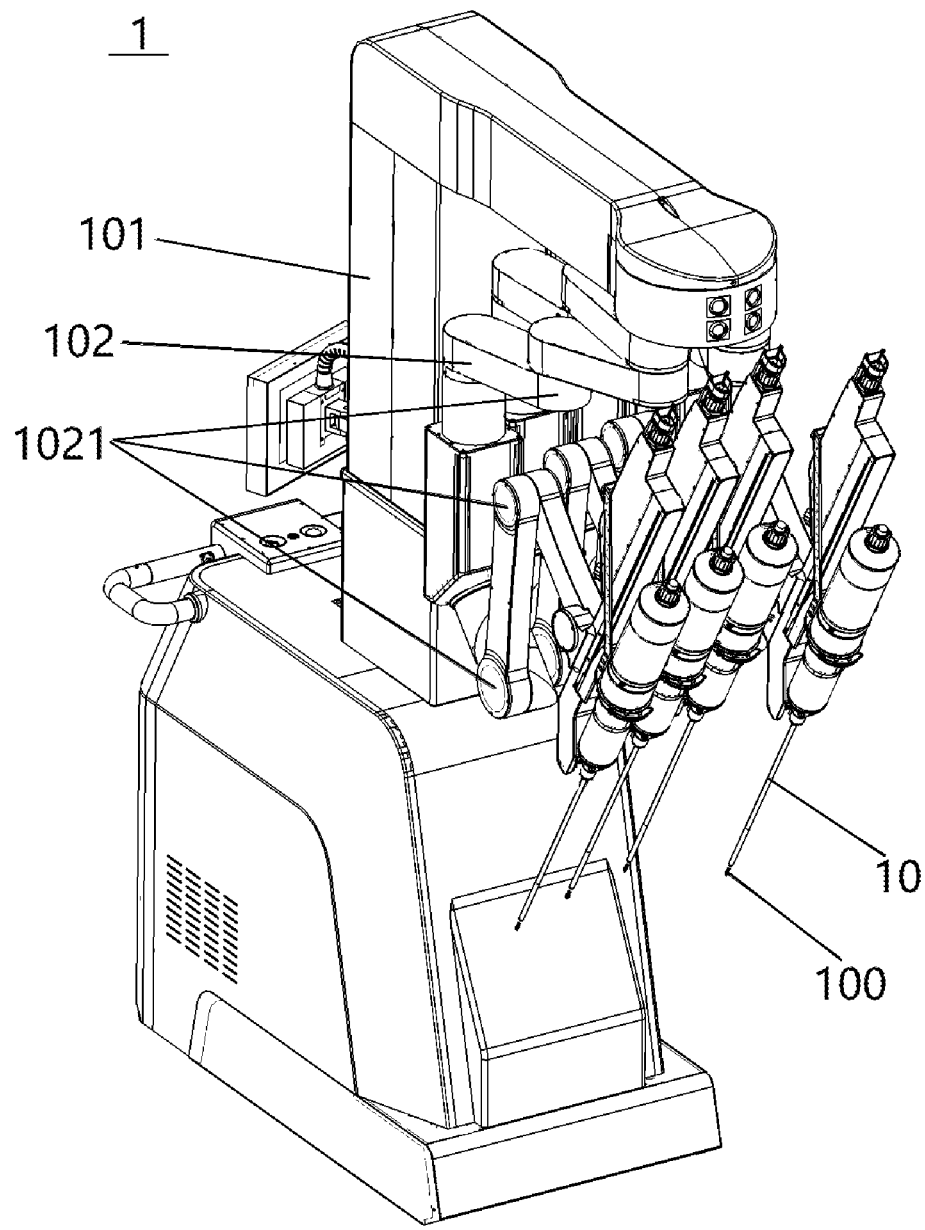
FIG. 41 shows a perspective view of a surgical robot according to some embodiments of the present disclosure.

FIG. 41 shows a perspective view of a surgical robot 1 according to some embodiments of the present disclosure.

As shown in FIG. 41, the surgical robot 1 may comprise a control device (not shown in the figure), a surgical cart 101, at least one robot arm 102, at least one surgical tool or endoscope 10, and at least one surgical effector 100 (or any one of the surgical effectors 200 to 600).

As shown in FIG. 41, the at least one robot arm 102 is arranged on the surgical cart 101, and the surgical cart 101 may be configured to support the robot arm 102. The at least one surgical tool 10 is respectively arranged at a distal end of the at least one robot arm 102, and the at least one surgical effector 100 is respectively arranged at a distal end of the at least one surgical tool 10. The control device may be configured to control movements of the robot arm 102, the at least one surgical tool 10 and/or the at least one surgical effector 100 through teleoperation. The robot arm 102 may comprise at least one movable joint 1021, and the posture of the surgical tool 10 may be adjusted by means of the movable joint 1021. Those skilled in the art should understand that the at least one robot arm 102 may alternatively respectively arranged on a plurality of surgical carts 101.

The following features are also disclosed in the present disclosure.

Item 1: A surgical effector, comprising:
a support part comprising an inner cavity;
a head part at least partially movably arranged at a distal end of the support part;
a drive part slidably arranged in the inner cavity of the support part and connected to a proximal end of the head part; and
a sealing member connected to the drive part in a sealed manner at a first end thereof and connected to the support part in a sealed manner at a second end thereof, at least a part of the sealing member being deformable.

Item 2: The surgical effector of item 1, wherein the head part comprises a first head member and a second head member capable of mating with the first head member.

Item 3: The surgical effector of item 2, wherein the drive part comprises a drive wire.

Item 4: The surgical effector of item 3, wherein the drive wire is connected to the second head member by at least one first drive part connecting pin for transmitting a drive force from the drive wire to the second head member.

Item 5: The surgical effector of item 4, wherein the drive wire is connected to the first head member by at least one second drive part connecting pin for transmitting a drive force from the drive wire to the first head member.

Item 6: The surgical effector of item 5, wherein the drive part comprises a first connecting rod and a second connecting rod;
end portions of inner ends of the first connecting rod and the second connecting rod are hinged to each other;
a distal end of the drive wire is connected to a hinged joint between the first connecting rod and the second connecting rod; and
end portions of outer ends of the first connecting rod and the second connecting rod are respectively connected to the corresponding first and second drive part connecting pins, and the second drive part connecting pin and the first drive part connecting pin are respectively connected to the first head member and the second head member, so that the first head member and the second head member are driven by the drive wire to approach each other or move away from each other.

Item 7: The surgical effector of item 4 or 5, wherein the drive part further comprises: a slider;
the slider is slidably arranged in the inner cavity of the support part, and a distal end of the slider is connected to the drive part connecting pin; and
the distal end of the drive wire is connected to a proximal end of the slider to drive the slider to reciprocate in the support part.

Item 8: The surgical effector of item 4, wherein the first head member is fixedly arranged at the distal end of the support part, and the second head member is movably arranged at the distal end of the support part.

Item 9: The surgical effector of item 4, wherein the support part comprises at least one pair of support part slide slots, and the at least one first drive part connecting pin is slidably arranged in the at least one pair of support part slide slots.

Item 10: The surgical effector of item 9, wherein the second head member comprises a jaw and jaw support members which are connected to and support the jaw, the jaw support members are symmetrically arranged on two sides of a proximal end of the second head member, and the jaw support members are pivotally connected to the support part by a pivotal connecting pin; and
the jaw support members comprise jaw slide slots, and the at least one first drive part connecting pin is slidably arranged in the at least one pair of support part slide slots and the jaw slide slots.

Item 11: The surgical effector of item 10, wherein the support part slide slots are at least one pair of axial slide slots symmetrically arranged on the support part, and the jaw slide slots are arc-shaped slide slots symmetrically arranged on the jaw support members.

Item 12: The surgical effector of item 5, wherein the first head member and the second head member are pivotally connected to the distal end of the support part by a pivotal connecting pin.

Item 13: The surgical effector of item 12, wherein the support part comprises at least two pairs of support part slide slots, and at least one first drive part connecting pin and the second drive part connecting pin are respectively slidably arranged in the at least two pairs of support part slide slots.

Item 14: The surgical effector of item 13, wherein the first head member comprises a first jaw and first jaw support members which are connected to and support the first jaw, the jaw support members are symmetrically arranged on two sides of a proximal end of the first jaw, and the first jaw support members are pivotally connected to the support part by a pivotal connecting pin;

the first jaw support members comprise first jaw slide slots, and the at least one second drive part connecting pin is slidably arranged in one pair of support part slide slots and the first jaw slide slots;

the second head member comprises a second jaw and second jaw support members which are connected to and support the second jaw, the second jaw support members are symmetrically arranged on two sides of a proximal end of the second jaw, and the second jaw support members are pivotally connected to the support part by a pivotal connecting pin; and the second jaw support members comprise second jaw slide slots, and the at least one first drive part connecting pin is slidably arranged in the other pair of support part slide slots and the jaw slide slots.

Item 15: The surgical effector of item 6, wherein the first head member and the second head member are fixedly arranged at the distal end of the support part, joints between the first head member and/or the second head member and the distal end of the support part are flexible, or the first head member and the second head member themselves are flexible.

Item 16: The surgical effector of any one of item 2-14, wherein a proximal end of the drive wire is connected to a power supply apparatus so that a conductive pathway is formed between the second head member and the drive wire.

Item 17: The surgical effector of item 16, wherein the first head member is connected to another power supply apparatus so that another conductive pathway is formed between the first head member and the another power supply apparatus; and the conductive pathway and the another conductive pathway are insulated from each other.

Item 18: The surgical effector of item 17, wherein an insulation part is arranged between at least one of the first head member and the second head member, and the support part so that the first head member and the second head member are insulated from each other.

Item 19: The surgical effector of item 18, wherein the insulation part comprises a first insulating member arranged at the joint between the first head member and the support part; or the insulation part comprises a support frame insulating lining closely attached to an inner wall of the support part, and a second insulating member arranged at a contact position between the second head member and the support part.

Item 20: The surgical effector of any one of items 7-19, wherein the sealing member is attached around an outer periphery of the proximal end of the slider in a sealed manner at the first end; or the sealing member is attached around a proximal end of the support part in a sealed manner at the second end; or the sealing member is attached to an inner wall of the support part in a sealed manner at the second end.

Item 21: The surgical effector of item 14; further comprising: a ferrule secured on an outer periphery of the sealing member at the first and/or second end.

Item 22: The surgical effector of item 14, wherein the slider further comprises: a slide bar and a pin connecting part; and the sealing member is attached around at least a part of an outer periphery of the slide bar in a sealed manner at the first end.

Item 23: The surgical effector of any one of items 1-20, wherein the sealing member comprises an inner tubular portion, an outer tubular portion, and a transition portion connected to the inner tubular portion and the outer tubular portion, a distal end of the inner tubular portion forms the first end, and a distal end of the outer tubular portion forms the second end.

Item 24: The surgical effector of any one of items 1-20, wherein the sealing member is tubular, a distal end of the sealing member forms the first end, and a proximal end of the sealing member forms the second end.

Item 25: The surgical effector of any one of items 1-22, further comprising: a protective sleeve, wherein the protective sleeve is provided with a receiving groove at a distal end thereof, and the receiving groove is closely sleeved over the outer periphery of the proximal end of the support part; and a through hole for the drive part to pass through is formed at an end portion of a proximal end of the protective sleeve.

Item 26: The surgical effector of any one of item 2-23, wherein the distal end of the support part is provided with at least one support member spaced apart circumferentially and extending axially, and the first head member and the second head member are arranged at a distal end of the support member.

Item 27: The surgical effector of any one of items 1-24, wherein at least a part of the sealing member comprises an elastic material or a flexible material.

Item 28: The surgical effector of any one of items 1-25, wherein the head part comprises at least one of the following: separating forceps, grasping forceps, a needle holder, and curved scissors.

Item 29: A surgical tool, comprising a transmission part, a surgical tool arm, and the surgical effector of any one of items 1-26, wherein the surgical effector is arranged at a distal end of the surgical tool arm, the transmission part is arranged at a proximal end of the surgical tool arm, and the transmission part is to drive the surgical tool arm and/or the surgical effector to move.

Item 30: A surgical robot, comprising at least one control device, at least one surgical cart, at least one robot arm, at least one surgical tool, and at least one surgical effector of any one of items 1-26, wherein the at least one robot arm is arranged on the at least one surgical cart, the at least one surgical tool is arranged at a distal end of the at least one robot arm, the at least one surgical effector is arranged at a distal end of the at least one surgical tool, and the at least one control device is to control the movement of the at least one surgical tool and/or the at least one surgical effector.

It is to be noted that only exemplary embodiments of the present disclosure and the technical principles employed have been described above. Those skilled in the art will understand that the present disclosure is not limited to the specific embodiments herein, and various obvious changes, rearrangements and substitutions can be made by those skilled in the art without departing from the scope of protection of the present disclosure. Therefore, although the present disclosure has been described in detail through the foregoing embodiments, the present disclosure is not limited to the above embodiments, and can also comprise more other equivalent embodiments without departing from the concept of the present disclosure. The scope of the present disclosure is determined by the scope of the appended claims.

The invention claimed is:

1. A surgical effector, comprising:
a support part comprising an inner cavity;
a head part at least partially movably arranged at a distal end of the support part;
a drive part slidably arranged in the inner cavity of the support part and connected to a proximal end of the head part; and
a sealing member connected to the drive part in a sealed manner at a first end thereof and connected to the support part in a sealed manner at a second end thereof, at least a part of the sealing member being deformable;
wherein the sealing member comprises an inner tubular portion, an outer tubular portion, and a transition portion connected to the inner tubular portion and the outer tubular portion, a distal end of the inner tubular portion forms the first end, and a distal end of the outer tubular portion forms the second end.

2. The surgical effector according to claim 1, wherein the head part comprises a first head member and a second head member capable of mating with the first head member; and the drive part comprises a drive wire.

3. The surgical effector according to claim 2, wherein the drive wire is connected to the second head member by at least one first drive part connecting pin for transmitting a drive force from the drive wire to the second head member.

4. The surgical effector according to claim 3, wherein the drive wire is connected to the first head member by at least one second drive part connecting pin for transmitting a drive force from the drive wire to the first head member.

5. The surgical effector according to claim 4, wherein the drive part comprises a first connecting rod and a second connecting rod;
end portions of inner ends of the first connecting rod and the second connecting rod are hinged to each other;
a distal end of the drive wire is connected to a hinged joint between the first connecting rod and the second connecting rod; and
end portions of outer ends of the first connecting rod and the second connecting rod are respectively connected to corresponding one of the first and second drive part connecting pins, and the second drive part connecting pin and the first drive part connecting pin are respectively connected to the first head member and the second head member, so that the first head member and the second head member are driven by the drive wire to approach each other or move away from each other.

6. The surgical effector according to claim 4, wherein the first head member and the second head member are pivotally connected to the distal end of the support part by a pivotal connecting pin.

7. The surgical effector according to claim 3, wherein the drive part further comprises: a slider;
the slider is slidably arranged in the inner cavity of the support part, and a distal end of the slider is connected to the drive part connecting pin; and
the distal end of the drive wire is connected to a proximal end of the slider to drive the slider to reciprocate in the support part.

8. The surgical effector according to claim 7, wherein the sealing member is attached around an outer periphery of the proximal end of the slider in a sealed manner at the first end; or the sealing member is attached around a proximal end of the support part in a sealed manner at the second end; or the sealing member is attached to an inner wall of the support part in a sealed manner at the second end.

9. The surgical effector according to claim 8, further comprising: a ferrule secured on an outer periphery of the sealing member at the first and/or second end.

10. The surgical effector according to claim 8, wherein the slider further comprises: a slide bar and a pin connecting part; and
the sealing member is attached around at least a part of an outer periphery of the slide bar in a sealed manner at the first end.

11. The surgical effector according to claim 3, wherein the first head member is fixedly arranged at the distal end of the support part, and the second head member is movably arranged at the distal end of the support part.

12. The surgical effector according to claim 3, wherein the support part comprises at least one pair of support part slide slots, and at least one first drive part connecting pin is slidably arranged in the at least one pair of support part slide slots.

13. The surgical effector according to claim 12, wherein the second head member comprises a jaw and jaw support members which are connected to and support the jaw, the jaw support members are symmetrically arranged on two sides of a proximal end of the second head member, and the jaw support members are pivotally connected to the support part by a pivotal connecting pin; and
the jaw support members comprise jaw slide slots, and at least one first drive part connecting pin is slidably arranged in the at least one pair of support part slide slots and the jaw slide slots.

14. The surgical effector according to claim 2, wherein a proximal end of the drive wire is connected to a power supply apparatus so that a conductive pathway is formed between the second head member and the drive wire.

15. The surgical effector according to claim 14, wherein the first head member is connected to another power supply apparatus so that another conductive pathway is formed between the first head member and the another power supply apparatus; and
the conductive pathway and the another conductive pathway are insulated from each other.

16. The surgical effector according to claim 15, wherein an insulation part is arranged between at least one of the first and second head members and the support part, so that the first head member and the second head member are insulated from each other.

17. The surgical effector according to claim 1, wherein at least a part of the sealing member comprises an elastic material or a flexible material.

18. A surgical tool comprising:
a surgical tool arm;
a surgical effector arranged at a distal end of the surgical tool arm; and a transmission part arranged at a proximal end of the surgical tool arm and configured to drive the surgical tool arm or the surgical effector to move;

wherein the surgical effector comprises:
- a support part comprising an inner cavity;
- a head part at least partially movably arranged at a distal end of the support part;
- a drive part slidably arranged in the inner cavity of the support part and connected to a proximal end of the head part; and
- a sealing member connected to the drive part in a sealed manner at a first end thereof and connected to the support part in a sealed manner at a second end thereof, at least a part of the sealing member being deformable;
- wherein the sealing member comprises an inner tubular portion, an outer tubular portion, and a transition portion connected to the inner tubular portion and the outer tubular portion, a distal end of the inner tubular portion forms the first end, and a distal end of the outer tubular portion forms the second end.

19. A surgical robot comprising:
at least one surgical cart;
at least one robot arm arranged on the at least one surgical cart;
at least one surgical tool arranged at a distal end of the at least one robot arm respectively;
at least one surgical effector arranged at a distal end of the at least one surgical tool; and
at least one control device configured to control the movement of the at least one surgical tool or the at least one surgical effector; wherein the at least one surgical effector comprises:
- a support part comprising an inner cavity;
- a head part at least partially movably arranged at a distal end of the support part;
- a drive part slidably arranged in the inner cavity of the support part and connected to a proximal end of the head part; and
- a sealing member connected to the drive part in a sealed manner at a first end thereof and connected to the support part in a sealed manner at a second end thereof, at least a part of the sealing member being deformable.

20. The surgical robot according to claim 19, wherein the sealing member comprises:
an inner tubular portion;
an outer tubular portion; and
a transition portion connected to the inner tubular portion and the outer tubular portion;
wherein a distal end of the inner tubular portion forms the first end, and a distal end of the outer tubular portion forms the second end.

\* \* \* \* \*